United States Patent
Chen

(10) Patent No.: US 7,517,873 B2
(45) Date of Patent: Apr. 14, 2009

(54) SUBSTITUTED PYRIMIDODIAZEPINES

(75) Inventor: Shaoqing Chen, Bridgewater, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/051,000

(22) Filed: Mar. 19, 2008

(65) Prior Publication Data

US 2008/0234255 A1 Sep. 25, 2008

Related U.S. Application Data

(60) Provisional application No. 60/919,358, filed on Mar. 22, 2007.

(51) Int. Cl.
*C07D 257/10* (2006.01)
*C07C 69/74* (2006.01)
*A61K 31/551* (2006.01)

(52) U.S. Cl. .................. 514/221; 540/501; 560/121
(58) Field of Classification Search ............... 540/501; 560/121; 514/221
See application file for complete search history.

(56) References Cited

U.S. PATENT DOCUMENTS

2008/0009482 A1    1/2008    Halsall et al.

FOREIGN PATENT DOCUMENTS

| WO | WO 01/19828 | 3/2001 |
|---|---|---|
| WO | WO 03/020722 | 3/2003 |
| WO | WO 2007/095188 | 8/2007 |
| WO | WO 2008/003958 | 1/2008 |

OTHER PUBLICATIONS

Haugwitz et al., J. Med. Chem., 25, pp. 969-974 (1982).

*Primary Examiner*—Bruck Kifle
(74) *Attorney, Agent, or Firm*—George W. Johnston; Patricia S. Rocha-Tramaloni; David E. Wildman

(57) ABSTRACT

The present invention provides PLK1 inhibitor compounds of formula I:

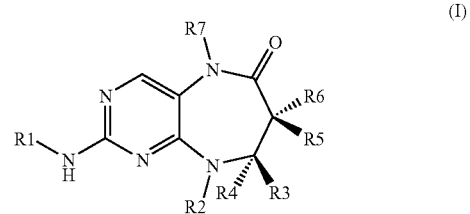

Useful in the treatment or control of cell proliferative disorders, particularly oncological disorders. These compounds and formulations containing such compounds may be useful in the treatment or control of solid tumors, such as, for example, breast, colon, lung and prostate tumors and other oncological diseases such as non-Hodgkin's lymphomas.

7 Claims, No Drawings

SUBSTITUTED PYRIMIDODIAZEPINES

PRIORITY TO RELATED APPLICATION(S)

This application claims the benefit of U.S. Provisional Application No. 60/919,358, filed Mar. 22, 2007, which is hereby incorporated by reference in its entirety.

PLK1 is a member of the Polo-like kinase family. Polo-like kinases are highly conserved from yeast to humans and play a variety of roles in the G2/M phase transition and in the passage through mitotic phase of the cell cycle. Four Polo-like kinases, PLK1, PLK2 (Snk), PLK3 (Fnk), and PLK4 have been identified in humans. These proteins share extensive homologies across their kinase domains, in C-terminal "Polo" boxes. Using neutralizing antibodies, anti-sense oligos, and dominant-negative protein, PLK1 was shown to be essential for mitosis in vitro cultured cells. Furthermore, down regulation of PLK1 appears to have differential effects in tumor versus "normal" cells in that ablation of PLK1 induced mitotic catastrophe and eventual cell death in tumor cells, but G2 arrest in "normal" cells. One plausible explanation is that tumor cells are defective in checkpoint controls and unable to arrest and thus undergo mitotic catastrophe. The roles of PLK2, PLK3, and PLK4 remain elusive.

The expression of PLK1 is restricted to proliferative tissues. Overexpression of PLK1 was detected in solid tumors of various origins (breast, lung, colon, stomach, ovary, smooth muscle, and esophagus) and in non-Hodgkin lymphomas. Furthermore PLK1 has transforming activity; constitutive expression of PLK1 in NIH3T3 cells causes oncogenic focus formation, transformed cells grow in soft agar and form tumors in nude mice. Therefore, blocking PLK1 kinase activity by a small molecule inhibitor represents a novel approach to target mitosis and may be clearly differentiated from other mitosis-targeting agents on the market such as tubulin binders.

Other therapies which involve the disruption of microtubule formation and degradation through the use of taxanes and vinca alkaloids have become successful ways of treating cancer. Some cancerous cells are able to evade the G2/M cell cycle arrest effect of taxanes and vinca alkaloids. PLK1 inhibition provides a means to target those cells which are able to evade the G2/M cell cycle arresting effect of taxanes and vinca alkaloids.

According to a first aspect of the invention, there is provided a PLK1 inhibitor compound of formula I:

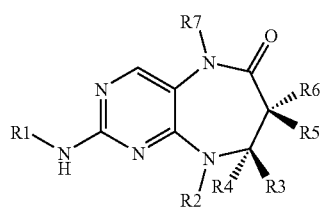

(I)

wherein R1 is a member selected from the group consisting of

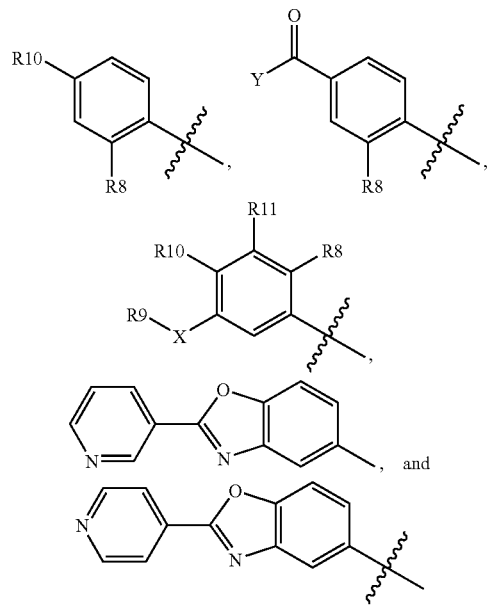

wherein
R2 is a member selected from the group consisting of C1-C5 straight or branched chain alkyl, allyl, aryl, benzyl, heteroaryl, vinyl, heterocyclyl, C3-C7 cycloalkyl optionally substituted by one or more C1-C3 alkyl groups, and C1-C3alkoxyC1-C3alkyl;

R3 and R4 are independently selected from the group consisting of hydrogen and methyl; or R2 and one of R3 and R4, together with the carbon and nitrogen to which they are attached, form a five membered ring;

R5 and R6 are independently selected from the group consisting of hydrogen, methyl, ethyl, propyl, hydroxymethyl, hydroxyethyl, cyclopropyl, chloro, fluoro, bromo, and iodo; or R5 and R6, together with the carbon to which they are attached, form cyclopropyl or cyclobutyl; or R4 and R6, together with the carbons to which they are attached, form a five membered ring; or R3 and R5, together with the carbons to which they are attached, form a five membered ring; or R2 and one of R5 and R6, together with the carbon and nitrogen to which they are attached, form a six membered ring;

R7 is a member selected from the group consisting of hydrogen, methyl, and ethyl;

Y is a member selected from the group consisting of hydroxyl, diC1-C3alkylamino, a six-membered heterocyclic ring containing one or two heteroatoms selected from the group consisting of N and O, and NH—R9;

R8 and R11 are independently selected from the group consisting of hydrogen, halogen, methyl, and methoxy;

R9 is a member selected from the group consisting of hydrogen, piperidinyl, N-benzyl piperidinyl, N—C1-C4alkyl piperidinyl, aryl, heteroaryl, C1-C4 alkyl, tetrahydropyranyl, imidazolyl-C1-C4alkyl, amino, and diC1-C3alkylaminoC1-C4alkyl;

R10 is a member selected from the group consisting of hydrogen, hydroxyl, and benzyloxy; and X is a member selected from the group consisting of —C(O)NH— and —NHC(O)—;

and pharmaceutically acceptable salts thereof.

In another aspect, the invention is directed to compounds of Formula I where R7 is methyl and variables R1 to R6 and R8 to R11 are as set out above.

In another aspect, the invention is directed to compounds of Formula I where R2 is cyclobutyl, cyclopentyl or cyclohexyl, R7 is methyl, and R1, R3 to R6 and R8 to R11 are as set out above.

In another aspect, the invention is directed to compounds of Formula I where R1 is

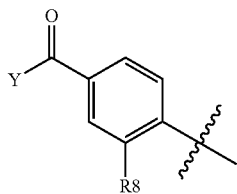

R2 is cyclopentyl or cyclohexyl, R7 is methyl, Y is NH—R9, R9 is 1-methyl-piperidin-4-yl or tetrahydropyran-4-yl, and R3 to R6 and R8 are as set out above.

In another aspect, the invention is directed to compounds of Formula I where R1 is

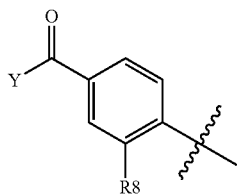

R2 is cyclopentyl or cyclohexyl, R5 and R6 are independently selected from the group consisting of hydrogen, methyl, and fluoro, or R5 and R6 together with the carbon to which they are attached form cyclopropyl, R7 is methyl, Y is NH—R9, R9 is 1-methyl-piperidin-4-yl or tetrahydropyran-4-yl, and R3, R4, and R8 are as set out above.

In another aspect, the invention is directed to compounds of Formula I where R1 is

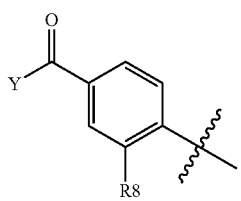

R2 is cyclopentyl, R5 and R6 are independently selected from the group consisting of hydrogen, methyl, and fluoro, or R5 and R6 together with the carbon to which they are attached form cyclopropyl, R7 is methyl, Y is NH—R9, R9 is 1-methyl-piperidin-4-yl, R3 and R4 are hydrogen, and R8 is methyl or methoxy.

In another aspect, the invention is directed to compounds of Formula I where R1 is

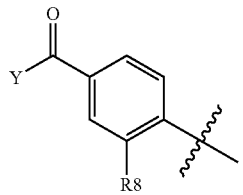

R2 is cyclopentyl, one of R5 and R6 is hydrogen and the other is methyl, R7 is methyl, Y is NH—R9, R9 is 1-methyl-piperidin-4-yl, R3 and R4 are hydrogen, and R8 is methoxy.

In another aspect, the invention is directed to compounds of Formula I where R1 is

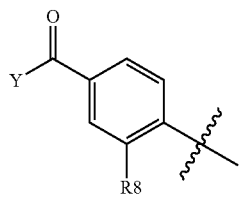

R2 is cyclopentyl, R5 and R6 fluoro, R7 is methyl, Y is NH—R9, R9 is 1-methyl-piperidin-4-yl, R3 and R4 are hydrogen, and R8 is methoxy.

In another aspect, the invention is directed to compounds of Formula I where R1 is

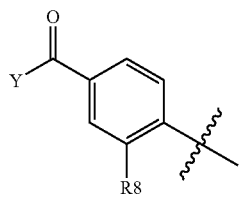

R2 is cyclopentyl, R5 and R6 together with the carbon to which they are attached form cyclopropyl, R7 is methyl, Y is NH—R9, R9 is 1-methyl-piperidin-4-yl, R3 and R4 are hydrogen, and R8 is methoxy.

In another aspect the invention is directed to compounds of Formula I selected from the group consisting of:
(rac)-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide;
7R-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide;
7S-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide;
(rac)-4-(9-cyclopentyl-5,7-dimethyl-6-oxo-6,7,8,9-tetrahydro-5H-pyrimido[4,5-b][1,4]diazepin-2-ylamino)-3-methyl-N-(1-methyl-piperidin-4-yl)-benzamide;
(rac)-N-(1-benzyl-piperidin-4-yl)-4-(9-cyclopentyl-5,7-dimethyl-6-oxo-6,7,8,9-tetrahydro-5H-pyrimido[4,5-b][1,4]diazepin-2-ylamino)-3-methoxy-benzamide;

4-(9-cyclopentyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide;
(rac)-4-(9-cyclopentyl-7-ethyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide;
(rac)-4-(9-cyclohexyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide;
4-(9-cyclohexyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide;
4-(9-cyclobutyl-5-methyl-6-oxo-6,7,8,9-tetrahydro-5H-pyrimido[4,5-b][1,4]diazepin-2-ylamino)-N-(3-imidazol-1-yl-propyl)-3-methoxy-benzamide;
4-(9-cyclopentyl-5,7,7-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide;
4-(9-isopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide;
4-(9-butyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide;
4-(9-cyclopentyl-5,7,7-trimethyl-6-oxo-6,7,8,9-tetrahydro-5H-pyrimido[4,5-b][1,4]diazepin-2-ylamino)-N-(1-methyl-piperidin-4-yl)-benzamide;
(rac)-4-(9-cyclobutyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide;
4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methoxy-N-(1-methyl-4-piperidinyl)benzamide;
4-(9-cyclopentyl-5,7,7-trimethyl-6-oxo-6,7,8,9-tetrahydro-5H-pyrimido[4,5-b][1,4]diazepin-2-ylamino)-3-methyl-N-(1-methyl-piperidin-4-yl)-benzamide;
(rac)-3-methoxy-4-[5-methyl-9-(2-methyl-cyclopentyl)-6-oxo-6,7,8,9-tetrahydro-5H-pyrimido[4,5-b][1,4]diazepin-2-ylamino]-N-(1-methyl-piperidin-4-yl)-benzamide;
4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methyl-N-(1-methyl-4-piperidinyl)benzamide;
4-[(9-cyclopentyl-6,7,8,9-tetrahydro-5-methyl-6-oxospiro[5H-pyrimido[4,5-b][1,4]diazepine-7,1'-cyclopropan]-2-yl)amino]-N-(1-methyl-4-piperidinyl)benzamide;
4-[(9-cyclopentyl-6,7,8,9-tetrahydro-5-methyl-6-oxospiro[5H-pyrimido[4,5-b][1,4]diazepine-7,1'-cyclopropan]-2-yl)amino]-N-(tetrahydropyran-4-yl)benzamide;
(rac)-4-(9-allyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide; and
4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide.

"Alkyl" denotes a straight-chained, branched or cyclic saturated aliphatic hydrocarbon. Alkyl includes lower alkyl, i.e., a C1-C6 alkyl group and includes methyl, ethyl, propyl, isopropyl, butyl, t-butyl, 2-butyl, pentyl, hexyl, and the like. Preferable lower alkyl groups are C1-C4 alkyl, and more preferable lower alkyl groups are C1-C3 alkyl. Examples of cycloalkyl groups are moieties having 3 to 10, preferably 3 to 7 carbon atoms including cyclopropyl, cyclopentyl and cyclohexyl groups.

"Aryl" means a monovalent, monocyclic or bicyclic, aromatic carbocyclic or heterocyclic radical, preferably a 6-10 member aromatic ring system. Preferred aryl groups include, but are not limited to, phenyl, naphthyl, tolyl, xylyl, thienyl, furyl, indolyl, pyrrolyl, pyridinyl, oxy-pyridinyl, pyrazinyl, oxazolyl, thiaxolyl, quinolinyl, pyrimidinyl, imidazole and tetrazolyl. Aryl groups can be optionally mono-, di- or tri-substituted by, for example, lower alkyl, cycloalkyl, e.g., cyclopropyl, trihalo-lower alkyl, e.g., trifluoromethyl, hydroxyl, alkoxy, especially lower alkoxy, mono or dihydroxyl-substituted alkoxy, acetamido, methoxyacetamido, dimethylaminoacetamido, halogen, e.g., fluoro, chloro, or bromo, aniline derivatives, amide derivatives of the aniline derivatives and methanesulfonyl. When two or more substituents are present on an aryl or heteroaryl ring they may also be present in the form of a fused ring. Such fused rings include, but are not limited to, 3,4-methylenedioxyphenyl and 3,4-ethylenedioxyphenyl.

"Heteroatom" means an atom selected from N, O and S, unless otherwise specified.

"Heterocyclyl" means a group having four to six carbon atoms and at least one heteroatom.

"Alkoxy or lower alkoxy" refers to any of the above lower alkyl groups attached to an oxygen atom. Typical lower alkoxy groups include methoxy, ethoxy, isopropoxy or propoxy, butyloxy, cyclopropyl methoxy, and the like.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds.

"Pharmaceutically acceptable," such as pharmaceutically acceptable carrier, excipient, etc., means pharmacologically acceptable and substantially non-toxic to the subject to which the particular compound is administered.

"Substituted," as in substituted aryl or heteroaryl, means that the substitution can occur at one or more positions and, unless otherwise indicated, that the substituents at each substitution site are independently selected from the specified options.

"Therapeutically effective amount or effective amount" means an amount of at least one designated compound that significantly inhibits proliferation and/or prevents differentiation of a human tumor cell, including human tumor cell lines.

The compounds of the present invention are useful in the treatment or control of cell proliferative disorders, particularly oncological disorders. These compounds and formulations containing said compounds may be useful in the treatment or control of solid tumors, such as, for example, breast, colon, lung and prostate tumors and other oncological diseases such as non-Hodgkin's lymphomas.

The compounds of formula I as well as their salts have at least one asymmetric carbon atom and therefore may be present as mixtures of different stereoisomers. The various isomers can be isolated by known separation methods, e.g., chromatography.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, water, polyols, saccharose, invert sugar, glucose, etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

General methods for the preparation of compounds of Formula I are given in scheme 1. Briefly, the process involves the formation of 4-substituted-2-chloro-5-nitropyrimidine (IV) by the coupling of a substituted beta-amino acid ester (III) with 2,4-dichloro-5-nitropyrimidine, which is then reduced to the corresponding amino derivative (V) using standard reduction conditions for the conversion of a nitro group to an amine, such as iron powder in acetic acid, tin (II) chloride in acetic acid or hydrogen over a supported catalyst, such as palladium or Raney nickel, and then cyclized to the pyrimidodiazepinone (VI) in the presence or absence of acid catalysts such as acetic acid or mineral acids, such as hydrochloric or sulfuric acid. Pyrimidodiazepinone (VI) is then alkylated with standard alkylating reagents such alkyl halides in the presence of a base, to form pyrimidodiazepinone (VII). The reaction of substituted amines with pyrimidodiazepinone (VII) provides the compounds of formula I. Further modification of the R1 group in I can be carried out to provide additional derivatives of formula I.

A) Preparation of Pyrimidodiazepinones scheme 1

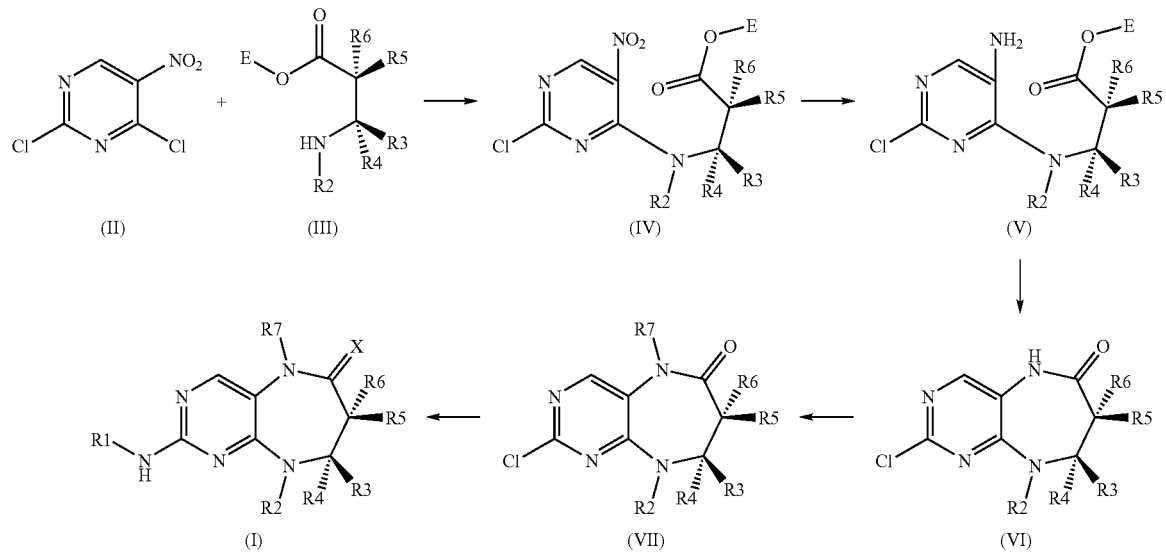

B) Preparation of Beta-Amino Acid Ester Intermediates

The beta-amino acid ester intermediates (III) which are not commercially available or have not been previously described in the literature were prepared by previously disclosed methods which are outlined below.

Method 1: amine addition to acrylate derivatives.

Adapted from the method of Biggs et al.

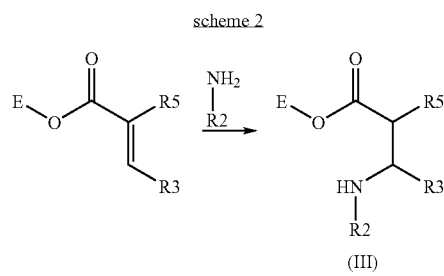

Method 2: reductive amination of beta amino acid esters.

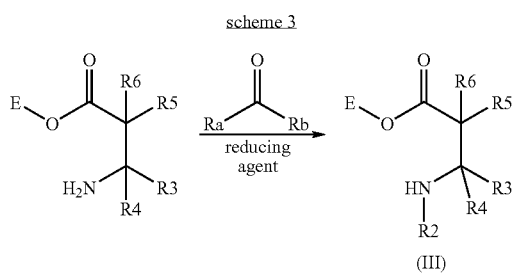

Method 3: reductive amination of beta-keto esters.

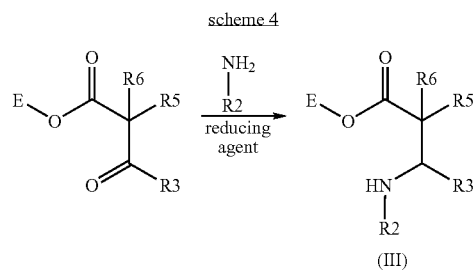

Method 4: alpha alkylation of beta amino acid esters.

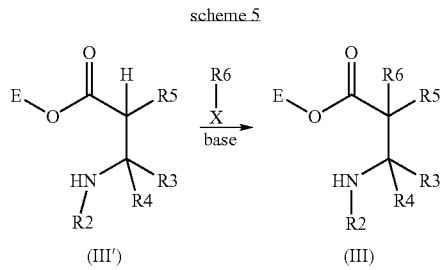

Method 5: arylation of beta amino acid esters using aryl iodides in the presence of copper.

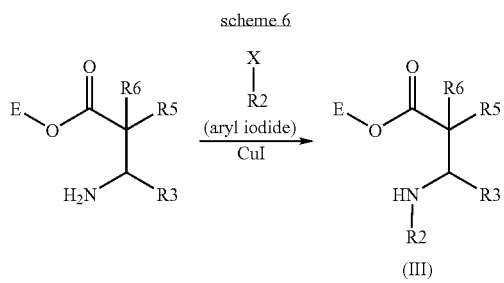

Method 6: reduction of alpha-cyano amino acid esters.

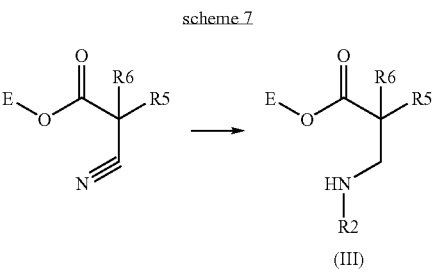

Method 7: reaction of benzotriazole-1-methanamines with nucleophiles

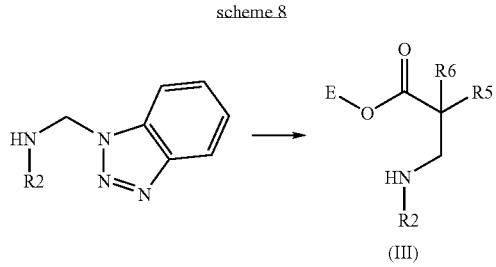

In the examples described, temperatures are indicated in degrees C. For mass spectral data, values are given as the $MH^+/Z$ ion obtained in the positive mode, electrospray measured on a Micromass Platform II mass spectrometer. Unless indicated otherwise, reactions were generally run under an inert atmosphere (argon or nitrogen). Unless indicated otherwise, chromatographic separations were carried using silica gel, solvent mixtures, where indicated are provided as ratio of volumes. Chiral separations were carried out using supercritical fluid chromatography (Berger Instrument Multi-gram II) using a 3.0×25 cm Daicel Chiralpak OD column, eluting with carbon dioxide plus modifier solvent (indicated in parentheses).

Preparation of Intermediates
Beta-Amino Acid Esters (III)

Method 1

3-Cyclopentylamino-propanoic acid methyl ester

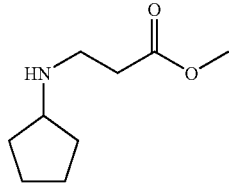

A mixture of 59.605 g (0.70 mole) cyclopentylamine (Aldrich), 72.299 g (0.84 mole) of methyl acrylate (Aldrich) and 250 mL of methanol was heated at reflux under an argon atmosphere for 14 hours, then ca 200 mL of solvent was distilled out at atmospheric pressure. The residue was distilled under vacuum (12 mm Hg, bp 112-114 degrees) to give 77.616 g (64%) of 3-cyclopentylamino-propanoic acid methyl ester.

(rac)-3-Cyclopentylamino-2-methyl-propanoic acid methyl ester

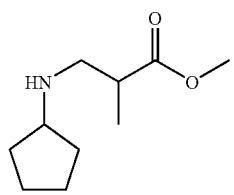

A mixture of 42.575 g (0.50 mole) of cyclopentylamine (Aldrich), 60.072 g (0.60 mole) of methyl methacrylate (Aldrich) and 250 mL of methanol was heated at reflux under an argon atmosphere for 29 hours, then ca 250 mL of solvent was distilled out at atmospheric pressure. The residue was distilled under vacuum (11 mm Hg, bp 114-116 degrees) to give 76.570 g (82%) of (rac)-3-cyclopentylamino-2-methyl-propanoic acid methyl ester.

(rac)-3-Cyclobutylamino-2-methyl-propanoic acid methyl ester

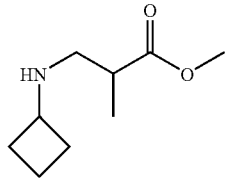

A solution of 10.72 g (0.10 mole) of cyclobutylamine, 12.01 g (0.12 mole) of methyl methacrylate and 50 mL of methanol was heated at 90 degrees for 20 hours in a pressure bottle. After cooling the mixture was concentrated, then distilled under vacuum to give 13.77 g of (rac)-3-cyclobutylamino-2-methyl-propanoic acid methyl ester as colorless oil. b.p. 70-75 degrees at 0.5 mm Hg.

(rac)-2-Methyl-3-(3-methyl-butylamino)-propanoic acid methyl ester

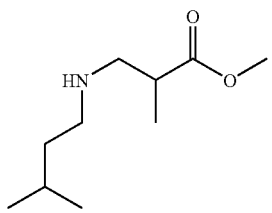

A solution of 8.72 g (0.10 mole) of isoamylamine, 12.01 g (0.12 mole) of methyl methacrylate and 50 mL of methanol was heated at reflux under an argon atmosphere for 22 hours. After cooling the mixture was concentrated, then distilled under vacuum to give 14.31 g of (rac)-2-methyl-3-(3-methyl-butylamino)-propanoic acid methyl ester as colorless oil. b.p. 73-75 degrees, 2 mm Hg.

(rac)-2-Methyl-3-(2-propenylamino)-propanoic acid methyl ester

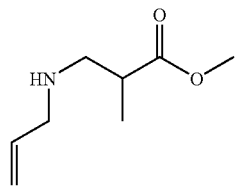

A solution of 11.42 g (0.20 mole) of allylamine, 24.03 g (0.24 mole) of methyl methacrylate and 100 mL of methanol in a pressure bottle, was heated at 90 degrees for 43 hours. After cooling the mixture was concentrated, then vacuum distilled under vaccuum to give 24.55 g (rac)-2-methyl-3-(2-propenylamino)-propanoic acid methyl ester as colorless oil. b.p. 70 degrees, 5 mm Hg.

(rac)-3-[(Cyclopentylamino)methyl]dihydro-2(3H)-furanone

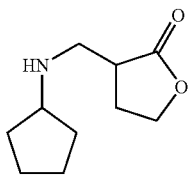

A mixture of 4.44 g (0.0521 mole) of cyclopentylamine and 5.12 g (0.0521 mole) of dihydro-3-methylene-(3H)-furanone was stirred at room temperature for 40 minutes and then distilled under vacuum to give 8.41 g of (rac)-3-[(cyclopentylamino)methyl]dihydro-2(3H)-furanone, b.p. 120-128 degrees, 0.3 mm Hg.

Method 2

3-Cyclopentylamino-propanoic acid ethyl ester

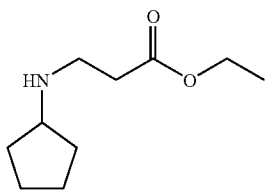

To a solution of 11.5 g (0.075 mole) of beta-alanine ethyl ester hydrochloride and 6.3 g (0.073 mole) of cyclopentanone in 200 mL of dichloromethane was added 6.5 g (0.082 mole)

of sodium acetate and 22.5 g (0.107 mole) of sodium triacetoxyborohydride. The mixture was stirred 24 hours and then quenched by the addition of 200 mL of saturated sodium bicarbonate solution. After 20 minutes, the organic layer was separated and the aqueous layer was extracted twice with dichloromethane. The combined dichloromethane layers were dried over anhydrous magnesium sulfate, filtered, and concentrated under reduced pressure to provide 12.0 g of 3-cyclopentylamino-propanoic acid ethyl ester, which was used without further purification.

(rac)-3-Cyclopentylamino-2-methyl-propanoic acid ethyl ester

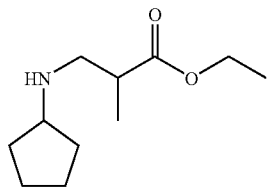

To a mixture of (rac)-3-amino-2-methylpropanoic acid ethyl ester hydrochloride (prepared from 3.09 g, 0.030 mole of (rac)-3-amino-2-methylpropanoic acid, thionyl chloride and ethanol) and 2.8 mL (0.0315 mole) of cyclopentanone and 100 mL of dichloromethane was added 5.4 g (0.066 mole) of sodium acetate and 9.54 g (0.045 mole) of sodium triacetoxyborohydride. The mixture was stirred at ambient temperature for 3 hrs and then quenched by the addition of 50 mL of 10% sodium bicarbonate solution. The aqueous layer was extracted with twice with 100 mL of dichloromethane, and the combined dichloromethane layers dried over anhydrous magnesium sulfate, filtered and concentrated under reduced pressure. The residue was purified by silica gel chromatography, eluting with dichloromethane-methanol (100:0-95:5 gradient) to give 2.86 g of (rac)-3-cyclopentylamino-2-methyl-propanoic acid ethyl ester.

(rac)-3-Cyclopentylamino-butanoic acid ethyl ester

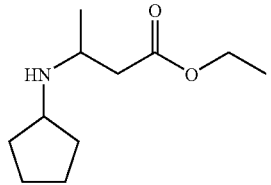

To a solution of 1.5 g (0.010 mole) of (rac)-3-amino-butanoic acid ethyl ester (90% technical grade) and 0.93 mL (0.0105 mole) of cyclopentanone in 50 mL of dichloromethane was added 1.8 g (0.022 mole) of sodium acetate and 3.18 g (0.015 mole) of sodium triacetoxyborohydride. The mixture was stirred overnight at room temperature and then 50 mL of 10% sodium bicarbonate solution was added. The aqueous layer was extracted twice with 50 mL of dichloromethane and then combined dichloromethane layers were dried over anhydrous magnesium sulfate, filtered and concentrated under reduced pressure. The residue was purified by silica gel chromatography, eluting with dichloromethane-methanol (100:0-95:5 gradient) to give 1.0 g of (rac)-3-cyclopentylamino-butanoic acid ethyl ester as a colorless oil.

(rac)-3-Cyclohexylamino-2-methyl-propanoic acid ethyl ester

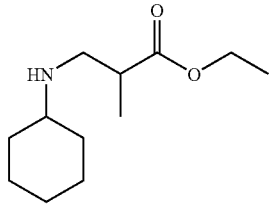

To a solution of 3.84 g (0.0229 mole) of (rac)-3-amino-2-methyl-propanoic acid ethyl ester hydrochloride, 2.25 g (0.0229 mole) of cyclohexanone (Aldrich) in 100 mL of dichloromethane was added 2.25 g (0.0275 mole) of anhydrous sodium acetate and 7.66 g (0.03435 mole) of sodium triacetoxyborohydride (Aldrich). The mixture was stirred at room temperature for 3 hours and then quenched by the addition of 50 mL of aqueous saturated sodium bicarbonate solution and 50 mL of water. After thorough mixing, the layers were separated and the aqueous layer was extracted twice with 100 mL of dichloromethane. The organic layers were washed with 100 mL of brine, combined, dried over anhydrous magnesium sulfate, filtered and concentrated. Purification of the residue by silica gel chromatography, eluting with dichloromethane-methanol (95:5-90:10) gave 4.4 g of (rac)-3-cyclohexylamino-2-methyl-propanoic acid ethyl ester acetic acid salt and 1.33 g of (rac)-3-cyclohexyl-amino-2-methyl-propanoic acid ethyl ester.

3-Cyclobutylamino-propanoic acid ethyl ester

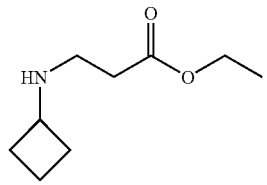

To a solution of 10.4 g (0.067 mole) of beta-alanine ethyl ester hydrochloride and 5.0 g (0.071 mole) of cyclobutanone in 200 mL of dichloromethane was added 6.1 g (0.074 mole) of sodium acetate and 21.5 g (0.101 mole) of sodium triacetoxyborohydride. The mixture was stirred at room temperature for 24 hours and then quenched by the addition of 200 mL of aqueous sodium bicarbonate. After 20 minutes, the organic layer was separated and the aqueous layer was extracted with twice with 50 mL of dichloromethane. The combined organic layers dried over anhydrous magnesium sulfate, filtered, and concentrated. Purification of the residue by silica gel chromatography, eluting with hexanes-ethyl acetate (20:80) gave 2.1 g of 3-cyclobutylamino-propanoic acid ethyl ester.

(rac)-2-Methyl-3-(tetrahydropyran-4-ylamino)-propanoic acid ethyl ester

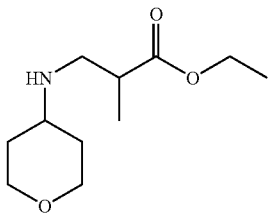

To a solution of 4.904 g (0.020 mole) of (rac)-3-amino-2-methyl-propanoic acid ethyl ester trifluoroacetate in 100 mL of dichloromethane was added 2.0 g (0.02 mole) of tetrahydro-4H-pyran-4-one, 3.28 g (0.040 mole) of sodium acetate and 6.70 g (0.030 mole) of sodium triacetoxyborohydride. The mixture was stirred at room temperature for 16 hours and then 100 mL of saturated aqueous sodium bicarbonate solution (100 mL) was added. After stirring for another 30 minutes, the layers were separated. The aqueous layer was extracted twice with 100 mL of dichloromethane. The organic layers were washed with 100 mL of brine, combined, dried over anhydrous magnesium sulfate, filtered, and concentrated. The residue was distilled under vacuum to give 2.05 g of (rac)-2-methyl-3-(tetrahydro-pyran-4-ylamino)-propanoic acid ethyl ester as colorless oil. b.p. 135° C., 8 mm Hg.

(rac)-3-(2-Methyl-cyclopentylamino)-propanoic acid ethyl ester

To a solution of 9.2 g (0.060 mole) of 3-amino-propanoic acid ethyl ester HCl salt and 5.9 g (0.060 mole) of (rac)-2-methyl-cyclopentanone in 300 mL of dichloromethane was added 10.8 g (0.132 mole) of sodium acetate and 19.1 g (0.090 sodium triacetoxyborohydride (19.1 g, 90 mmol). The mixture was stirred at ambient temperature overnight and then quenched by the addition of 100 mL of 10% sodium bicarbonate solution. The aqueous layer was extracted twice with 200 mL of dichloromethane, and the combined dichloromethane layers dried over anhydrous magnesium sulfate. The mixture was filtered, concentrated under reduced pressure, and distilled at 0.0015 mm Hg (bp 70 degrees), to give 9.8 g of (rac)-3-(2-methyl-cyclopentylamino)-propanoic acid ethyl ester.

(rac)-3-(3-Methyl-cyclopentylamino)-propanoic acid ethyl ester

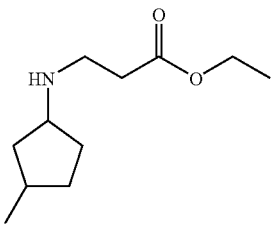

To a solution of 9.2 g (0.060 mole) of 3-amino-propanoic acid ethyl ester HCl salt and 5.9 g (0.060 mole) of (rac)-2-methyl-cyclopentanone in 300 mL of dichloromethane was added 10.8 g (0.132 mole) of sodium acetate and 19.1 g (0.090 sodium triacetoxyborohydride (19.1 g, 90 mmol). The mixture was stirred at ambient temperature overnight and then quenched by the addition of 100 mL of 10% sodium bicarbonate solution. The aqueous layer was extracted twice with 200 mL of dichloromethane, and the combined dichloromethane layers dried over anhydrous magnesium sulfate. The mixture was filtered, concentrated under reduced pressure, and distilled at 0.0015 mm Hg (bp 75 degrees), to give 9.6 g of (rac)-3-(3-methyl-cyclopentylamino)-propanoic acid ethyl ester.

(rac)-3-(2,2-Dimethyl-cyclopentylamino)-propanoic acid ethyl ester

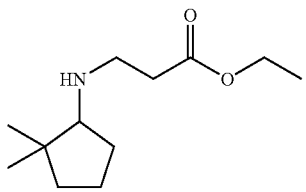

To a solution of 13.8 g (0.090 mole) of 3-amino-propanoic acid ethyl ester HCl salt and 10.0 g (0.090 mole) of 2,2-dimethyl-cyclopentanone in 500 mL of dichloromethane was added 16.4 g (0.198 mole) of sodium acetate and 28.6 g (0.135 mole) of sodium triacetoxyborohydride. The mixture was stirred at ambient temperature overnight and then quenched by the addition of 100 mL of 10% sodium bicarbonate solution. The aqueous layer was extracted twice with 300 mL of dichloromethane, and the combined dichloromethane layers dried over anhydrous magnesium sulfate. The mixture was filtered, concentrated under reduced pressure, and distilled at 0.0015 mm Hg (bp 75 degrees), to give 15.4 g of (rac)-3-(2,2-dimethyl-cyclopentylamino)-propanoic acid ethyl ester.

Method 3

(rac)-3-Cyclopentylamino-2-methyl-butanoic acid ethyl ester

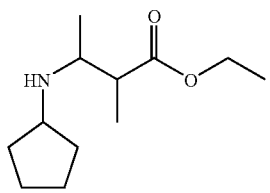

To a solution of 2.1 g (0.014 mole) of 2-methyl-3-oxo-butanoic acid ethyl ester and 40 mL of dichloroethane was added 1.37 g (0.016 mole) of cyclopentylamine. The mixture was stirred for 1.5 hours, then 4.63 g (0.020 mole) of sodium triacetoxyborohydride and 0.84 g (0.014 mole) of acetic acid were added. The mixture was stirred at room temperature for 24 hours and then quenched by the addition of 50 mL of saturated aqueous sodium bicarbonate. After 20 minutes, the organic layer was separated and the aqueous layer was extracted twice with 30 mL of dichloromethane. The combined organic layers were dried over anhydrous magnesium sulfate, filtered, and concentrated to afford the crude product as yellow oil. Purification of the residue by silica gel chromatography, eluting with hexanes-ethyl acetate (30:70) gave 1.5 g of (rac)-3-cyclopentylamino-2-methyl-butanoic acid ethyl ester.

(rac)-3-Cyclopropylamino-2-methylbutanoic acid ethyl ester

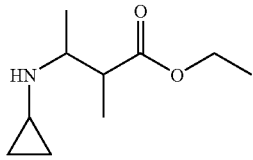

To a solution of 2.3 g (0.016 mole) of 2-methyl-3-oxobutanoic acid ethyl ester in 50 mL of dichloroethane was added 1.00 g (0.016 mole) of cyclopropylamine. The mixture was stirred for 1.5 hours and then 5.1 g (0.023 mole) of sodium triacetoxyborohydride and 0.96 g (0.016 mole) of acetic acid were added. The mixture was stirred at room temperature for 24 hours and then quenched by the addition of 50 mL of saturated aqueous sodium bicarbonate. The mixture was stirred for 20 minutes. The organic layer was separated and the aqueous layer was extracted with twice with 30 mL of dichloromethane. The combined organic layers were dried over anhydrous magnesium sulfate, filtered, and concentrated. Purification of the residue by silica gel chromatography, eluting with hexanes-ethyl acetate (30:70) gave 1.5 g of (rac)-3-cyclopropylamino-2-methyl-butanoic acid ethyl ester.

(rac)-2-Cyclopentylamino-cyclopentanecarboxylic acid, methyl ester

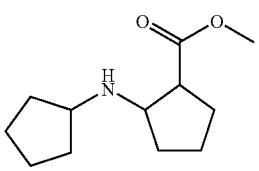

To a ice cooled solution of 13.36 g (0.066 mole) of 2-cyclopentylamino-1-cyclopentenecarboxylic acid, methyl ester (prepared from 10.0 g (0.116 mole) of cyclopentylamine and 18.46 g (0.122 mole) of 2-oxocyclopentanecarboxylic acid methyl ester in 200 mL of dichloromethane, in the presence of 38.9 g (0.174 mole) of sodium triacetoxyborohydride and 14.31 g (0.174 mole) of sodium acetate) in 210 mL of acetonitrile and 110 mL of acetic acid was added 44.32 g (0.198 mole) of sodium triacetoxyborohydride. After 10 minutes, the cooling bath was removed and the mixture stirred at room temperature overnight. Solvents were removed under reduced pressure and the residue partitioned between ethyl acetate and water containing sufficient sodium carbonate to make the mixture basic (ca pH 11). The water layer was extracted twice with ethyl acetate and the combined ethyl acetate layers washed successively with water, then brine, dried over anhydrous magnesium sulfate, filtered and concentrated under reduced pressure to give 10.2 g of (rac)-2-cyclopentylamino-cyclopentanecarboxylic acid, methyl ester, which was used without further purification in subsequent steps.

3-Cyclopentylamino-2,2-dimethyl-propanoic acid methyl ester

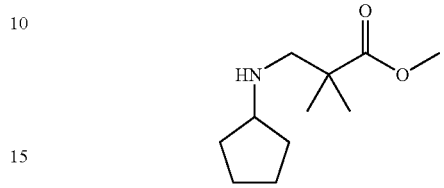

To a solution of 21.98 g (0.167 mole) of 3-amino-2,2-dimethyl-propanoic acid methyl ester (from method 6) in 500 mL of dichloromethane cooled to 0 degrees, was added 14.1 g (0.167 mole) of cyclopentanone, 16.0 g (0.181 mole) of sodium acetate and 52.0 g (0.025 mole) of sodium triacetoxyborohydride. The mixture stirred at room temp. for 22 hours, and then quenched by the addition of 500 mL of saturated sodium bicarbonate solution. The mixture was stirred for 1 hour and then extracted twice 400 mL of dichloromethane. The combined organic layers were dried over anhydrous sodium sulfate, filtered and concentrated under reduced pressure to give 31.8 g of 3-cyclopentylamino-2,2-dimethyl-propanoic acid methyl ester which was used without further purification.

1-Cyclopentylaminomethyl-cyclopropanecarboxylic acid methyl ester

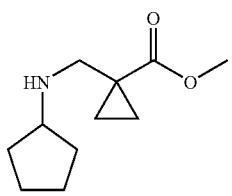

Cyclopentylaminomethyl-cyclopropanecarboxylic acid methyl ester was prepared from 1-aminomethyl-cyclopropanecarboxylic acid methyl ester following the method similar to the preparation of 3-cyclopentylamino-2,2-dimethyl-propanoic acid methyl ester above.

Method 4

(rac)-2-Cyclopentylaminomethyl-butanoic acid ethyl ester

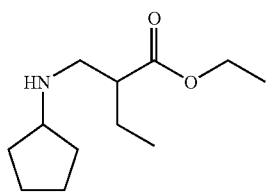

To a mixture of 1.0 g (0.0054 mole) of 3-cyclopentylamino-propanoic acid ethyl ester, 0.842 g (0.00542 mole) of iodoethane and 15 mL of dry tetrahydrofuran, at −78 degrees, was added 11.4 mL (0.0114 mole) of a 1M solution of lithium bis(trimethylsilyl)amide in hexanes over 5 minutes. The mixture was stirred for one hour at −78 degrees, then the cooling bath was removed and the mixture stirred overnight at room temperature, and then poured into ice water containing 5 mL of 1M sodium hydroxide solution. The mixture was extracted with ether, and the ether extract washed with brine, dried over anhydrous magnesium sulfate, filtered and concentrated under reduced pressure to give 0.5125 g of (rac)-2-cyclopentylaminomethyl-butanoic acid ethyl ester, which was used without further purification in subsequent steps.

(rac)-2-Cyclopentylaminomethyl-pentanoic acid ethyl ester

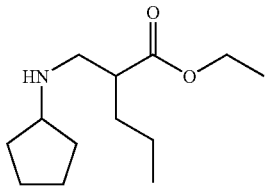

To a mixture of 2.0 g (0.0108 mole) of 3-cyclopentylamino-propanoic acid ethyl ester and 10 mL of anhydrous tetrahydrofuran, at −78 degrees, was added 24.0 mL (0.0236 mole) of lithium bis(trimethylsilyl)amide. The mixture was stirred for 1 hour and then a solution of 2.0 g (0.0119 mole) of iodopropane in 2.0 mL of tetrahydrofuran was added slowly. The mixture was stirred at room temperature for 24 hours and then quenched by the addition of water. The mixture was concentrated under reduced pressure and then extracted three times with 50 mL of ethyl acetate. The combined extracts were dried over anhydrous magnesium sulfate, filtered and concentrated under reduced pressure to give 1.2 g of (rac)-2-cyclopentylaminomethyl-pentanoic acid ethyl ester, which was used without further purification in subsequent steps.

Method 5

(rac)-2-Methyl-3-phenylamino-propanoic acid ethyl ester

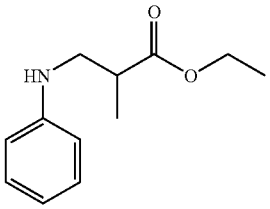

To a solution of 4.904 g (0.020 mole) of (rac)-3-amino-2-methyl-propanoic acid ethyl ester trifluoroacetate in 30 mL of dimethylsulfoxide was added 4.08 g (0.020 mole) of iodobenzene, 0.46 g (0.004 mole) of L-proline, 0.38 g (0.002 mole) of copper (I) iodide and 19.57 g (0.060 mole) of cesium carbonate. Argon was bubbled through the solution for 15 minutes. The mixture was then heated at 80 degrees for 16 hours. After cooling, the mixture was partitioned between ethyl acetate (2×300 mL) and water (3×300 mL). The organic layers were washed with 300 mL of brine, combined, dried over anhydrous magnesium sulfate, filtered, and concentrated. Purification of the residue by silica gel chromatography, eluting with dichloromethane-hexanes (80:20) and then dichloromethane gave 1.70 g of (rac)-2-methyl-3-phenylamino-propionic acid ethyl ester as colorless oil that darkened on standing.

Method 6

3-Amino-2,2-dimethyl-propanoic acid methyl ester

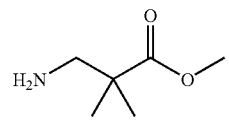

A mixture of 10 g of Raney-nickel 2800 was transferred to a 500 mL hydrogenation vessel and washed three times with 40 mL of methanol. Then, 180 mL of methanol and 25.0 g (0.177 mole) of 2-cyano-2-methylpropanoic acid ethyl ester was added and the mixture agitated on a Paar hydrogenator under a 50 psi atmosphere of hydrogen for 24 hours. The mixture was filtered through Celite, washing the filter pad with methanol, and then concentrated under reduced pressure to give 21.98 g of 3-amino-2,2-dimethyl-propanoic acid methyl ester, which was used without further purification.

1-Aminomethyl-cyclopropanecarboxylic acid methyl ester

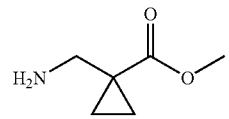

1-aminomethyl-cyclopropanecarboxylic acid methyl ester was prepared by hydrogenation of 1-cyano-cyclopropanecarboxylic acid ethyl ester, by the method similar to the preparation of 3-amino-2,2-dimethyl-propanoic acid methyl ester, above.

Method 7

3-Cyclopentylamino-2,2-difluoro-propanoic acid ethyl ester

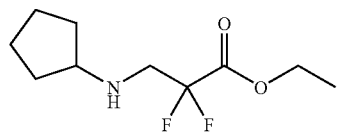

step a

To a mixture of 2.4 g (0.02 mole) of benzotriazole and 1.98 mL (0.02 mole) of cyclopentylamine in 100 mL of ether was added dropwise 1.5 mL (0.02 mole) of 37% aqueous formaldehyde. The reaction mixture was stirred at room temperature for 6 hours. The solution was dried over calcium chloride, filtered and concentrated under reduced pressure. The solid was washed with hexane and dried to give benzotriazol-1-ylmethyl-cyclopentyl-amine as a white solid.

step b

To a suspension of 4.3 g (0.066 g-atom) of zinc powder in 40 mL of tetrahydrofuran was added 4.1 mL (0.032 mole) of chlorotrimethylsilane. After stirring for 10 minutes, 6.6 g (0.032 mole) of ethyl bromodifluoroacetate was added dropwise at room temperature. After 10 minutes, a solution of 7.0 g (0.032 mole) of benzotriazol-1-ylmethyl-cyclopentyl-amine in tetrahydrofuran was added dropwise. The reaction mixture was stirred at room temperature for 3 hours and then quenched by the addition of saturated aqueous sodium carbonate. The mixture was filtered through Celite. The filtrate was extracted twice with ether. The combined organic layers were dried over anhydrous sodium sulfate, filtered, and concentrated under reduced pressure. The residue was distilled under vacuum to give 2.77 g of 3-cyclopentylamino-2,2-difluoro-propanoic acid ethyl ester as a colorless oil. bp 75-82 degrees at 10 mm Hg.

The following Examples serve to illustrate the present invention in more detail. They are, however, not intended to limit its scope in any manner. Where Roman numeral I is used in combination with an Arabic numeral, e.g., I-1, it refers to the compounds listed in Table 1. Roman numerals greater than I in combination with an Arabic numeral denote intermediate compounds, and refer back to the general intermediate formulas in the schemes set out above. For example, the compound denoted IV-1 in Example 1 is the first instance of an intermediate compound corresponding to general formula IV in scheme 1 above.

EXAMPLE 1

(rac)-4-(9-Cyclopentyl-5,7-dimethyl-6-oxo-6,7,8,9-tetrahydro-5H-pyrimido[4,5-b][1,4]diazepin-2-yl amino)-3-methoxy-benzoic acid (I-1)

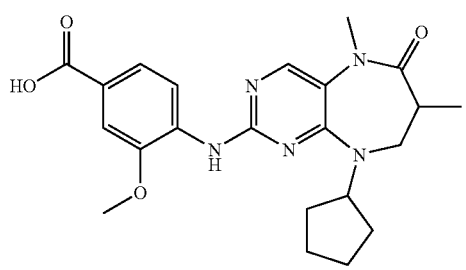

step a

A solution of 1.99 g (0.010 mole) of (rac)-3-cyclopentylamino-2-methyl-propanoic acid ethyl ester in 25 mL of water was added dropwise to a solution of 1.94 g (0.010 mole) of 2,4-dichloro-5-nitro-pyrimidine in 25 mL of ethyl ether. At 0 degrees, 2.0 g (0.020 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-80:20) gave 3.0 g of (rac)-3-[(2-chloro-5-nitro-pyrimidin-4-yl)-cyclopentyl-amino]-butanoic acid ethyl ester (IV-1)

step b

To a solution of 1.07 g (0.030 mole) of (rac)-3-[(2-chloro-5-nitro-pyrimidin-4-yl)-cyclopentyl-amino]-butanoic acid ethyl ester in 20 mL of acetic acid was added 1.0 g (0.018 g-atom) of iron powder. The mixture was heated to 80 degrees for 2 hrs and then filtered while hot. 50 mL of water and 50 mL of ethyl acetate were added and the mixture was stirred for 10 minutes and then filtered. The layers were separated. The organic layer was washed with ammonium hydroxide and water, dried over anhydrous magnesium sulfate, filtered and concentrated under reduced pressure. Purification by silica gel chromatography, eluting with dichloromethane-methanol (100:0-96:4) gave 0.584 g of (rac)-2-chloro-9-cyclopentyl-7-methyl-5,7,8,9-tetrahydro-pyrimido[4,5-b][1,4]diazepin-6-one (VI-1) as a white solid.

step c

To a mixture of 0.056 g (0.0002 mole) of (rac)-2-chloro-9-cyclopentyl-7-methyl-5,7,8,9-tetrahydro-pyrimido[4,5-b][1,4]diazepin-6-one, 0.5 mL of N,N-dimethylacetamide and 0.018 mL (0.0003 mole) of iodomethane was added 0.012 g (0.0003 mole) of 60% sodium hydride in oil at 0 degrees. The mixture was stirred at ambient temperature for 1 hour, then 10 mL of water was added. The precipitate collected by filtration to give 0.049 g of (rac)-2-chloro-9-cyclopentyl-5,7-dimethyl-5,7,8,9-tetrahydro-pyrimido[4,5-b][1,4]diazepin-6-one (VI-1) as an yellow solid.

step d

A mixture of 0.030 g (0.0001 mole) of (rac)-2-chloro-9-cyclopentyl-5,7-dimethyl-5,7,8,9-tetrahydro-pyrimido[4,5-b][1,4]diazepin-6-one, 0.017 g (0.0001 mole) of 4-amino-3-methoxy-benzoic acid, 0.5 mL of ethanol, 2 mL of water, and 2 drops of hydrochloric acid was heated to 100 degrees overnight. Upon cooling, a precipitate formed which was collected by filtration to give 0.028 g of (rac)-4-(9-cyclopentyl-5,7-dimethyl-6-oxo-6,7,8,9-tetrahydro-5H-pyrimido[4,5-b][1,4]diazepin-2-yl amino)-3-methoxy-benzoic acid (I-1) as an off-white solid.

EXAMPLE 2

(rac)-4-(9-Cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-2)

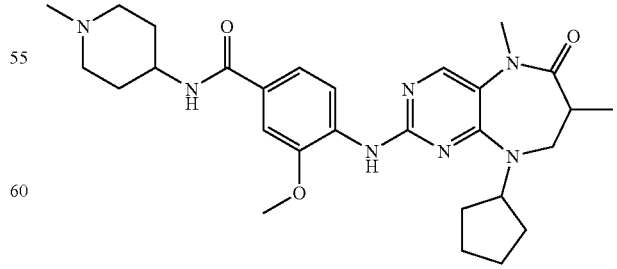

A mixture of 0.042 g (0.0001 mole) of (rac)-4-(9-cyclopentyl-5,7-dimethyl-6-oxo-6,7,8,9-tetrahydro-5H-pyrimido[4,5-b][1,4]diazepin-2-yl amino)-3-methoxy-benzoic acid (I-1), 0.042 g (0.00011 mole) of 1-[bis(dimethylamino)methylene]-1H-1,2,3-triazolo[4,5-b]pyridinium-3-oxide hexafluorophosphate, 0.026 mL (0.00015 mole) of ethyldiisopropyl amine and 1.0 mL of dimethylformamide was stirred for 5 minutes and then 0.017 g (0.00015 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse-phase silica gel chromatography, eluting with an acetonitrile-water gradient (20:80-100:0) to give 0.038 g of (rac)-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-2) as a white solid.

EXAMPLE 3

(rac)-4-(9-Cyclopentyl-5,7-dimethyl-6-oxo-6,7,8,9-tetrahydro-5H-pyrimido[4,5-b][1,4]diazepin-2-yl amino)-3-methoxy-benzoic acid (I-1)

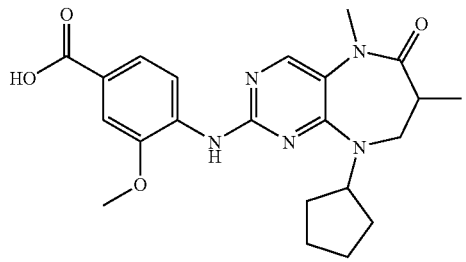

step a

Under an argon atmosphere, a solution of 26.86 g (0.145 mole) of (rac)-3-cyclopentylamino-2-methyl-propanoic acid methyl ester in 25 mL of ethyl acetate was added over 5 minutes to a cooled (5 degrees) and stirring mixture of 28.13 g (0.145 mole) of 2,4-dichloro-5-nitro-pyrimidine, 48.72 g (0.58 mole) of sodium bicarbonate and 300 mL of ethyl acetate. The cooling bath was removed and the mixture stirred for 17 hours at room temperature. Activated charcoal was added and after stirring briefly, the mixture was filtered through a pad of Celite, washing the filter pad with ethyl acetate. The mixture was concentrated under reduced pressure to give 50.37 g of (rac)-3-[(2-chloro-5-nitro-pyrimidin-4-yl)-cyclopentyl-amino]-2-methyl-propanoic acid methyl ester (IV-1) as a thick oil, which contained a small portion of a regioisomer. This material was used directly in the next step without further purification.

step b

A mixture of 40.64 g (0.119 mole) of (rac)-3-[(2-chloro-5-nitro-pyrimidin-4-yl)-cyclopentyl-amino]-2-methyl-propanoic acid methyl ester (IV-1) in 1500 mL of ethyl acetate and 14 g of 5% palladium on carbon catalyst was stirred under an atmosphere of hydrogen until hydrogen uptake was complete. The mixture was filtered through a pad of Celite, washing the filter pad with dichloromethane. Concentration under reduced pressure gave 35.2 g of (rac)-3-[(5-amino-2-chloro-pyrimidin-4-yl)-cyclopentyl-amino]-2-methyl-propanoic acid methyl ester (V-1), which also contained a small amount of (rac-)-2-chloro-9-cyclopentyl-7-methyl-5,7,8,9-tetrahydro-pyrimido[4,5-b][1,4]diazepin-6-one. This material was used directly in the next step without further purification.

step c

A mixture of 1500 mL of ethanol, 25 mL of acetic acid and 35.2 g of the (rac)-3-[(5-amino-2-chloro-pyrimidin-4-yl)-cyclopentyl-amino]-2-methyl-propanoic acid methyl ester (V-1) prepared in the previous step was heated at reflux overnight, and then concentrated under reduced pressure. The residue was taken up in dichloromethane and washed successively with 10% sodium bicarbonate solution, and then water and dried over anhydrous sodium sulfate. The mixture was filtered and then concentrated under reduced pressure to give 31 g of the crude product. Trituration of the residue with ether, provided 20.7 g of (rac)-2-chloro-9-cyclopentyl-7-methyl-5,7,8,9-tetrahydro-pyrimido[4,5-b][1,4]diazepin-6-one (VI-1).

step d

To a solution of 46.72 g (0.166 mole) of (rac)-2-chloro-9-cyclopentyl-7-methyl-5,7,8,9-tetrahydro-pyrimido[4,5-b][1,4]diazepin-6-one in 1000 mL of dimethylformamide was added 81.32 g (0.25 mole) of cesium carbonate, followed by 70.88 g (0.499 mole) of methyl iodide. After stirring four hours, the mixture filtered and then concentrated under reduced pressure. The residue was taken up in ethyl acetate and washed four times with water, once with brine and dried over anhydrous sodium sulfate. The mixture was filtered and then concentrated under reduced pressure to give 45 g of (rac)-2-chloro-9-cyclopentyl-5,7-dimethyl-5,7,8,9-tetrahydro-pyrimido[4,5-b][1,4]diazepin-6-one (VII-1). This material was used subsequent steps without further purification.

step e

A mixture of 4.105 g (0.0139 mole) (rac)-2-chloro-9-cyclopentyl-5,7-dimethyl-5,7,8,9-tetrahydro-pyrimido[4,5-b][1,4]diazepin-6-one (VII-1), 2.794 g (0.0167 mole) of 4-amino-3-methoxybenzoic acid (Aldrich) and 300 mL of ethanol-water-hydrochloric acid (20:80:1) was heated at reflux for 18 hours, then cooled and concentrated under reduced pressure to give 6.980 g of crude (rac)-2-chloro-9-cyclopentyl-5,7-dimethyl-5,7,8,9-tetrahydro-pyrimido[4,5-b][1,4]diazepin-6-one (I-1) which was used without further purification in subsequent steps.

EXAMPLE 4

7R-4-(9-Cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-2a) and 7S-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-2b)

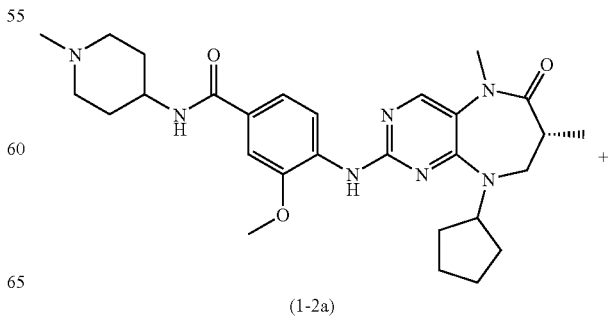

(I-2a)

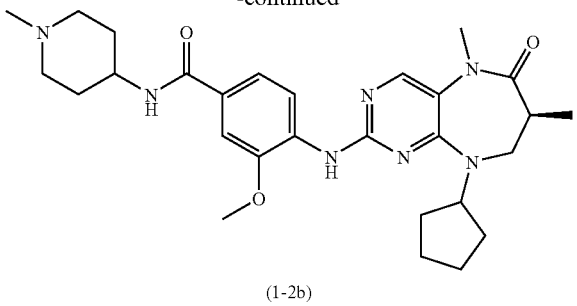

(I-2b)

To a mixture of the 6.980 g of crude (rac)-2-chloro-9-cyclopentyl-5,7-dimethyl-5,7,8,9-tetrahydro-pyrimido[4,5-b][1,4]diazepin-6-one (I-1) from example 3 and 100 mL of dimethylformamide was added 9.239 g (0.021 mole) of benzotriazol-1-yloxytris(dimethylamino) phosphonium hexafluorophosphate, followed by ca 7.764 mL (0.0557 mole) of triethylamine. The mixture was stirred under an argon atmosphere for 15 minutes, then 2.385 g (0.0209 mole) of 4-amino-1-methylpiperidine in 1 mL dimethylformamide was added. After 3 hours, the mixture was taken up in ethyl acetate and washed successively with 0.5 M sodium carbonate solution, water and then brine, and dried over anhydrous sodium sulfate. The mixture was filtered and then concentrated under reduced pressure to give 7.12 g of crude material. Purification by chromatography on silica gel, eluting with dichloromethane-methanol-ammonium hydroxide (92:8:0.3) gave 5.2054 g of (rac)-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-2).

The enantiomer separation was carried out using a 3.0×25 cm Daicel Chiralpak OD column, eluting with carbon dioxide+30% modifier (methanol-isopropylamine (998:2)), flow rate=70 mL/min., to give 2.054 g of 7R-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-2a) and 2.360 g of 7S-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-2b).

EXAMPLE 5

(rac)-4-(9-Cyclopentyl-5,8-dimethyl-6-oxo-6,7,8,9-tetrahydro-5H-pyrimido[4,5-b][1,4]diazepin-2-ylamino)-3-methoxy-benzoic acid (I-3)

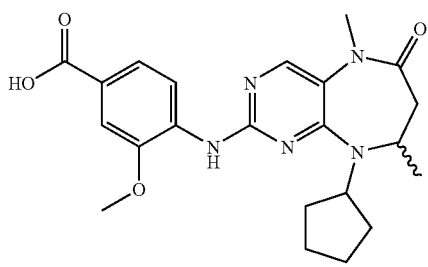

step a

A solution of 1.0 g (0.005 mole) of (rac)-3-cyclopentylamino-butanoic acid ethyl ester in 25 mL of water was added dropwise to a solution of 0.97 g (0.005 mole) of 2,4-dichloro-5-nitro-pyrimidine in 25 mL of ethyl ether. At 0 degrees, 1.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-80:20) gave 1.0 g of (rac)-3-[(2-chloro-5-nitro-pyrimidin-4-yl)-cyclopentyl-amino]-butanoic acid ethyl ester (IV-3)

step b

To a solution of 1.07 g (0.030 mole) of (rac)-3-[(2-chloro-5-nitro-pyrimidin-4-yl)-cyclopentyl-amino]-butanoic acid ethyl ester in 20 mL of acetic acid was added 1.0 g (0.018 g-atom) of iron powder. The mixture was heated to 80 degrees for 2 hrs and then filtered while hot. 50 mL of water and 50 mL of ethyl acetate were added and the mixture was stirred for 10 minutes and then filtered. The layers were separated. The organic layer was washed with ammonium hydroxide and water, dried over anhydrous magnesium sulfate, filtered and concentrated under reduced pressure. Purification by silica gel chromatography, eluting with dichloromethane-methanol (100:0-96:4) gave 0.45 g of (rac)-2-chloro-9-cyclopentyl-8-methyl-5,7,8,9-tetrahydro-pyrimido[4,5-b][1,4]diazepin-6-one (VI-3) as a white solid.

step c

To a mixture of 0.28 g (0.001 mole) of (rac)-2-chloro-9-cyclopentyl-8-methyl-5,7,8,9-tetrahydro-pyrimido[4,5-b][1,4]diazepin-6-one, 2 mL of N,N-dimethylacetamide and 0.093 mL (0.0015 mole) of iodomethane at 0 degrees was added 0.06 g (0.0015 mole) of 60% sodium hydride in oil. The mixture was stirred at ambient temperature for 1 hour, then 10 mL of water was added. The precipitate collected by filtration to give 0.278 g of (rac)-2-chloro-9-cyclopentyl-5,8-dimethyl-5,7,8,9-tetrahydro-pyrimido[4,5-b][1,4]diazepin-6-one (VII-3) as an yellow solid.

step d

A mixture of 0.059 g (0.0002 mole) of (rac)-2-chloro-9-cyclopentyl-5,8-dimethyl-5,7,8,9-tetrahydro-pyrimido[4,5-b][1,4]diazepin-6-one (VII-3), 0.033 g (0.0002 mole) of 4-amino-3-methoxy-benzoic acid, 0.5 mL of ethanol, 2 mL of water, and 2 drops of hydrochloric acid was heated to 100 degrees overnight. Upon cooling, a precipitate formed which was collected by filtration to give 0.062 g of (rac)-4-(9-cyclopentyl-5,8-dimethyl-6-oxo-6,7,8,9-tetrahydro-5H-pyrimido[4,5-b][1,4]diazepin-2-yl amino)-3-methoxy-benzoic acid (I-3) as an off-white solid.

EXAMPLE 6

(rac)-4-(9-Cyclopentyl-5,8-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-4)

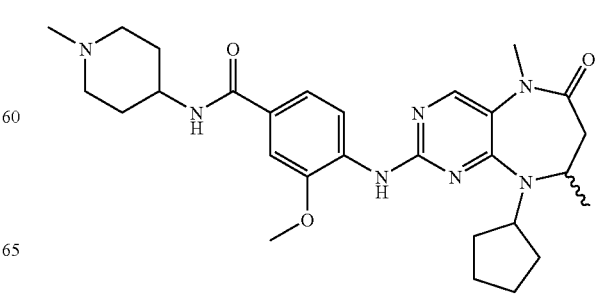

A mixture of 0.042 g (0.0001 mole) of (rac)-4-(9-cyclopentyl-5,8-dimethyl-6-oxo-6,7,8,9-tetrahydro-5H-pyrimido[4,5-b][1,4]diazepin-2-yl amino)-3-methoxy-benzoic acid (I-3), 0.042 g (0.00011 mole) of 1-[bis(dimethylamino)methylene]-1H-1,2,3-triazolo[4,5-b]pyridinium-3-oxide hexafluorophosphate, 0.026 mL (0.00015 mole) of ethyldiisopropyl amine and 1.0 mL of dimethylformamide was stirred for 5 minutes and then 0.017 g (0.00015 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.044 g of (rac)-4-(9-cyclopentyl-5,8-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-4) as a white solid.

EXAMPLE 7

(rac)-4-(9-Cyclopentyl-5,7-dimethyl-6-oxo-6,7,8,9-tetrahydro-5H-pyrimido[4,5-b][1,4]diazepin-2-ylamino)-benzoic acid (I-5)

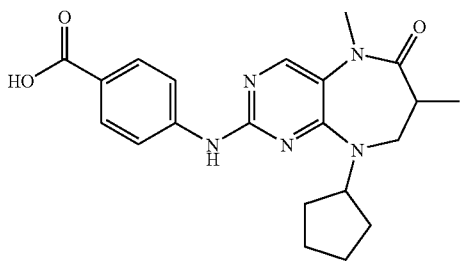

A mixture of 0.03 g (0.0001 mole) of (rac)-2-chloro-9-cyclopentyl-5,7-dimethyl-5,7,8,9-tetrahydro-pyrimido[4,5-b][1,4]diazepin-6-one, 0.014 g (0.0001 mole) of 4-aminobenzoic acid, 0.3 mL of ethanol, 0.8 mL of water, and 1 drop of hydrochloric acid was heated to 100 degrees overnight. Upon cooling, a precipitate formed which was collected by filtration to give 0.062 g of (rac)-4-(9-cyclopentyl-5,7-dimethyl-6-oxo-6,7,8,9-tetrahydro-5H-pyrimido[4,5-b][1,4]diazepin-2-yl amino)-benzoic acid (I-5) as an off-white solid.

EXAMPLE 8

(rac)-4-(9-Cyclopentyl-5,7-dimethyl-6-oxo-6,7,8,9-tetrahydro-5H-pyrimido[4,5-b][1,4]diazepin-2-ylamino)-N-(1-methyl-piperidin-4-yl)-benzamide (I-6)

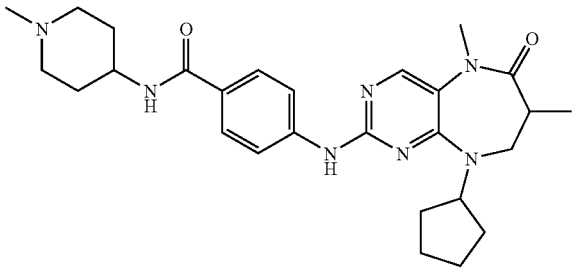

A mixture of 0.02 g (0.00005 mole) of (rac)-4-(9-cyclopentyl-5,7-dimethyl-6-oxo-6,7,8,9-tetrahydro-5H-pyrimido[4,5-b][1,4]diazepin-2-yl amino)-benzoic acid (I-5), 0.023 g (0.00006 mole) of 1-[bis(dimethylamino)methylene]-1H-1,2,3-triazolo[4,5-b]pyridinium-3-oxide hexafluorophosphate, 0.018 mL (0.0001 mole) of ethyldiisopropyl amine and 1.0 mL of dimethylformamide was stirred for 5 minutes and then 0.0085 g (0.000075 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.015 g of (rac)-4-(9-cyclopentyl-5,7-dimethyl-6-oxo-6,7,8,9-tetrahydro-5H-pyrimido[4,5-b][1,4]diazepin-2-ylamino)-N-(1-methyl-piperidin-4-yl)-benzamide (I-6) as a white solid.

EXAMPLE 9

(rac)-4-(9-Cyclopentyl-5,7-dimethyl-6-oxo-6,7,8,9-tetrahydro-5H-pyrimido[4,5-b][1,4]diazepin-2-ylamino)-3-methyl-benzoic acid (I-7)

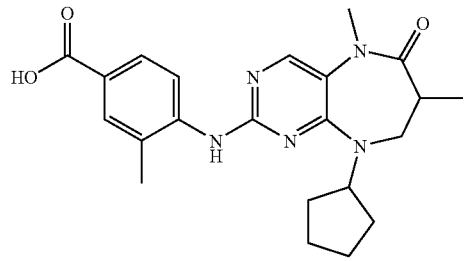

A mixture of 0.03 g (0.0001 mole) of (rac)-2-chloro-9-cyclopentyl-5,7-dimethyl-5,7,8,9-tetrahydro-pyrimido[4,5-b][1,4]diazepin-6-one, 0.015 g (0.0001 mole) of 4-amino-3-methylbenzoic acid, 0.3 mL of ethanol, 0.8 mL of water, and 1 drop of hydrochloric acid was heated to 100 degrees overnight. Upon cooling, a precipitate formed which was collected by filtration to give 0.020 g of (rac)-4-(9-cyclopentyl-5,7-dimethyl-6-oxo-6,7,8,9-tetrahydro-5H-pyrimido[4,5-b][1,4]diazepin-2-yl amino)-3-methyl-benzoic acid (I-7) as an off-white solid.

EXAMPLE 10

(rac)-4-(9-Cyclopentyl-5,7-dimethyl-6-oxo-6,7,8,9-tetrahydro-5H-pyrimido[4,5-b][1,4]diazepin-2-ylamino)-3-methyl-N-(1-methyl-piperidin-4-yl)-benzamide (I-8)

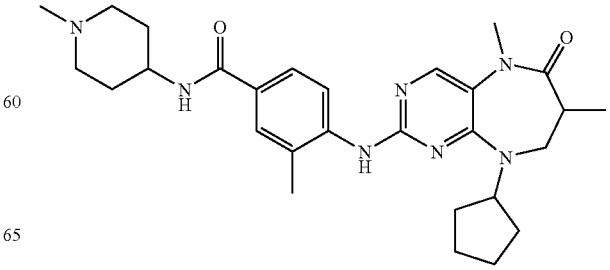

A mixture of 0.02 g (0.00005 mole) of (rac)-4-(9-cyclopentyl-5,7-dimethyl-6-oxo-6,7,8,9-tetrahydro-5H-pyrimido[4,5-b][1,4]diazepin-2-yl amino)-3-methyl-benzoic acid (I-7), 0.023 g (0.00006 mole) of 1-[bis(dimethylamino)methylene]-1H-1,2,3-triazolo[4,5-b]pyridinium-3-oxide hexafluorophosphate, 0.018 mL (0.0001 mole) of ethyldiisopropyl amine and 1.0 mL of dimethylformamide was stirred for 5 minutes and then 0.0085 g (0.000075 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.009 g of (rac)-4-(9-cyclopentyl-5,7-dimethyl-6-oxo-6,7,8,9-tetrahydro-5H-pyrimido[4,5-b][1,4]diazepin-2-ylamino)-3-methyl-N-(1-methyl-piperidin-4-yl)-benzamide (I-8) as a white solid.

EXAMPLE 11

(rac)-N-(1-Benzyl-piperidin-4-yl)-4-(9-cyclopentyl-5,7-dimethyl-6-oxo-6,7,8,9-tetrahydro-5H-pyrimido[4,5-b][1,4]diazepin-2-ylamino)-3-methoxy-benzamide (I-9)

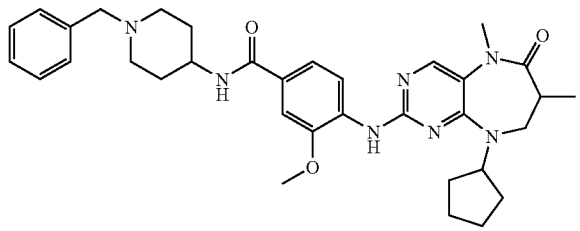

A mixture of 0.021 g (0.00005 mole) of (rac)-4-(9-cyclopentyl-5,7-dimethyl-6-oxo-6,7,8,9-tetrahydro-5H-pyrimido[4,5-b][1,4]diazepin-2-yl amino)-3-methoxy-benzoic acid (I-3), 0.023 g (0.00006 mole) of 1-[bis(dimethylamino)methylene]-1H-1,2,3-triazolo[4,5-b]pyridinium-3-oxide hexafluorophosphate, 0.018 mL (0.0001 mole) of ethyldiisopropyl amine and 1.0 mL of dimethylformamide was stirred for 5 minutes and then 0.015 g (0.000075 mole) of 4-amino-1-benzyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.015 g of (rac)-4-(9-cyclopentyl-5,7-dimethyl-6-oxo-6,7,8,9-tetrahydro-5H-pyrimido[4,5-b][1,4]diazepin-2-ylamino)-3-methoxy-N-(1-benzyl-piperidin-4-yl)-benzamide (I-9) as a white solid.

EXAMPLE 12

4-(9-Cyclopentyl-5-methyl-6-oxo-6,7,8,9-tetrahydro-5H-pyrimido[4,5-b][1,4]diazepin-2-ylamino)-3-methoxy-benzoic acid (I-10)

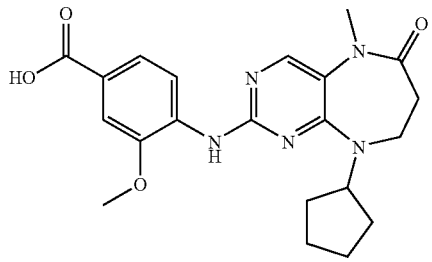

step a

A solution of 1.85 g (0.01 mole) of 3-cyclopentylamino-propanoic acid ethyl ester in 30 mL of water was added dropwise to a solution of 1.94 g (0.01 mole) of 2,4-dichloro-5-nitro-pyrimidine in 30 mL of ethyl ether. At 0 degrees, 2.0 g (0.020 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-80:20) gave 3.05 g of 3-[(2-chloro-5-nitro-pyrimidin-4-yl)-cyclopentyl-amino]-propanoic acid ethyl ester (IV-10)

step b

To a solution of 0.356 g (0.001 mole) of 3-[(2-chloro-5-nitro-pyrimidin-4-yl)-cyclopentyl-amino]-propanoic acid ethyl ester (IV-10) in 5 mL of ethanol was added 0.562 g (0.0025 mole) of stannous chloride dihydrate and 0.1 mL of hydrochloric acid. The mixture was heated to 60 degrees for 2 hrs. The solvent was evaporated under reduced pressure. The residue was taken up in 20 mL of water and extracted with three times with 20 mL of ethyl acetate. The combined organic layers were dried over anhydrous magnesium sulfate, filtered and concentrated under reduced pressure. Purification by silica gel chromatography, eluting with dichloromethane-methanol (100:0-95:5) gave 0.174 g of 2-chloro-9-cyclopentyl-5,7,8,9-tetrahydro-pyrimido[4,5-b][1,4]diazepin-6-one (VI-10) as a white solid.

step c

To a mixture of 0.13 g (0.0005 mole) of 2-chloro-9-cyclopentyl-5,7,8,9-tetrahydro-pyrimido[4,5-b][1,4]diazepin-6-one (VI-10), 1 mL of N,N-dimethylacetamide and 0.047 mL (0.00075 mole) of iodomethane at 0 degrees was added 0.03 g (0.00075 mole) of 60% sodium hydride in oil. The mixture was stirred at ambient temperature for 1 hour, then 20 mL of water was added. The precipitate was collected by filtration to give 0.135 g of 2-chloro-9-cyclopentyl-5-methyl-5,7,8,9-tetrahydro-pyrimido[4,5-b][1,4]diazepin-6-one (VII-10) as an yellow solid.

step d

A mixture of 0.135 g (0.00048 mole) of 2-chloro-9-cyclopentyl-5-methyl-5,7,8,9-tetrahydro-pyrimido[4,5-b][1,4]diazepin-6-one (VII-10), 0.096 g (0.00058 mole) of 4-amino-3-methoxy-benzoic acid, 1 mL of ethanol, 3 mL of water, and 2 drops of hydrochloric acid was heated at 100 degrees overnight. Upon cooling, a precipitate formed which was collected by filtration to give 0.14 g of 4-(9-cyclopentyl-5-methyl-6-oxo-6,7,8,9-tetrahydro-5H-pyrimido[4,5-b][1,4]diazepin-2-yl amino)-3-methoxy-benzoic acid (I-10) as an off-white solid.

EXAMPLE 13

4-(9-Cyclopentyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-11)

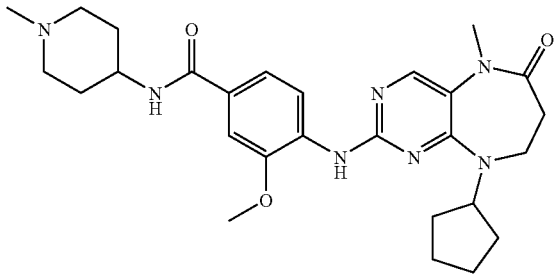

A mixture of 0.140 g (0.00034 mole) of 4-(9-cyclopentyl-5-methyl-6-oxo-6,7,8,9-tetrahydro-5H-pyrimido[4,5-b][1,4]diazepin-2-yl amino)-3-methoxy-benzoic acid (I-10), 0.156 g (0.00041 mole) of 1-[bis(dimethylamino)methylene]-1H-1,2,3-triazolo[4,5-b]pyridinium-3-oxide hexafluorophosphate, 0.178 mL (0.00102 mole) of ethyldiisopropyl amine and 2.0 mL of dimethylformamide was stirred for 5 minutes and then 0.046 g (0.00041 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with an acetonitrile-water gradient (20:80-100:0) to give 0.130 g of 4-(9-cyclopentyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-11) as a white solid.

EXAMPLE 14

(rac)-4-(9-Cyclopentyl-7-ethyl-5-methyl-6-oxo-6,7,8,9-tetrahydro-5H-pyrimido[4,5-b][1,4]diazepin-2-ylamino)-3-methoxy-benzoic acid (I-12)

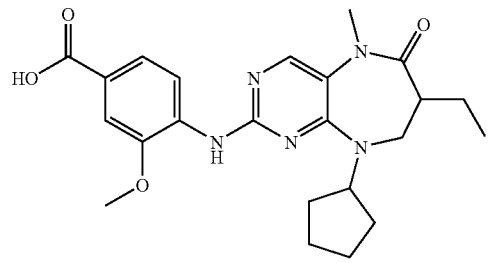

step a

A solution of 1.07 g (0.005 mole) of (rac)-2-cyclopentylaminomethyl-butanoic acid ethyl ester in 25 mL of water was added dropwise to a solution of 0.97 g (0.005 mole) of 2,4-dichloro-5-nitro-pyrimidine in 25 mL of ethyl ether. At 0 degrees, 1.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-80:20) gave 1.3 g of (rac)-2-{[(2-chloro-5-nitro-pyrimidin-4-yl)-cyclopentyl-amino]-methyl}-butanoic acid ethyl ester (IV-12).

step b

To a solution of 0.37 g (0.001 mole) of (rac)-2-{[(2-chloro-5-nitro-pyrimidin-4-yl)-cyclopentyl-amino]-methyl}-butanoic acid ethyl ester in 5 mL of ethanol was added 0.562 g (0.0025 mole) of stannous chloride dihydrate and 0.1 mL of hydrochloric acid. The mixture was heated to 60 degrees for 2 hrs. The solvent was evaporated under reduced pressure. The residue was taken up in 20 mL of water and extracted with three times with 20 mL of ethyl acetate. The combined organic layers were dried over anhydrous magnesium sulfate, filtered and concentrated under reduced pressure. Purification by silica gel chromatography, eluting with dichloromethane-methanol (100:0-95:5) gave 0.155 g of (rac)-2-chloro-9-cyclopentyl-7-ethyl-5,7,8,9-tetrahydro-pyrimido[4,5-b][1,4]diazepin-6-one (VI-12) as a white solid.

step c

To a mixture of 0.06 g (0.0002 mole) of (rac)-2-chloro-9-cyclopentyl-7-ethyl-5,7,8,9-tetrahydro-pyrimido[4,5-b][1,4]diazepin-6-one, 1 mL of N,N-dimethylacetamide and 0.019 mL (0.0003 mole) of iodomethane at 0 degrees was added 0.012 g (0.0003 mole) of 60% sodium hydride in oil. The mixture was stirred at ambient temperature for 1 hour, then 10 mL of water was added. The precipitate was collected by filtration to give 0.058 g of (rac)-2-chloro-9-cyclopentyl-7-ethyl-5-methyl-5,7,8,9-tetrahydro-pyrimido[4,5-][1,4]diazepin-6-one (VII-12) as an yellow solid.

step d

A mixture of 0.058 g (0.00019 mole) of (rac)-2-chloro-9-cyclopentyl-7-ethyl-5-methyl-5,7,8,9-tetrahydro-pyrimido[4,5-b][1,4]diazepin-6-one (VII-12), 0.038 g (0.00023 mole) of 4-amino-3-methoxy-benzoic acid, 0.5 mL of ethanol, 2 mL of water, and 2 drops of hydrochloric acid was heated to 100 degrees overnight. Upon cooling, a precipitate formed which was collected by filtration to give 0.046 g of (rac)-4-(9-cyclopentyl-7-ethyl-5-methyl-6-oxo-6,7,8,9-tetrahydro-5H-pyrimido[4,5-b][1,4]diazepin-2-yl amino)-3-methoxy-benzoic acid (I-12) as an off-white solid.

EXAMPLE 15

(rac)-4-(9-Cyclopentyl-7-ethyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-13)

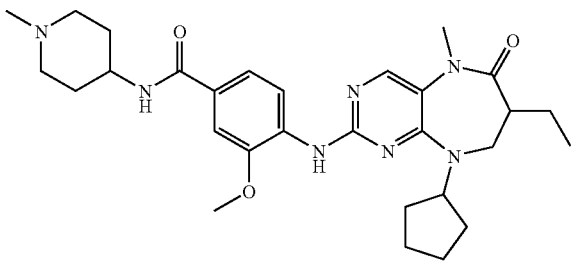

A mixture of 0.044 g (0.0001 mole) of (rac)-4-(9-cyclopentyl-7-ethyl-5-methyl-6-oxo-6,7,8,9-tetrahydro-5H-pyrimido[4,5-b][1,4]diazepin-2-yl amino)-3-methoxy-benzoic acid (I-12), 0.045 g (0.00012 mole) of 1-[bis(dimethylamino)methylene]-1H-1,2,3-triazolo[4,5-b]pyridinium-3-oxide hexafluorophosphate, 0.052 mL (0.0003 mole) of ethyldiisopropyl amine and 1 mL of dimethylformamide was stirred for 5 minutes and then 0.017 g (0.00015 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.038 g of (rac)-4-(9-cyclopentyl-7-ethyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-13) as a white solid.

EXAMPLE 16

(rac)-4-(9-Cyclopentyl-5,7-diethyl-6-oxo-6,7,8,9-tetrahydro-5H-pyrimido[4,5-b][1,4]diazepin-2-ylamino)-3-methoxy-benzoic acid (I-14)

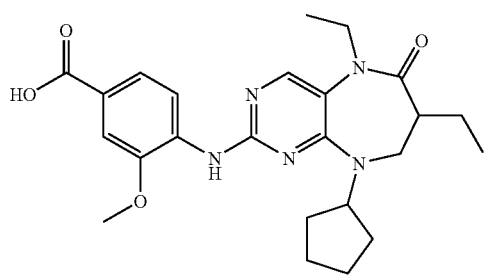

step a

To a mixture of 0.045 g (0.00015 mole) of (rac)-2-chloro-9-cyclopentyl-7-ethyl-5,7,8,9-tetrahydro-pyrimido[4,5-b][1,4]diazepin-6-one (VI-12), 1 mL of N,N-dimethylacetamide and 0.018 mL (0.000225 mole) of iodoethane at 0 degrees was added 0.009 g (0.000225 mole) of 60% sodium hydride in oil. The mixture was stirred at ambient temperature for 1 hour, then 10 mL of water was added. The precipitate was collected by filtration to give 0.042 g of (rac)-2-chloro-9-cyclopentyl-5,7-diethyl-5,7,8,9-tetrahydro-pyrimido[4,5-][1,4]diazepin-6-one (VII-14) as an yellow solid.

step b

A mixture of 0.042 g (0.00013 mole) of (rac)-2-chloro-9-cyclopentyl-7-ethyl-5-ethyl-5,7,8,9-tetrahydro-pyrimido[4,5-b][1,4]diazepin-6-one (VII-14), 0.026 g (0.00016 mole) of 4-amino-3-methoxy-benzoic acid, 0.5 mL of ethanol, 2 mL of water, and 2 drops of hydrochloric acid was heated to 100 degrees overnight. Upon cooling, a precipitate formed which was collected by filtration to give 0.037 g of (rac)-4-(9-cyclopentyl-5,7-diethyl-6-oxo-6,7,8,9-tetrahydro-5H-pyrimido[4,5-b][1,4]diazepin-2-yl amino)-3-methoxy-benzoic acid (I-14) as an off-white solid.

EXAMPLE 17

(rac)-4-(9-Cyclopentyl-5,7-diethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-15)

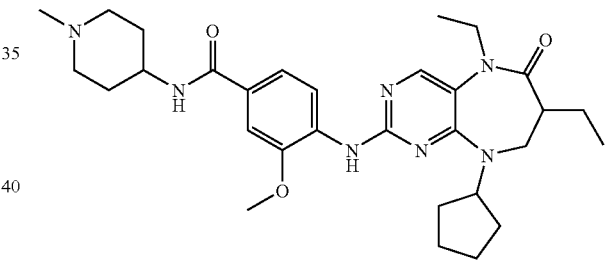

A mixture of 0.037 g (0.00008 mole) of (rac)-4-(9-cyclopentyl-7-ethyl-5-ethyl-6-oxo-6,7,8,9-tetrahydro-5H-pyrimido[4,5-b][1,4]diazepin-2-yl amino)-3-methoxy-benzoic acid (I-14), 0.037 g (0.00012 mole) of 1-[bis(dimethylamino)methylene]-1H-1,2,3-triazolo[4,5-b]pyridinium-3-oxide hexafluorophosphate, 0.042 mL (0.00024 mole) of ethyldiisopropyl amine and 1 mL of dimethylformamide was stirred for 5 minutes and then 0.014 g (0.00012 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with an acetonitrile-water gradient (20:80-100:0) to give 0.038 g of (rac)-4-(9-cyclopentyl-5,7-diethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-15) as a white solid.

EXAMPLE 18

(rac)-4-(9-Cyclopentyl-5-methyl-6-oxo-7-propyl-6,7,8,9-tetrahydro-5H-pyrimido[4,5-b][1,4]diazepin-2-ylamino)-3-methoxy-benzoic acid (I-16)

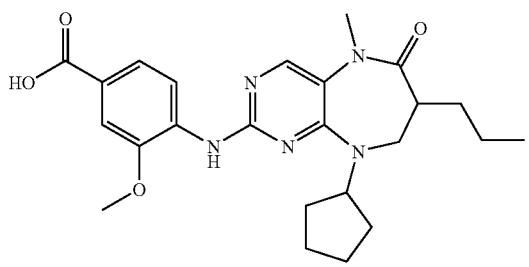

step a

A solution of 1.14 g (0.005 mole) of (rac)-2-cyclopentylaminomethyl-pentanoic acid ethyl ester in 25 mL of water was added dropwise to a solution of 0.97 g (0.005 mole) of 2,4-dichloro-5-nitro-pyrimidine in 25 mL of ethyl ether. At 0 degrees, 1.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-80:20) gave 1.4 g of (rac)-2-{[(2-chloro-5-nitro-pyrimidin-4-yl)-cyclopentyl-amino]-methyl}-pentanoic acid ethyl ester (IV-16).

step b

To a solution of 0.384 g (0.001 mole) of (rac)-2-{[(2-chloro-5-nitro-pyrimidin-4-yl)-cyclopentyl-amino]-methyl}-pentanoic acid ethyl ester (IV-16) in 5 mL of ethanol was added 0.562 g (0.0025 mole) of stannous chloride dihydrate and 0.1 mL of hydrochloric acid. The mixture was heated to 60 degrees for 2 hrs. The solvent was evaporated under reduced pressure. The residue was taken up in 20 mL of water and extracted with three times with 20 mL of ethyl acetate. The combined organic layers were dried with magnesium sulfate, filtered and concentrated under reduced pressure. Purification by silica gel chromatography, eluting with dichloromethane-methanol (100:0-95:5) gave 0.210 g of (rac)-2-chloro-9-cyclopentyl-7-propyl-5,7,8,9-tetrahydro-pyrimido[4,5-b][1,4]diazepin-6-one (VI-16) as a white solid.

step c

To a mixture of 0.210 g (0.00068 mole) of (rac)-2-chloro-9-cyclopentyl-7-propyl-5,7,8,9-tetrahydro-pyrimido[4,5-b][1,4]diazepin-6-one (VI-16), 2 mL of N,N-dimethylacetamide and 0.064 mL (0.001 mole) of iodomethane at 0 degrees was added 0.04 g (0.001 mole) of 60% sodium hydride in oil. The mixture was stirred at ambient temperature for 1 hour, then 10 mL of water was added. The precipitate was collected by filtration to give 0.208 g of (rac)-2-chloro-9-cyclopentyl-5-methyl-7-propyl-5,7,8,9-tetrahydro-pyrimido[4,5-][1,4]diazepin-6-one (VII-16) as an yellow solid.

step d A mixture of 0.208 g (0.00065 mole) of (rac)-2-chloro-9-cyclopentyl-5-methyl-7-propyl-5,7,8,9-tetrahydro-pyrimido[4,5-b][1,4]diazepin-6-one (VII-16), 0.13 g (0.00078 mole) of 4-amino-3-methoxy-benzoic acid, 0.5 mL of etha-nol, 2 mL of water, and 2 drops of hydrochloric acid was heated at 100 degrees overnight. Upon cooling, a precipitate formed which was collected by filtration to give 0.205 g of (rac)-4-(9-cyclopentyl-5-methyl-7-propyl-6-oxo-6,7,8,9-tetrahydro-5H-pyrimido[4,5-b][1,4]diazepin-2-ylamino)-3-methoxy-benzoic acid (I-16) as an off-white solid.

EXAMPLE 19

(rac)-4-(9-Cyclopentyl-5-methyl-6-oxo-7-propyl-6,7,8,9-tetrahydro-5H-pyrimido[4,5-b][1,4]diazepin-2-ylamino)-3-methoxy-N-(1-methyl-piperidin-4-yl)-benzamide (I-17)

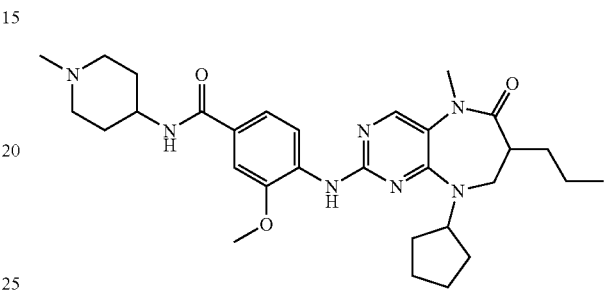

A mixture of 0.200 g (0.00044 mole) of (rac)-4-(9-cyclopentyl-5-methyl-7-propyl-6-oxo-6,7,8,9-tetrahydro-5H-pyrimido[4,5-b][1,4]diazepin-2-yl amino)-3-methoxy-benzoic acid (I-16), 0.200 g (0.00053 mole) of 1-[bis(dimethylamino)methylene]-1H-1,2,3-triazolo[4,5-b]pyridinium-3-oxide hexafluorophosphate, 0.230 mL (0.0013 mole) of ethyldiisopropyl amine and 2 mL of dimethylformamide was stirred for 5 minutes and then 0.075 g (0.00066 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.186 g of (rac)-4-(9-cyclopentyl-5-methyl-7-propyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-17) as a white solid.

EXAMPLE 20

(rac)-4-(9-Cyclohexyl-7-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-18)

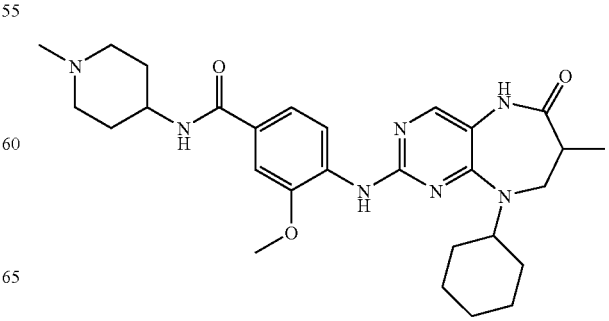

step a

To a mixture of 2.73 g (0.010 mole) of (rac)-3-cyclohexyl-amino-2-methyl-propanoic acid ethyl ester acetic acid salt, 1.94 g (0.010 mole) of 2,4-dichloro-5-nitro-pyrimidine, 50 mL of ethyl acetate and 25 mL of water was added 3.0 g (0.030 mole) of potassium bicarbonate. The mixture was stirred for 3 hours, then diluted with 50 mL of ethyl acetate and 50 mL of water. The aqueous layer was extracted twice with 100 mL of ethyl acetate, and the ethyl acetate layers were washed with 100 mL of brine, combined, dried over anhydrous magnesium sulfate, filtered and concentrated under reduced pressure. The residue was purified by silica gel chromatography, eluting with dichloromethane-ethyl acetate (95:5) to give 2.27 g of (rac)-3-[(2-chloro-5-nitro-pyrimidin-4-yl)-cyclohexyl-amino]-2-methyl-propanoic acid ethyl ester (IV-18) as a pale yellow oil.

step b

To a solution of 2.27 g (0.0061 mole) of (rac)-3-[(2-chloro-5-nitro-pyrimidin-4-yl)-cyclohexyl-amino]-2-methyl-propanoic acid ethyl ester in 40 mL of acetic acid was added 2.0 g (0.0358 g-atom) of iron powder. The mixture was heated at 80 degrees for 2 hours, and then filtered through Celite while still hot. The filtercake was washed with 100 mL of ethyl acetate and the combined filtrate was washed successively with 100 mL of water, 100 mL of 7.4 M ammonium hydroxide, 50 mL of water and then 100 mL of brine. The aqueous layers were back washed with 100 mL of ethyl acetate and the combined ethyl acetate layers dried over anhydrous magnesium sulfate, filtered and concentrated under reduced pressure. The residue was purified by silica gel chromatography, eluting with ethyl acetate-dichloromethane (1:1), followed by crystallization from dichloromethane-hexanes to give 1.48 g of (rac)-2-chloro-9-cyclohexyl-7-methyl-5,7,8,9-tetrahydro-pyrimido[4,5-b][1,4]diazepin-6-one (VI-18) as white needles.

step c

To an ice cooled solution of 3.43 g (0.030 mole) of 4-amino-1-methylpiperidine, 4.58 g (0.045 mole) of triethylamine and 75 mL of tetrahydrofuran, was added a solution of 6.44 g (0.0347 mole) of 4-nitrobenzoyl chloride in 25 mL of tetrahydrofuran. The mixture was stirred at room temperature for 6 hours, then diluted with 50 mL of water and 100 mL of saturated sodium bicarbonate. After stirring another 30 minutes, the mixture was extracted twice with 200 mL of ethyl acetate. The ethyl acetate layers were washed with 200 mL of water, 200 mL of brine, combined, dried over anhydrous magnesium sulfate, filtered and concentrated under reduced pressure to give 4.34 g of N-(1-methyl-piperidin-4-yl)-4-nitro-benzamide as off-white powder.

A solution of 4.34 g (0.0165 mole) of N-(1-methyl-piperidin-4-yl)-4-nitro-benzamide, 0.50 g of 10% palladium on carbon catalyst, 200 mL of ethanol and 30 mL of tetrahydrofuran was stirred under an atmosphere of hydrogen for 4 hours. The mixture was then filtered through Celite and concentrated under reduced pressure. The residue was recrystallized from methanol-ethyl acetate to give 2.21 g of 4-amino-N-(1-methyl-piperidin-4-yl)-benzamide as off-white crystals.

A solution of 0.050 g (0.00017 mole) of (rac)-2-chloro-9-cyclohexyl-7-methyl-5,7,8,9-tetrahydro-pyrimido[4,5-b][1,4]diazepin-6-one (VI-18), 0.040 g (0.00017 mole) of 4-amino-3-methoxy-N-(1-methyl-piperidin-4-yl)-benzamide, 0.050 g (0.00026 mole) of p-toluenesulfonic acid monohydrate and 4.0 mL of 2-propanol was heated at 180 degrees for 1.5 hours in a microwave reactor. The reaction mixture was concentrated under reduced pressure and the residue purified by C18 reverse phase chromatography, eluting with acetonitrile—water containing 0.075% trifluoroacetic acid to give 0.045 g of (rac)-4-(9-cyclohexyl-7-methyl-6-oxo-6,7,8,9-tetrahydro-5H-pyrimido[4,5-b][1,4]diazepin-2-ylamino)-3-methoxy-N-(1-methyl-piperidin-4-yl)-benzamide trifluoro-acetic acid salt as a white powder.

HRMS (ES+) m/z Calcd for C28H39N7O3+H [(M+H)+]: 522.3187. Found: 522.3188.

To a suspension of 0.045 g of (rac)-4-(9-cyclohexyl-7-methyl-6-oxo-6,7,8,9-tetrahydro-5H-pyrimido[4,5-b][1,4]diazepin-2-ylamino)-3-methoxy-N-(1-methyl-piperidin-4-yl)-benzamide trifluoro-acetic acid salt in tetrahydrofuran was added 0.2 g of SilicaBond Carbonate (Silicycle). The mixture was stirred at room temperature for 3 hours, then filtered and concentrated under reduced pressure. The residue was purified by silica gel chromatography eluting with dichloromethane-methanol (100:0-75:25) to give 0.020 g of (rac)-4-(9-cyclohexyl-7-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-18) as a white powder. HRMS (ES+) m/z Calcd for C28H39N7O3+H [(M+H)+]: 522.3187. Found: 522.3187.

EXAMPLE 21

(rac)-4-(9-Cyclohexyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-19)

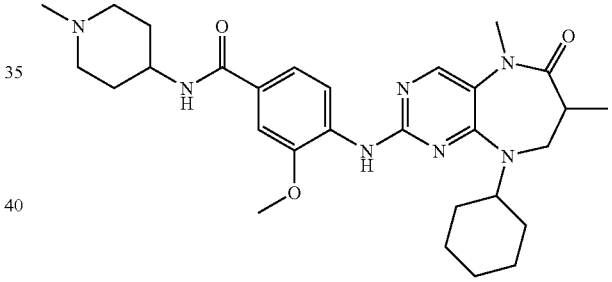

step a

To an ice cooled solution of 0.48 g (0.0016 mole) of (rac)-2-chloro-9-cyclohexyl-7-methyl-5,7,8,9-tetrahydro-pyrimido[4,5-b][1,4]diazepin-6-one (VI-18), 0.2 mL (0.0032 mole) of iodomethane and 5 mL of dimethylformamide was added 0.13 g (0.0032 mole) of 60% oil dispersion of sodium hydride. The mixture was stirred at room temperature for 1 hour, then 100 mL of water was added and the mixture was extracted with twice with 100 mL of ethyl acetate. The organic layers were washed with 100 mL of brine, combined, dried over anhydrous magnesium sulfate, filtered, and concentrated under reduced pressure. The residue was purified by silica gel chromatography, eluting with dichloromethane-ethyl acetate (85:15), followed by recrystallization from dichloromethane-hexanes to give 0.41 g of (rac)-2-chloro-9-cyclohexyl-5,7-dimethyl-5,7,8,9-tetrahydro-pyrimido[4,5-b][1,4]diazepin-6-one (VII-19) as white needles.

step b

A solution of 0.050 g (0.00016 mole) of (rac)-2-chloro-9-cyclohexyl-5,7-dimethyl-5,7,8,9-tetrahydro-pyrimido[4,5-b][1,4]diazepin-6-one (VII-19), 0.040 g (0.00016 mole) of 4-amino-3-methoxy-N-(1-methyl-piperidin-4-yl)-benzamide, 0.050 g of p-toluenesulfonic acid monohydratein 4.0 mL of 2-propanol was heated at 200 degrees for 1 hour in a microwave reactor. The reaction mixture was purified by C18 reverse phase chromatography, eluting with acetonitrile—water containing 0.075% trifluoroacetic acid to give 0.066 g of (rac)-4-(9-cyclohexyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide trifluoroacetic acid salt as a white powder. To a suspension of 0.066 of (rac)-4-(9-cyclohexyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide trifluoroacetic acid salt in tetrahydrofuran was added 0.25 g of SilicaBond Carbonate (Silicycle). The mixture was stirred at room temperature for 4 hours, then filtered and concentrated under reduced pressure. The residue was purified by silica gel chromatography eluting with dichloromethane-methanol (100:0-75:25) to give 0.041 g of (rac)-4-(9-cyclohexyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-19) as a white powder. HRMS (ES+) m/z Calcd for C29H41N7O3+H [(M+H)+]: 536.3344. Found: 536.3343.

EXAMPLE 22

4-(9-Cyclohexyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-20)

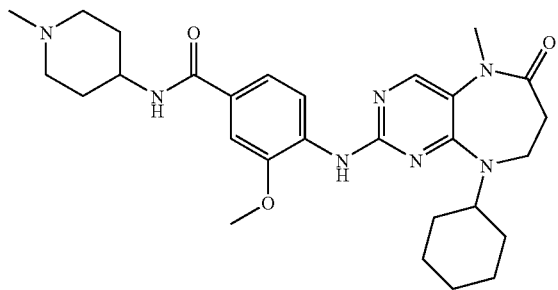

step a

A solution of 1.32 g (0.0058 mole) of 4-cyclohexylaminopropanoic acid tert-butyl ester in 5 mL of acetonitrile was added dropwise to a mixture of 1.24 g (0.0064 mole) of 2,4-dichloro-5-nitro-pyrimidine, 1.16 g (0.0116 mole) of potassium bicarbonate and 20 mL of acetonitrile at ambient temperature over 45 mins. The mixture was stirred for an additional 2 hours and then diluted with 30 mL of ethyl acetate. The mixture was filtered, concentrated under reduced pressure and the residue was purified by silica gel chromatography, eluting with hexanes-ethyl acetate (100:0-90:10) to give 1.53 g of 3-[(2-chloro-5-nitro-pyrimidin-4-yl)-cyclohexyl-amino]-propanoic acid tert-butyl ester (IV-20).

step b

A solution of 1.53 g (0.004 mole) of 3-[(2-chloro-5-nitro-pyrimidin-4-yl)-cyclohexyl-amino]-propionic acid tert-butyl ester (IV-20) in 20 mL of ethyl acetate was added in portions over 10 minutes to a mixture of 2.69 g (0.012 mole) of stannous chloride dihydrate, 12 mL of ethanol and 0.5 mL of hydrochloric acid. The mixture was stirred overnight and then diluted with 30 mL of water and extracted with ethyl acetate. The ethyl acetate extract was dried over anhydrous magnesium sulfate, filtered and concentrated under reduced pressure. The residue was purified by silica gel chromatography, eluting with dichloromethane-methanol (100:0-92:8) to give 0.47 g of 2-chloro-9-cyclohexyl-5,7,8,9-tetrahydro-pyrimido [4,5-b][1,4]diazepin-6-one (VI-20).

step c

A mixture of 0.12 g (0.00042 mole) of 2-chloro-9-cyclohexyl-5,7,8,9-tetrahydro-pyrimido[4,5-b][1,4]diazepin-6-one (VI-20), 0.469 g (0.00144 mole) of cesium carbonate, 0.135 g (0.00096 mole) of iodomethane and 1 mL of dimethylformamide was stirred overnight at ambient temperature and then diluted with 5 mL of water. The mixture was stirred for 15 minutes and the solid was collected by filtration to give 2-chloro-9-cyclohexyl-5-methyl-5,7,8,9-tetrahydro-pyrimido[4,5-b][1,4]diazepin-6-one (VII-20) which was used without further purification.

step d

A mixture of the 2-chloro-9-cyclohexyl-5-methyl-5,7,8,9-tetrahydro-pyrimido[4,5-b][1,4]diazepin-6-one (VII-20) obtained in the previous step, 1 mL of ethanol, 1 mL of 3M hydrochloric acid and 0.071 g (0.00042 mole) of 4-amino-3-methoxybenzoic acid was heated in a sealed vial at 100 degrees for 3 hours. The cooled mixture was diluted with 2 mL of water, and the solid collected by filtration to five 0.042 g of 4-(9-cyclohexyl-5-methyl-6-oxo-6,7,8,9-tetrahydro-5H-pyrimido[4,5-b][1,4]diazepin-2-ylamino)-3-methoxy-benzoic acid (I-20a).

step e

A mixture of 0.041 g (0.00096 mole) of 4-(9-cyclohexyl-5-methyl-6-oxo-6,7,8,9-tetrahydro-5H-pyrimido[4,5-b][1,4]diazepin-2-lamino)-3-methoxy-benzoic acid (I-20a), 0.046 g (0.00012 mole) of 1-[bis(dimethylamino)-methylene]-1H-1,2,3-triazolo[4,5-b]pyridinium-3-oxide hexafluorophosphate, 0.021 g (0.00019 mole) of 4-amino-1-methylpiperidine, 0.05 mL of triethylamine and 1.5 mL of dichloromethane was stirred at ambient temperature for 2.5 hours. The mixture was concentrated under reduced pressure, and the residue purified by C18 reverse phase silica gel chromatography, eluting with an acetonitrile-water gradient (10:90-100:0) to give 0.0072 g of 4-(9-cyclohexyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-20)

EXAMPLE 23

4-(9-Cyclopentyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-21)

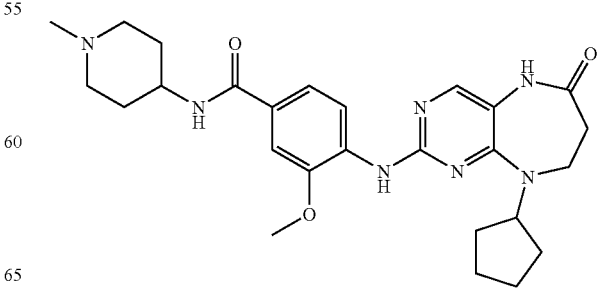

step a

A mixture of 0.053 g (0.0002 mole) of 2-chloro-9-cyclopentyl-5,7,8,9-tetrahydro-pyrimido[4,5-b][1,4]diazepin-6-one (VI-10), 0.04 g (0.00024 mole) of 4-amino-3-methoxy-benzoic acid, 0.5 mL of ethanol, 2 mL of water, and 2 drops of hydrochloric acid was heated to 100 degrees overnight. Upon cooling, a precipitate formed which was collected by filtration to give 0.049 g of 4-(9-cyclopentyl-6-oxo-6,7,8,9-tetrahydro-5H-pyrimido[4,5-b][1,4]diazepin-2-yl amino)-3-methoxy-benzoic acid as an off-white solid.

step b

A mixture of 0.04 g (0.0001 mole) of 4-(9-cyclopentyl-6-oxo-6,7,8,9-tetrahydro-5H-pyrimido[4,5-b][1,4]diazepin-2-yl amino)-3-methoxy-benzoic acid, 0.042 g (0.00011 mole) of 1-[bis(dimethylamino)methylene]-1H-1,2,3-triazolo[4,5-b]pyridinium-3-oxide hexafluorophosphate, 0.061 mL (0.00035 mole) of ethyldiisopropyl amine and 2.0 mL of dimethylformamide was stirred for 5 minutes and then 0.019 g (0.00015 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.035 g of 4-(9-cyclopentyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-21) as a white solid.

EXAMPLE 24

4-(9-Benzyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-22)

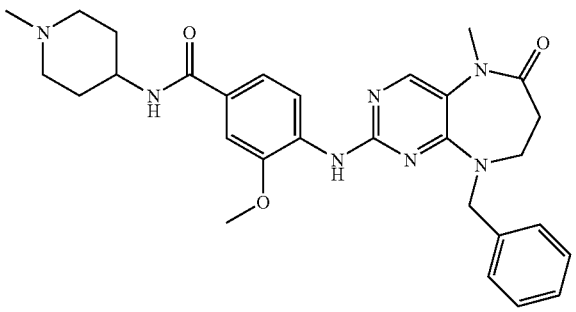

step a

A solution of 1.04 g (0.005 mole) of 3-benzylamino-propanoic acid ethyl ester in 20 mL of water was added dropwise to a solution of 0.97 g (0.005 mole) of 2,4-dichloro-5-nitro-pyrimidine in 20 mL of ethyl ether. At 0 degrees, 1.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-90:10) gave 1.70 g of 3-[benzyl-(2-chloro-5-nitro-pyrimidin-4-yl)-amino]-propanoic acid ethyl ester (IV-22).

step b

To a solution of 1.1 g (0.003 mole) of 3-[benzyl-(2-chloro-5-nitro-pyrimidin-4-yl)-amino]-propanoic acid ethyl ester (IV-22) in 20 mL of ethanol was added 1.7 g (0.0075 mole) of stannous chloride dehydrate and 0.5 mL of hydrochloric acid. The mixture was heated at 60 degrees for 2 hrs. The solvent was evaporated under reduced pressure. The residue was taken up in 50 mL of water and extracted three times with 50 mL of ethyl acetate. The combined organic layers were dried over anhydrous magnesium sulfate, filtered and concentrated under reduced pressure. Purification by silica gel chromatography, eluting with dichloromethane-methanol (100:0-95:5) gave 0.16 g of 9-benzyl-2-chloro-5,7,8,9-tetrahydro-pyrimido[4,5-b][1,4]diazepin-6-one (VI-22) as a white solid.

step c

To a mixture of 0.144 g (0.0005 mole) of 9-benzyl-2-chloro-5,7,8,9-tetrahydro-pyrimido[4,5-b][1,4]diazepin-6-one (VI-22), 1 mL of N,N-dimethylacetamide and 0.047 mL (0.00075 mole) of iodomethane at 0 degrees was added 0.03 g (0.00075 mole) of 60% sodium hydride in oil. The mixture was stirred at ambient temperature for 1 hour, then 20 mL of water was added. The precipitate was collected by filtration to give 0.134 g of 9-benzyl-2-chloro-5-methyl-5,7,8,9-tetrahydro-pyrimido[4,5-b][1,4]diazepin-6-one (VII-22) as an yellow solid.

step d

A mixture of 0.06 g (0.0002 mole) of 9-benzyl-2-chloro-5-methyl-5,7,8,9-tetrahydro-pyrimido[4,5-b][1,4]diazepin-6-one (VII-22), 0.04 g (0.00024 mole) of 4-amino-3-methoxy-benzoic acid, 0.5 mL of ethanol, 2 mL of water, and 2 drops of hydrochloric acid was heated at 100 degrees overnight. Upon cooling, a precipitate formed which was collected by filtration to give 0.056 g of 4-(9-benzyl-5-methyl-6-oxo-6,7,8,9-tetrahydro-5H-pyrimido[4,5-b][1,4]diazepin-2-yl amino)-3-methoxy-benzoic acid (I-22a) as an off-white solid.

step e

A mixture of 0.056 g (0.00013 mole) of 4-(9-benzyl-5-methyl-6-oxo-6,7,8,9-tetrahydro-5H-pyrimido[4,5-b][1,4] diazepin-2-yl amino)-3-methoxy-benzoic acid, 0.054 g (0.00014 mole) of 1-[bis(dimethylamino)methylene]-1H-1,2,3-triazolo[4,5-b]pyridinium-3-oxide hexafluorophosphate, 0.079 mL (0.00046 mole) of ethyldiisopropyl amine and 2.0 mL of dimethylformamide was stirred for 5 minutes and then 0.022 g (0.0002 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.045 g of 4-(9-benzyl-5-methyl-6-oxo-6,7,8,9-tetrahydro-5H-pyrimido[4,5-b][1,4] diazepin-2-ylamino)-3-methoxy-N-(1-methyl-piperidin-4-yl)-benzamide (I-22) as a white solid.

EXAMPLE 25

4-(9-Cyclobutyl-5-methyl-6-oxo-6,7,8,9-tetrahydro-5H-pyrimido[4,5-b][1,4]diazepin-2-ylamino)-3-methoxy-benzoic acid (I-23)

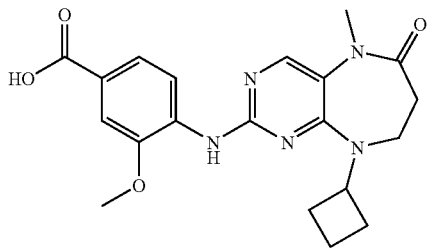

step a

A solution of 1.9 g (0.011 mole) of 3-cyclobutylaminopropanoic acid ethyl ester in 7 mL of acetonitrile was added dropwise to a mixture of 1.74 g (0.09 mole) of 2,4-dichloro-5-nitro-pyrimidine and 2.07 g (0.021 mole) of potassium bicarbonate and 20 mL of acetonitrile at ambient temperature over 45 mins. The mixture was stirred for 2.5 hours, then diluted with 45 mL of ethyl acetate. The mixture was filtered, concentrated under reduced pressure and the residue purified by silica gel chromatography, eluting with hexanes-ethyl acetate (100:0-90:10) to give 1.7 g of 3-[(2-chloro-5-nitro-pyrimidin-4-yl)-cyclobutyl-amino]-propanoic acid ethyl ester (IV-23).

step b

A solution of 1.7 g (0.0052 mole) of 3-[(2-chloro-5-nitro-pyrimidin-4-yl)-cyclobutyl-amino]-propanoic acid ethyl ester (IV-23) in 10 mL of ethyl acetate was added over 1 hour to a suspension of 3.5 g (0.016 mole) of stannous chloride dihydrate in 12 mL of ethyl acetate and 1 mL of hydrochloric acid at ambient temperature. The mixture was stirred for additional hour and then diluted with 30 mL of water, and extracted with ethyl acetate. The ethyl acetate layer was dried over anhydrous magnesium sulfate, filtered and concentrated under reduced pressure. The residue was purified by silica gel chromatography, eluting with hexanes-ethyl acetate (80:20-0:100) to give 0.87 g of 2-chloro-9-cyclobutyl-5,7,8,9-tetrahydro-pyrimido[4,5-b][1,4]diazepin-6-one (VI-23)

step c

A mixture of 0.127 g (0.0005 mole) of 2-chloro-9-cyclobutyl-5,7,8,9-tetrahydro-pyrimido[4,5-b][1,4]diazepin-6-one (VI-23), 0.442 g (0.0014 mole) of cesium carbonate and 0.13 g (0.0009 mole) of iodomethane in 1 mL of dimethylformamide was stirred overnight at ambient temperature and then 2 mL of water was added and the mixture stirred for an additional 10 minutes. A solid formed, which was collected by filtration, to give 2-chloro-9-cyclobutyl-5-methyl-5,7,8,9-tetrahydro-pyrimido[4,5-b][1,4]diazepin-6-one (VII-23), which was used directly in the next step.

step d

To a suspension of the 2-chloro-9-cyclobutyl-5-methyl-5,7,8,9-tetrahydro-pyrimido[4,5-b][1,4]diazepin-6-one (VII-23), obtained in step c, 1 mL of ethanol and 1 mL of 3M hydrochloric acid was added 0.084 g (0.0005 mole) of 1-amino-3-methoxy-benzoic acid. The mixture was heated at 100 degree for 3 hours. The mixture was cooled, diluted with 2 mL of water, and the solid collected by filtration to give 0.020 g of 4-(9-cyclobutyl-5-methyl-6-oxo-6,7,8,9-tetrahydro-5H-pyrimido[4,5-b][1,4]diazepin-2-ylamino)-3-methoxy-benzoic acid (I-23).

EXAMPLE 26

4-(9-Cyclobutyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-24)

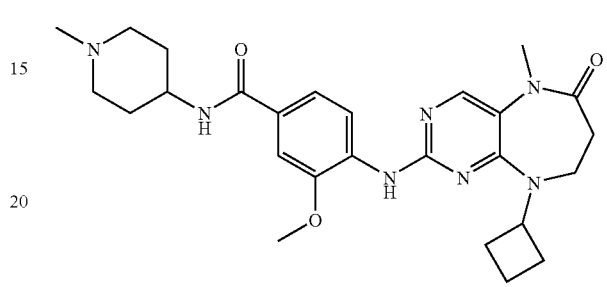

A mixture of 0.059 g (0.00015 mole) of 4-(9-cyclobutyl-5-methyl-6-oxo-6,7,8,9-tetrahydro-5H-pyrimido[4,5-b][1,4]diazepin-2-ylamino)-3-methoxy-benzoic acid (I-23), 0.07 g (0.000185 mole) of 1-[bis(dimethylamino)methylene]-1H-1,2,3-triazolo[4,5-b]pyridinium-3-oxide hexafluorophosphate, 0.05 mL (0.0004 mole) of 4-amino-1-methylpiperidine, 0.1 mL of triethylamine and 3 mL of dichloromethane was stirred for 2.5 hours at ambient temperature. The mixture was concentrated under reduced pressure and the residue purified by C18 reverse phase silica gel chromatography, eluting with an acetonitrile-water gradient (10:90-100:0) to give 0.018 g of 4-(9-cyclobutyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-24).

EXAMPLE 27

9-Cyclobutyl-2-(2-methoxy-phenylamino)-5-methyl-5,7,8,9-tetrahydro-pyrimido[4,5-b][1,4]diazepin-6-one (I-25)

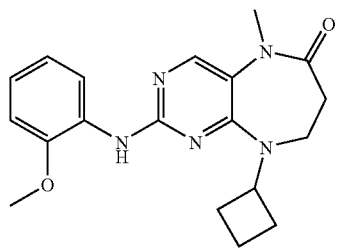

A mixture of 0.23 g (0.00085 mole) of 4-(9-cyclobutyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-24) and 3 mL of 1M hydrochloric acid was heated at 180 degree for 45 minutes in a microwave reactor. The cooled mixture was diluted with 2 mL of water, 3 mL of methanol and 2 mL of acetonitrile and then stirred for 15 minutes. The solids were removed by filtration and the aqueous solution was made basic (pH>10). The solid which formed was collected, washed with water, and then purified by C18 reverse phase silica gel chromatography, eluting with an acetonitrile-water gradient (10:90-100:0) to give 0.037 g of 9-cyclobutyl-2-(2-methoxy-phenylamino)-5-methyl-5,7,8,9-tetrahydro-pyrimido[4,5-b][1,4]diazepin-6-one (I-25)

EXAMPLE 28

(rac)-9-Cyclohexyl-5,7-dimethyl-2-(2-pyridin-4-yl-benzooxazol-5-ylamino)-5,7,8,9-tetrahydro-pyrimido[4,5-b][1,4]diazepin-6-one (I-26)

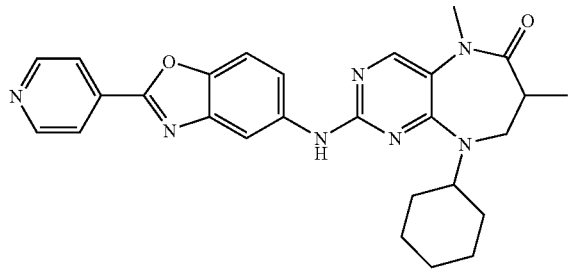

step a

To a solution of 2.03 g (0.00842 mole) of 5-nitro-2-pyridin-4-yl-benzooxazole (R. D. Haugwitz, et al., J. Med. Chem., 1982, 25, 969-74.) in methanol (150 mL) was added 0.2 g of 10% palladium on carbon catalyst. The mixture was hydrogenated on a Parr hydrogenator at 50 psi for 2 hours. The catalyst was filtered off and the solution was concentrated under reduced pressure. The residue was purified by silica gel chromatography, eluting with dichloromethane-methanol (100:0-80:20), to give 0.5 g of 2-pyridin-4-yl-benzooxazol-5-ylamine. HRMS (ES+) m/z Calcd for C12H9N3O+H [(M+H)+]: 212.0819. Found: 212.0818.

step b

A solution of 0.05 g (0.00016 mole) of (rac)-2-chloro-9-cyclohexyl-5,7-dimethyl-5,7,8,9-tetrahydro-pyrimido[4,5-b][1,4]diazepin-6-one (VII-19), 0.034 g, 0.00016 mole) of 2-pyridin-4-yl-benzooxazol-5-ylamine, 0.047 g, (0.00024 mole) of p-toluenesulfonic acid monohydrate and 4 mL of 2-propanol was heated at 180 degree for 2 hours in a microwave reactor. The reaction mixture was concentrated. The residue was diluted with dichloromethane and washed twice with saturated sodium bicarbonate solution. The aqueous phase was extracted with dichloromethane. The combined organic phases were washed with brine, dried anhydrous magnesium sulfate, filtered and concentrated under reduced pressure. The residue was purified by silica gel chromatography, eluting with dichloromethane-methanol (100:0-95:5) to give 0.047 g of (rac)-9-cyclohexyl-5,7-dimethyl-2-(2-pyridin-4-yl-benzooxazol-5-ylamino)-5,7,8,9-tetrahydro-pyrimido[4,5-b][1,4]diaze-pin-6-one (I-26). HRMS (ES+) m/z Calcd for C27H29N7O2+H [(M+H)+]: 484.2456. Found: 484.2456.

EXAMPLE 29

(rac)-4-[5,7-Dimethyl-9-(3-methyl-butyl)-6-oxo-6,7,8,9-tetrahydro-5H-pyrimido[4,5-b][1,4]diazepin-2-ylamino]-3-methoxy-N-(1-methyl-piperidin-4-yl)-benzamide (I-27)

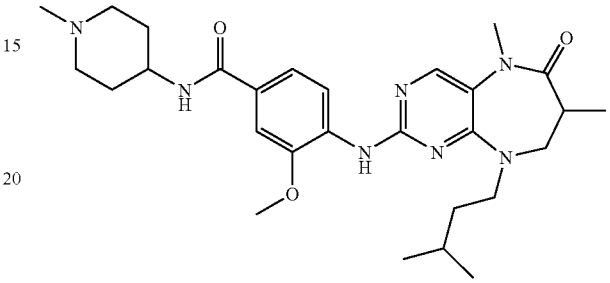

step a

To a mixture of 0.94 g (0.005 mole) of (rac)-2-methyl-3-(3-methyl-butylamino)-propanoic acid methyl ester, 0.97 g (0.005 mole) of 2,4-dichloro-5-nitro-pyrimidine, 25 mL of ethyl acetate and 12.5 mL of water was added 1.5 g (0.015 mole) of potassium bicarbonate. The mixture was stirred for 3 hours, then diluted with 50 mL of ethyl acetate and 50 mL of water. The layers were separated, and the aqueous layer was extracted with twice with 100 mL of ethyl acetate. The organic layers were washed with 100 mL of brine, combined, dried over anhydrous magnesium sulfate, filtered and concentrated under reduced pressure. The residue was purified by silica gel chromatography, eluting with dichloromethane-ethyl acetate (100:0-97:3) to give 1.06 g of (rac)-3-[(2-chloro-5-nitro-pyrimidin-4-yl)-(3-methyl-butyl)-amino]-2-methyl-propanoic acid ethyl ester (IV-27) as a pale yellow oil.

step b

To a solution of 1.06 g (0.0031 mole) of (rac)-3-[(2-chloro-5-nitro-pyrimidin-4-yl)-(3-methyl-butyl)-amino]-2-methyl-propionic acid ethyl ester (IV-27) in 20 mL of acetic acid, was added 1.0 g (0.0179 g-atom) of iron powder. The mixture was heated at 80 degrees for 2 hours and then filtered through Celite while still hot. The filtercake was washed with 100 mL of ethyl acetate (100 mL), and the combined filtrate washed successively with 100 mL of water 100 mL of 7.4 M ammonium hydroxide, 100 mL of water and 100 mL of brine. The aqueous layers were extracted with 100 mL of ethyl acetate, and the combined ethyl acetate layers were dried over anhydrous magnesium sulfate, filtered and concentrated under reduced pressure. The residue was purified by silica gel chromatography, eluting with ethyl acetate—dichloromethane (1:1) to give 0.61 g of (rac)-2-chloro-7-methyl-9-(3-methyl-butyl)-5,7,8,9-tetrahydro-pyrimido[4,5-b][1,4]diazepin-6-one (VI-27) as white crystalline solid.

step c

To a mixture of 0.61 g, (0.00216 mole) of (rac)-2-chloro-7-methyl-9-(3-methyl-butyl)-5,7,8,9-tetrahydro-pyrimido[4,5-b][1,4]diazepin-6-one (VI-27), 0.2 mL (0.00324 mole) of iodomethane and 7 mL of N,N-dimethyl-formamide at 0 degrees, was added 0.13 g (0.00324 mole) of sodium hydride, 60% dispersion in mineral oil. The mixture was stirred at 0 degree for 1.5 hours, and then partitioned between ethyl acetate and water. The aqueous phase was extracted with ethyl acetate. The combined organic phases were washed successively with water and brine, dried over anhydrous magnesium sulfate, filtered and concentrated under reduced pressure. The residue was purified by silica gel chromatography, eluting with hexanes-ethyl acetate (100:0-60:40), to give 0.61 g of (rac)-2-chloro-5,7-dimethyl-9-(3-methyl-butyl)-5,7,8,9-tetrahydro-pyrimido[4,5-b][1,4]diazepin-6-one (VII-27). HRMS (ES+) m/z Calcd for C14H21ClN4O+H [(M+H)+]: 297.1477. Found: 297.1476.

step d

A solution of 0.05 g, (0.00017 mole) of (rac)-2-chloro-5,7-dimethyl-9-(3-methyl-butyl)-5,7,8,9-tetrahydro-pyrimido[4,5-b][1,4]diazepin-6-one (VII-27), 0.044 g, (0.00017 mole) of 4-amino-3-methoxy-N-(1-methyl-piperidin-4-yl)-benzamide, 0.049 g, (0.00026 mole) of p-toluenesulfonic acid monohydrate and 4 mL of 2-propanol was heated at 180 degree for 2 hours in a microwave reactor. The reaction mixture was concentrated under reduced pressure. The residue was diluted with dichloromethane and washed twice with saturated sodium bicarbonate solution. The aqueous phase was extracted with dichloromethane. The combined organic phase was washed with brine, dried over anhydrous magnesium sulfate, filtered and concentrated under reduced pressure. The residue was purified by silica gel chromatography, eluting with dichloromethane-methanol (100:0-75:25) to give 0.049 g of (rac)-4-[5,7-dimethyl-9-(3-methyl-butyl)-6-oxo-6,7,8,9-tetrahydro-5H-pyrimido[4,5-b][1,4]diazepin-2-ylamino]-3-methoxy-N-(1-methyl-piperidin-4-yl)-benzamide (I-27). HRMS (ES+) m/z Calcd for C28H41N7O2+H [(M+H)+]: 524.3344. Found: 524.3342.

EXAMPLE 30

4-(9-Cyclohexyl-6-oxo-6,7,8,9-tetrahydro-5H-pyrimido[4,5-b][1,4]diazepin-2-ylamino)-3-methoxy-N-phenyl-benzamide (I-28)

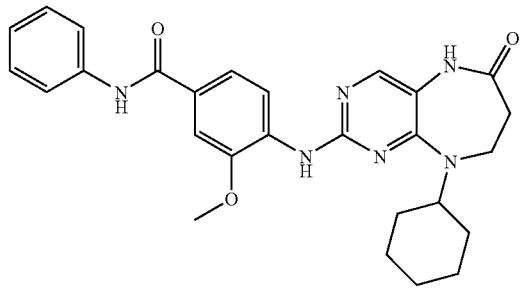

A mixture of 0.25 g (0.00089 mole) of 2-chloro-9-cyclohexyl-5,7,8,9-tetrahydropyrimido[4,5-b][1,4]diazepin-6-one (VI-20), 0.0022 g (0.0013 mole) of 4-amino-3-methoxy-benzoic acid and 3 mL of 1 M hydrochloric acid was heated in a sealed vial at 100 degrees for 1.5 hours. After cooling, the solid was collected by filtration to give 0.235 g of 4-(9-cyclohexyl-6-oxo-6,7,8,9-tetrahydro-5H-pyrimido[4,5-b][1,4]diazepin-2-ylamino)-3-methoxy-benzoic acid (I-28a).

A mixture of 0.04 g (0.000095 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.055 g (0.00015 mole) of 1-[bis(dimethylamino)methylene]-1H-1,2,3-triazolo[4,5-b]pyridinium-3-oxide hexafluorophosphate, 0.014 mL (0.00015 mole) of aniline, 0.04 mL of triethylamine and 2 mL of dichloromethane was stirred overnight at ambient temperature. The mixture was washed with 1 mL of water then with 1.1 mL of 0.34 M sodium hydroxide. The dichloromethane layer was concentrated under reduced pressure, and the residue purified by C18 reverse phase silica gel chromatography, eluting with an acetonitrile-water gradient (10:90-100:0) to give 0.011 g of 4-(9-cyclohexyl-6-oxo-6,7,8,9-tetrahydro-5H-pyrimido[4,5-b][1,4]diazepin-2-ylamino)-3-methoxy-N-phenyl-benzamide (I-28)

EXAMPLE 31

4-(9-Cyclohexyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-29)

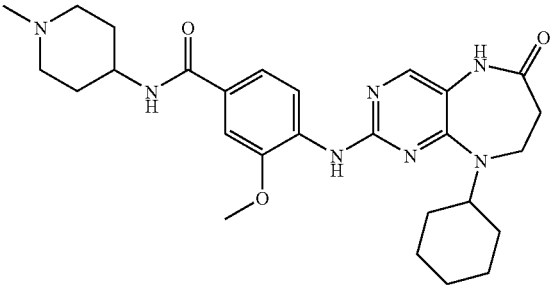

A mixture of 0.04 g (0.000095 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.055 g (0.00015 mole) of 1-[bis(dimethylamino)methylene]-1H-1,2,3-triazolo[4,5-b]pyridinium-3-oxide hexafluorophosphate, 0.017 mL (0.00014 mole) of 4-amino-1-methylpiperidine, 0.04 mL of triethylamine and 2 mL of dichloromethane was stirred overnight at ambient temperature. The mixture was washed with 1 mL of water then with 1.1 mL of 0.34 M sodium hydroxide. The dichloromethane layer was concentrated under reduced pressure, and the residue purified by C18 reverse phase silica gel chromatography, eluting with an acetonitrile-water gradient (10:90-100:0) to give 0.011 g of 4-(9-cyclohexyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-29).

EXAMPLE 32

4-(9-Cyclohexyl-6-oxo-6,7,8,9-tetrahydro-5H-pyrimido[4,5-b][1,4]diazepin-2-ylamino)-3-methoxy-N-propyl-benzamide (I-30)

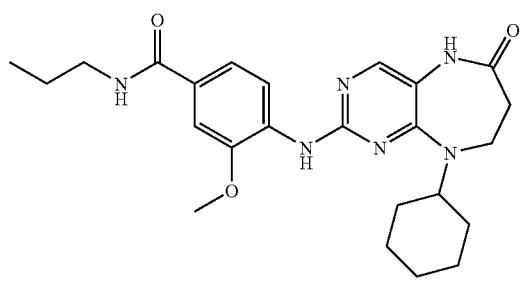

A mixture of 0.04 g (0.000095 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.055 g (0.00015 mole) of 1-[bis(dimethylamino)methylene]-1H-1,2,3-triazolo[4,5-b]pyridinium-3-oxide hexafluorophosphate, 0.015 mL (0.00018 mole) of propylamine, 0.04 mL of triethylamine and 2 mL of dichloromethane was stirred overnight at ambient temperature. The mixture was washed with 1 mL of water then with 1.1 mL of 0.34 M sodium hydroxide. The dichloromethane layer was concentrated under reduced pressure, and the residue purified by C18 reverse phase silica gel chromatography, eluting with an acetonitrile-water gradient (10:90-100:0) to give 0.028 g of 4-(9-cyclohexyl-6-oxo-6,7,8,9-tetrahydro-5H-pyrimido[4,5-b][1,4]diazepin-2-ylamino)-3-methoxy-N-propyl-benzamide (I-30).

EXAMPLE 33

9-Cyclohexyl-2-[2-methoxy-4-(morpholine-4-carbonyl)-phenylamino]-5,7,8,9-tetrahydro-pyrimido[4,5-b][1,4]diazepin-6-one (I-31)

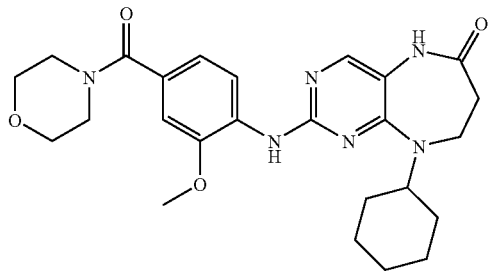

A mixture of 0.04 g (0.000095 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.055 g (0.00015 mole) of 1-[bis(dimethylamino)methylene]-1H-1,2,3-triazolo[4,5-b]pyridinium-3-oxide hexafluorophosphate, 0.015 mL (0.00017 mole) of morpholine, 0.04 mL of triethylamine and 2 mL of dichloromethane was stirred overnight at ambient temperature. The mixture was washed with 1 mL of water then with 1.1 mL of 0.34 M sodium hydroxide. The dichloromethane layer was concentrated under reduced pressure, and the residue purified by C18 reverse phase silica gel chromatography, eluting with an acetonitrile-water gradient (10:90-100:0) to give 0.0069 g of 9-cyclohexyl-2-[2-methoxy-4-(morpholine-4-carbonyl)-phenylamino]-5,7,8,9-tetrahydro-pyrimido[4,5-b][1,4]diazepin-6-one (I-31)

EXAMPLE 34

9-Cyclohexyl-2-[2-methoxy-4-(piperidine-1-carbonyl)-phenylamino]-5,7,8,9-tetrahydro-pyrimido[4,5-b][1,4]diazepin-6-one (I-32)

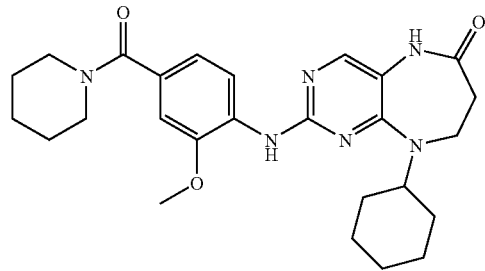

A mixture of 0.04 g (0.000095 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.055 g (0.00015 mole) of 1-[bis(dimethylamino)methylene]-1H-1,2,3-triazolo[4,5-b]pyridinium-3-oxide hexafluorophosphate, 0.015 mL (0.00015 mole) of piperidine, 0.04 mL of triethylamine and 2 mL of dichloromethane was stirred overnight at ambient temperature. The mixture was washed with 1 mL of water then with 1.1 mL of 0.34 M sodium hydroxide. The dichloromethane layer was concentrated under reduced pressure, and the residue purified by C18 reverse phase silica gel chromatography, eluting with an acetonitrile-water gradient (10:90-100:0) to give 0.0170 g of 9-cyclohexyl-2-[2-methoxy-4-(piperidine-1-carbonyl)-phenylamino]-5,7,8,9-tetrahydro-pyrimido[4,5-b][1,4]diazepin-6-one (I-32).

EXAMPLE 35

4-(9-Cyclohexyl-6-oxo-6,7,8,9-tetrahydro-5H-pyrimido[4,5-b][1,4]diazepin-2-ylamino)-3-methoxy-N-(tetrahydro-pyran-4-yl)-benzamide (I-33)

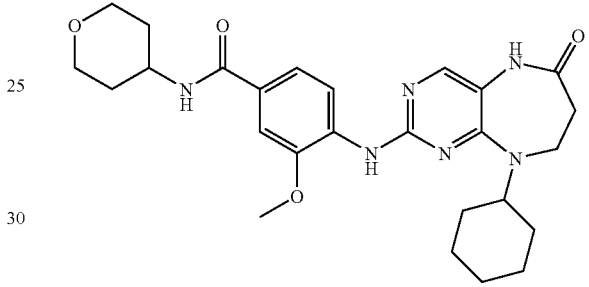

A mixture of 0.04 g (0.000095 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.055 g (0.00015 mole) of 1-[bis(dimethylamino)methylene]-1H-1,2,3-triazolo[4,5-b]pyridinium-3-oxide hexafluorophosphate, 0.015 mL (0.00015 mole) of tetrahydro-pyran-4-ylamine, 0.04 mL of triethylamine and 2 mL of dichloromethane was stirred overnight at ambient temperature. The mixture was washed with 1 mL of water then with 1.1 mL of 0.34 M sodium hydroxide. The dichloromethane layer was concentrated under reduced pressure, and the residue purified by C18 reverse phase silica gel chromatography, eluting with an acetonitrile-water gradient (10:90-100:0) to give 0.015 g of 4-(9-cyclohexyl-6-oxo-6,7,8,9-tetrahydro-5H-pyrimido[4,5-b][1,4]diazepin-2-ylamino)-3-methoxy-N-(tetrahydro-pyran-4-yl)-benzamide (I-33).

EXAMPLE 36

4-(9-Cyclobutyl-5-methyl-6-oxo-6,7,8,9-tetrahydro-5H-pyrimido[4,5-b][1,4]diazepin-2-ylamino)-3-methoxy-benzamide (I-34)

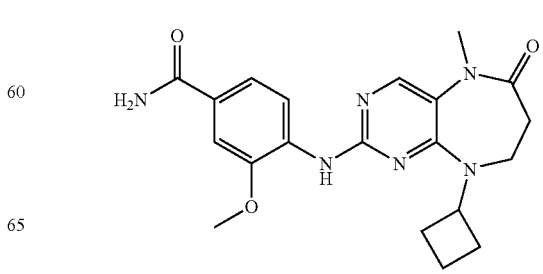

A mixture of 0.047 g (0.00012 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.050 g (0.00013 mole) of 1-[bis(dimethylamino)methylene]-1H-1,2,3-triazolo[4,5-b]pyridinium-3-oxide hexafluorophosphate, 0.1 g (0.0019 mole) of ammonium chloride, 0.15 mL of triethylamine and 2 mL of dichloromethane was stirred overnight at ambient temperature. The mixture was diluted with 3 mL of dichloromethane, washed with 2.5 mL of 0.2 M sodium hydroxide. The dichloromethane layer was concentrated under reduced pressure, and the residue purified by C18 reverse phase silica gel chromatography, eluting with an acetonitrile-water gradient (10:90-100:0) to give 0.036 g of 4-(9-cyclobutyl-5-methyl-6-oxo-6,7,8,9-tetrahydro-5H-pyrimido[4,5-b][1,4]diazepin-2-ylamino)-3-methoxy-benzamide (I-34)

EXAMPLE 37

4-(9-Cyclobutyl-5-methyl-6-oxo-6,7,8,9-tetrahydro-5H-pyrimido[4,5-b][1,4]diazepin-2-ylamino)-3-methoxy-N,N-dimethyl-benzamide (I-35)

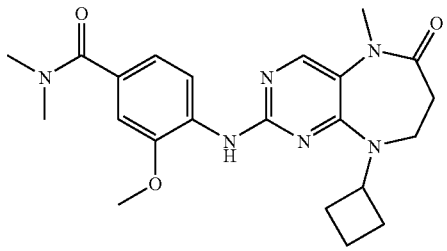

A mixture of 0.047 g (0.00012 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.050 g (0.00013 mole) of 1-[bis(dimethylamino)methylene]-1H-1,2,3-triazolo[4,5-b]pyridinium-3-oxide hexafluorophosphate, 0.1 mL (0.0002 mole) of 2M dimethylamine in tetrahydrofuran, 0.075 mL of triethylamine and 2 mL of dichloromethane was stirred overnight at ambient temperature. The mixture was diluted with 3 mL of dichloromethane, washed with 2.5 mL of 0.2 M sodium hydroxide. The dichloromethane layer was concentrated under reduced pressure, and the residue purified by C18 reverse phase silica gel chromatography, eluting with an acetonitrile-water gradient (10:90-100:0) to give 0.033 g of 4-(9-cyclobutyl-5-methyl-6-oxo-6,7,8,9-tetrahydro-5H-pyrimido[4,5-b][1,4]diazepin-2-ylamino)-3-methoxy-N,N-dimethyl-benzamide (I-35)

EXAMPLE 38

4-(9-Cyclobutyl-5-methyl-6-oxo-6,7,8,9-tetrahydro-5H-pyrimido[4,5-b][1,4]diazepin-2-ylamino)-N-(3-imidazol-1-yl-propyl)-3-methoxy-benzamide (I-36)

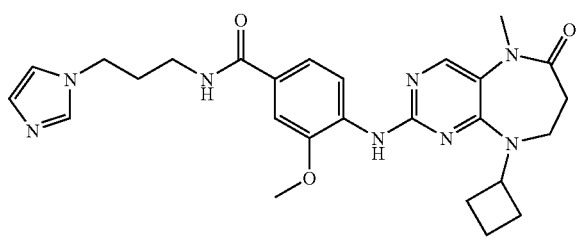

A mixture of 0.047 g (0.00012 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.050 g (0.00013 mole) of 1-[bis(dimethylamino)methylene]-1H-1,2,3-triazolo[4,5-b]pyridinium-3-oxide hexafluorophosphate, 0.05 g (0.0004 mole) of 3-imidazol-1-yl-propylamine, 0.075 mL of triethylamine and 2 mL of dichloromethane was stirred overnight at ambient temperature. The mixture was diluted with 3 mL of dichloromethane, washed with 2.5 mL of 0.2 M sodium hydroxide. The dichloromethane layer was concentrated under reduced pressure, and the residue purified by C18 reverse phase silica gel chromatography, eluting with an acetonitrile-water gradient (10:90-100:0) to give 0.034 g of 4-(9-cyclobutyl-5-methyl-6-oxo-6,7,8,9-tetrahydro-5H-pyrimido[4,5-b][1,4]diazepin-2-ylamino)-N-(3-imidazol-1-yl-propyl)-3-methoxy-benzamide (I-36)

EXAMPLE 39

4-(9-Cyclobutyl-5-methyl-6-oxo-6,7,8,9-tetrahydro-5H-pyrimido[4,5-b][1,4]diazepin-2-ylamino)-3-methoxy-N-pyridin-4-yl-benzamide (I-37)

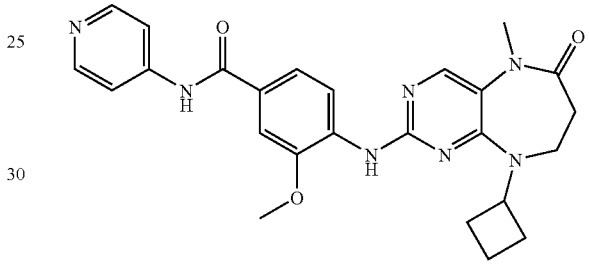

A mixture of 0.047 g (0.00012 mole) of 4-(9-cyclohexyl-6-oxo-6,7,8,9-tetrahydro-5H-pyrimido[4,5-b][1,4]diazepin-2-ylamino)-methoxy-benzoic acid (I-28a), 0.050 g (0.00013 mole) of 1-[bis(dimethylamino)methylene]-1H-1,2,3-triazolo[4,5-b]pyridinium-3-oxide hexafluorophosphate, 0.05 g (0.0005 mole) of 4-aminopyridine, 0.075 mL of triethylamine and 2 mL of dichloromethane was stirred overnight at ambient temperature. The mixture was diluted with 3 mL of dichloromethane, washed with 2.5 mL of 0.2 M sodium hydroxide. The dichloromethane layer was concentrated under reduced pressure, and the residue purified by C18 reverse phase silica gel chromatography, eluting with an acetonitrile-water gradient (10:90-100:0) to give 0.028 g of 4-(9-cyclobutyl-5-methyl-6-oxo-6,7,8,9-tetrahydro-5H-pyrimido[4,5-b][1,4]diazepin-2-ylamino)-3-methoxy-N-pyridin-4-yl-benzamide (I-37)

EXAMPLE 40

4-(9-Cyclopentyl-5,7,7-trimethyl-6-oxo-6,7,8,9-tetrahydro-5H-pyrimido[4,5-b][1,4]diazepin-2-ylamino)-3-methoxy-benzoic acid (I-38)

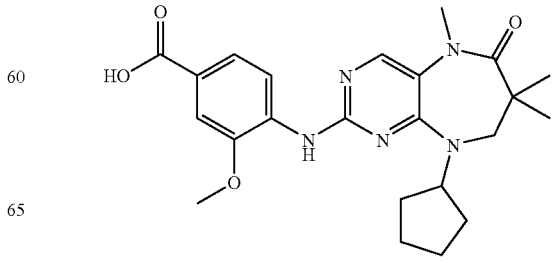

step a

To a mixture of 5.02 g (0.025 mole) of 3-cyclopentylamino-2,2-dimethyl-propanoic acid methyl ester, 5.30 g (0.0276 mole) of 2,4-dichloro-5-nitro-pyrimidine and 100 mL of ether was added 20 mL of water and 5.00 g (0.050 mole) of potassium bicarbonate. The mixture was stirred at room temperature for 14 hours. The resulting two-layer mixture was separated and the aqueous layer was extracted twice with 20 mL of ether. The combined ether extracts were washed successively with 20 mL of aqueous sodium carbonate, twice with 20 mL of brine, dried over anhydrous sodium sulfate, filtered and concentrated under reduced pressure to give 8.60 g of 3-[(2-chloro-5-nitro-pyrimidin-4-yl)-cyclopentyl-amino]-2,2-dimethyl-propanoic acid methyl ester (IV-38) as a yellow solid.

step b

A mixture of 27.32 g (0.0767 mole) of 3-[(2-chloro-5-nitro-pyrimidin-4-yl)-cyclopentyl-amino]-2,2-dimethyl-propanoic acid methyl ester (IV-38), 8.21 g of 5% palladium on carbon catalyst and 700 mL of ethyl acetate was stirred under an atmosphere of hydrogen until the reaction was complete. The resulting mixture was filtered through Celite, washing the filter pad with ethyl acetate, and the filtrate was concentrated under reduced pressure to give 25.33 g of 3-[(5-amino-2-chloro-pyrimidin-4-yl)-cyclopentyl-amino]-2,2-dimethyl-propanoic acid methyl ester (V-38) as a light brown oil.

step c

A solution of 25.33 g of the 3-[(5-amino-2-chloro-pyrimidin-4-yl)-cyclopentyl-amino]-2,2-dimethyl-propanoic acid methyl ester obtained in step c, 600 mL of ethanol and 12 mL of acetic acid was heated at reflux for 8 hours, and then concentrated under reduced pressure. The residue was partitioned between 750 mL of dichloromethane and 250 mL of aqueous sodium carbonate. The aqueous layer was extracted twice with 300 mL of dichloromethane. The combined organic extracts were washed twice with 250 mL of brine, and concentrated under reduced pressure to give 21.76 g of a brown solid. The residue was triturated with 150 mL of ether to give 18.43 g of 2-chloro-9-cyclopentyl-7,7-dimethyl-5,7,8,9-tetrahydro-pyrimido[4,5-b][1,4]diazepin-6-one (VI-38) as a light yellow solid.

step d

To a solution of 18.43 g (0.187 mole) of 2-chloro-9-cyclopentyl-7,7-dimethyl-5,7,8,9-tetrahydro-pyrimido[4,5-b][1,4]diazepin-6-one (VI-38) and 500 mL of dimethylformamide was added 26.6 g (0.187 mole) of iodomethane and 30.6 g (0.0939 mole) of cesium carbonate. The mixture was stirred overnight at ambient temperature. The mixture was then filtered and concentrated under reduced pressure. The residue was partitioned between 500 mL of ethyl acetate and 200 mL of water. The aqueous layer was extracted twice with 200 mL of ethyl acetate. The combined organic extracts were washed with brine, dried over anhydrous sodium sulfate, filtered and concentrated under reduced pressure to give 18.47 g of 2-chloro-9-cyclopentyl-5,7,7-trimethyl-5,7,8,9-tetrahydro-pyrimido[4,5-b][1,4]diazepin-6-one (VII-38) as an off-white solid.

step e

A mixture of 25.26 g (0.0818 mole) 2-chloro-9-cyclopentyl-5,7,7-trimethyl-5,7,8,9-tetrahydro-pyrimido[4,5-b][1,4]diazepin-6-one (VII-38), 15.35 g (0.0900 mole) of 4-amino-3-methoxy-benzoic acid, 300 mL of ethanol and 1200 mL of 1M hydrochloric acid was heated at reflux for 17 hours. The mixture was cooled, and the precipitate which formed was collected by filtration to give 18.7 g of 4-(9-cyclopentyl-5,7,7-trimethyl-6-oxo-6,7,8,9-tetrahydro-5H-pyrimido[4,5-b][1,4]diazepin-2-ylamino)-3-methoxy-benzoic acid (I-38) as white solid.

EXAMPLE 41

4-(9-Cyclopentyl-5,7,7-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-39)

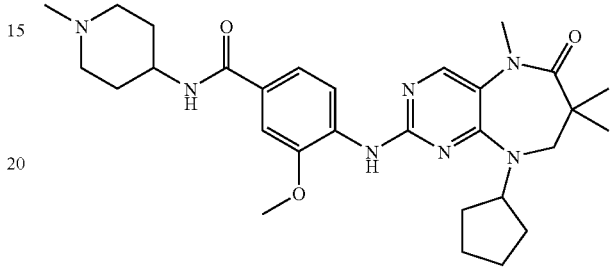

To a suspension of 16.67 g (0.0379 mole) of 4-(9-cyclopentyl-5,7,7-trimethyl-6-oxo-6,7,8,9-tetrahydro-5H-pyrimido[4,5-b][1,4]diazepin-2-ylamino)-3-methoxy-benzoic acid (I-38) in 500 mL of dimethylformamide was added 8.26 g (0.0612 mole) of 1-hydroxybenzotriazole, 22.44 g (0.0592 mole) of 1-[bis(dimethylamino)methylene]-1H-benzotriazolium 3-oxide hexafluorophosphate. The mixture was stirred for 30 minutes and then 6.60 g (0.0580 mole) of 4-amino-1-methylpiperidine was added. The reaction mixture was stirred for an additional and then concentrated under reduced pressure. The residue was partitioned between 800 mL of ethyl acetate and 200 mL of water. The aqueous layer was extracted with twice with 300 mL of ethyl acetate. The combined organic extracts were washed successively three times with 1 M sodium hydroxide, twice with 200 mL of brine, dried over anhydrous sodium sulfate and concentrated under reduced pressure. The residue was purified by silica gel chromatography, eluting with dichloromethane-methanol-isopropylamine (190:10:1-160:40:1) to give 15.32 g of 4-(9-cyclopentyl-5,7,7-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-39).

EXAMPLE 42

3-Methoxy-4-[9-(2-methoxy-ethyl)-5-methyl-6-oxo-6,7,8,9-tetrahydro-5H-pyrimido[4,5-b][1,4]diazepin-2-ylamino]-N-(1-methyl-piperidin-4-yl)-benzamide (I-40)

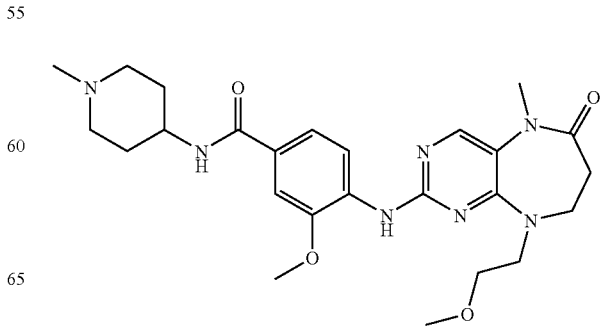

step a

A solution of 2.23 g (0.011 mole) of 3-(2-methoxy-ethylamino)-propanoic acid tert-butyl ester in 20 mL of water was added dropwise to a solution of 1.94 g (0.01 mole) of 2,4-dichloro-5-nitro-pyrimidine in 20 mL of ethyl ether. At 0 degrees, 2.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-85:15) gave 3.3 g of 3-[(2-chloro-5-nitro-pyrimidin-4-yl)-(2-methoxy-ethyl)-amino]-propanoic acid tert-butyl ester (IV-40).

step b

To a solution of 3.3 g (0.0092 mole) of 3-[(2-chloro-5-nitro-pyrimidin-4-yl)-(2-methoxy-ethyl)-amino]-propanoic acid tert-butyl ester (IV-40) in 30 mL of ethanol was added 5.2 g (0.023 mole) of stannous chloride dihydrate and 1 mL of hydrochloric acid. The mixture was heated to 60 degrees for 2 hours and then concentrated under reduced pressure. The residue was taken up in 50 mL of water and extracted with three times with 50 mL of ethyl acetate. The combined organic layers were dried over anhydrous magnesium sulfate, filtered and concentrated under reduced pressure. Purification of the residue by silica gel chromatography, eluting with dichloromethane-methanol (100:0-95:5) gave 0.84 g of 2-chloro-9-(2-methoxy-ethyl)-5,7,8,9-tetrahydro-pyrimido[4,5-b][1,4]diazepin-6-one (VI-40) as a white solid.

step c

To a mixture of 0.102 g (0.0004 mole) of 2-chloro-9-(2-methoxy-ethyl)-5,7,8,9-tetrahydro-pyrimido[4,5-b][1,4]diazepin-6-one (VI-40), 1 mL of N,N-dimethylacetamide and 0.037 mL (0.0006 mole) of iodomethane at 0 degrees was added 0.024 g (0.0006 mole) of 60% sodium hydride in oil. The mixture was stirred at ambient temperature for 1 hour, then 20 mL of water was added. The precipitate was collected by filtration to give 0.087 g of 2-chloro-9-(2-methoxy-ethyl)-5-methyl-5,7,8,9-tetrahydro-pyrimido[4,5-b][1,4]diazepin-6-one (VII-40) as an yellow solid.

step d

A mixture of 0.108 g (0.0004 mole) of 2-chloro-9-(2-methoxy-ethyl)-5-methyl-5,7,8,9-tetrahydro-pyrimido[4,5-b][1,4]diazepin-6-one (VII-40), 0.08 g (0.00048 mole) of 4-amino-3-methoxy-benzoic acid, 0.5 mL of ethanol, 2 mL of water, and 2 drops of hydrochloric acid was heated at 100 degrees overnight. Upon cooling, a precipitate formed which was collected by filtration to give 0.11 g of 3-methoxy-4-[9-(2-methoxy-ethyl)-5-methyl-6-oxo-6,7,8,9-tetrahydro-5H-pyrimido[4,5-b][1,4]diazepin-2-ylamino]-benzoic acid (I-40a) as an off-white solid.

step e

A mixture of 0.11 g (0.00027 mole) of 3-methoxy-4-[9-(2-methoxy-ethyl)-5-methyl-6-oxo-6,7,8,9-tetrahydro-5H-pyrimido[4,5-b][1,4]diazepin-2-ylamino]-benzoic acid (I-40a), 0.115 g (0.0003 mole) of 1-[bis(dimethylamino)-methylene]-1H-1,2,3-triazolo[4,5-b]pyridinium-3-oxide hexafluorophosphate, 0.166 mL (0.00096 mole) of ethyldiisopropyl amine and 2.0 mL of dimethylformamide was stirred for 5 minutes and then 0.047 g (0.00041 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.098 g of 3-methoxy-4-[9-(2-methoxy-ethyl)-5-methyl-6-oxo-6,7,8,9-tetrahydro-5H-pyrimido[4,5-b][1,4]diazepin-2-ylamino]-N-(1-methyl-piperidin-4-yl)-benzamide (I-40) as a white solid.

EXAMPLE 43

(rac)-4-(9-Cyclopentyl-5,7,8-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-41)

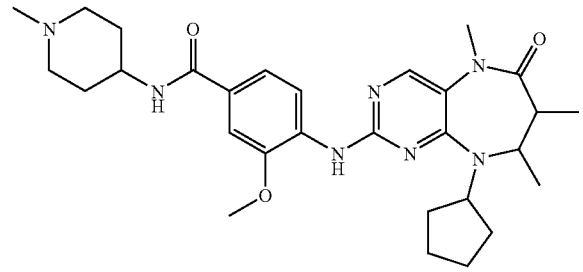

step a

A solution of 1.07 g (0.005 mole) of (rac)-3-cyclopentylamino-2-methyl-butanoic acid ethyl ester in 30 mL of water was added dropwise to a solution of 0.97 g (0.005 mole) of 2,4-dichloro-5-nitro-pyrimidine in 20 mL of ethyl ether. At 0 degrees, 1.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-80:20) gave 1.4 g of (rac)-3-[(2-chloro-5-nitro-pyrimidin-4-yl)-cyclopentyl-amino]-2-methyl-butanoic acid ethyl ester (IV-41).

step b

To a solution of 1.2 g (0.0032 mole) of (rac)-3-[(2-chloro-5-nitro-pyrimidin-4-yl)-cyclopentyl-amino]-2-methyl-butanoic acid ethyl ester (IV-41) in 20 mL of ethanol was added 1.82 g (0.0081 mole) of stannous chloride dihydrate and 0.5 mL of hydrochloric acid. The mixture was heated to 60 degrees for 2 hrs. The mixture was concentrated under reduced pressure. The residue was taken up in 50 mL of water and extracted with three times with 50 mL of ethyl acetate. The combined organics were dried with magnesium sulfate, filtered and concentrated under reduced pressure. Purification of the residue by silica gel chromatography, eluting with dichloromethane-methanol (100:0-95:5) gave 0.36 g of (rac)-2-chloro-9-cyclopentyl-7,8-dimethyl-5,7,8,9-tetrahydro-pyrimido[4,5-b][1,4]diazepin-6-one (VI-41) as a white solid.

step c

To a mixture of 0.09 g (0.0003 mole) of (rac)-2-chloro-9-cyclopentyl-7,8-dimethyl-5,7,8,9-tetrahydro-pyrimido[4,5-b][1,4]diazepin-6-one (VI-41), 1 mL of N,N-dimethylacetamide and 0.028 mL (0.00045 mole) of iodomethane at 0 degrees was added 0.027 g (0.00045 mole) of 60% sodium hydride in oil. The mixture was stirred at ambient temperature for 1 hour, then 20 mL of water was added. The precipitate was collected by filtration to give 0.092 g of (rac)-2-chloro-9-cyclopentyl-5,7,8-trimethyl-5,7,8,9-tetrahydro-pyrimido[4,5-b][1,4]diazepin-6-one (VII-41) as an yellow solid.

step d

A mixture of 0.092 g (0.0003 mole) of (rac)-2-chloro-9-cyclopentyl-5,7,8-trimethyl-5,7,8,9-tetrahydro-pyrimido[4,5-b][1,4]diazepin-6-one (VII-41), 0.1 g (0.00036 mole) of 4-amino-3-methoxy-benzoic acid, 0.5 mL of ethanol, 2 mL of water, and 2 drops of hydrochloric acid was heated at 100 degrees overnight. Upon cooling, a precipitate formed which was collected by filtration to give 0.095 g of (rac)-4-(9-cyclopentyl-5,7,8-trimethyl-6-oxo-6,7,8,9-tetrahydro-5H-pyrimido[4,5-b][1,4]diazepin-2-ylamino)-3-methoxy-benzoic acid (I-41a) as an off-white solid.

step e

A mixture of 0.095 g (0.00022 mole) of (rac)-4-(9-cyclopentyl-5,7,8-trimethyl-6-oxo-6,7,8,9-tetrahydro-5H-pyrimido[4,5-b][1,4]diazepin-2-ylamino)-3-methoxy-benzoic acid (I-41a), 0.90 g (0.00024 mole) of 1-[bis(dimethylamino)methylene]-1H-1,2,3-triazolo[4,5-b]pyridinium-3-oxide hexafluorophosphate, 0.132 mL (0.0076 mole) of ethyldiisopropyl amine and 2.0 mL of dimethylformamide was stirred for 5 minutes and then 0.037 g (0.00033 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (10:90-80:0) to give 0.086 g of (rac)-4-(9-cyclopentyl-5,7,8-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-41) as a white solid.

EXAMPLE 44

(rac)-4-(9-Benzyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-42)

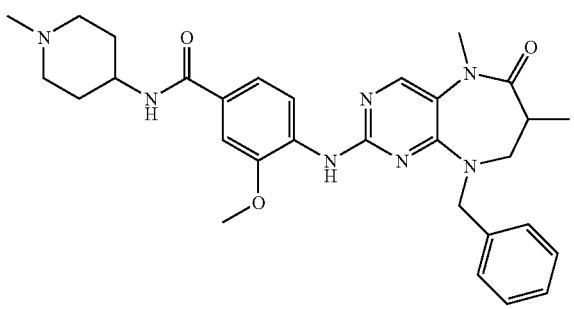

step a

To a mixture of 2.73 g (0.010 mole) of (rac)-3-benzylamino-2-methyl-propanoic acid methyl ester, 1.84 g (0.010 mole) of 2,4-dichloro-5-nitro-pyrimidine, 50 mL of ethyl acetate and 25 mL of water was added 3.0 g (0.030 mole) of potassium bicarbonate. The mixture was stirred for 3 hours, then diluted with 50 mL of ethyl acetate and 50 mL of water.

The layers were separated, and the aqueous layer extracted twice with 100 mL of ethyl acetate. The organic layers were washed with 100 mL of brine, combined, dried over anhydrous magnesium sulfate, filtered and concentrated under reduced pressure. The residue was purified by silica gel chromatography, eluting with dichloromethane-ethyl acetate (100:0-97:3) to give 2.55 g of (rac)-3-[benzyl-(2-chloro-5-nitro-pyrimidin-4-yl)-amino]-2-methyl-propanoic acid methyl ester (IV-42) as pale yellow oil.

step b

To a solution of 2.55 g (0.007 mole) of (rac)-3-[benzyl-(2-chloro-5-nitro-pyrimidin-4-yl)-amino]-2-methyl-propanoic acid methyl ester in 50 mL of acetic acid, was added 2.550 g (0.0457 g-atom) of iron powder. The mixture was heated at 80 degrees for 2 hours, then filtered through Celite while still hot. The filtercake was washed with 200 mL of ethyl acetate, and the combined filtrate washed successively with 200 mL of water, 200 mL of 7.4 M ammonium hydroxide, 200 mL of water and 200 mL of brine. The aqueous layers were extracted with 200 mL of ethyl acetate, and the combined ethyl acetate layers were dried over anhydrous magnesium sulfate, filtered and concentrated under reduced pressure. The residue was recrystallized from dichloromethane—hexanes to give 0.61 g of (rac)-9-benzyl-2-chloro-7-methyl-5,7,8,9-tetrahydro-pyrimido[4,5-b][1,4]diazepin-6-one (VI-42) as off-white crystalline solid.

step c

To an ice cooled mixture of 1.38 g (0.0046 mole) of (rac)-9-benzyl-2-chloro-7-methyl-5,7,8,9-tetrahydro-pyrimido[4,5-b][1,4]diazepin-6-one (VI-42), 0.43 mL (0.0068 mole) of iodomethane and 15 mL of dimethylformamide was added 0.27 g (0.0068 mole) of a 60% oil dispersion of sodium hydride. The mixture was stirred at 0 degrees for 2 hours and then partitioned between ethyl acetate and water. The aqueous phase was extracted with ethyl acetate. The combined organic phases were washed successively with water and brine, dried over anhydrous magnesium sulfate and concentrated under reduced pressure. The residue was purified by silica gel chromatography eluting with hexanes-ethyl acetate (100:0-60:40) to give 1.36 g of (rac)-9-benzyl-2-chloro-5,7-dimethyl-5,7,8,9-tetrahydro-pyrimido[4,5-b][1,4]diazepin-6-one as white powder (VII-42).

HRMS (ES+) m/z Calcd for C16H17ClN4O+H [(M+H)+]: 317.1164. Found: 317.1162.

step d

A solution of 0.050 g (0.00016 mole) of (rac)-9-benzyl-2-chloro-5,7-dimethyl-5,7,8,9-tetrahydro-pyrimido[4,5-b][1,4]diazepin-6-one (VII-42), 0.042 g (0.00016 mole) of 4-amino-3-methoxy-N-(1-methyl-piperidin-4-yl)-benzamide, 0.046 g (0.00024 mole) of p-toluenesulfonic acid monohydrate in 4.0 mL of 2-propanol was heated at 180 degrees for 2 hours in a microwave reactor. The reaction mixture was concentrated under reduced pressure. The residue was diluted with dichloromethane and washed twice with saturated sodium bicarbonate solution. The aqueous phase was extracted with dichloromethane and the combined organic phases washed with brine, dried over anhydrous magnesium sulfate and concentrated under reduced pressure. The residue was purified by silica gel chromatography eluting with dichloromethane-methanol (100:0-75:25) to give 0.0451 g of (rac)-4-(9-benzyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-42) as white powder. HRMS (ES+) m/z Calcd for C30H37N7O3+H [(M+H)+]: 544.3031. Found: 544.3031.

EXAMPLE 45

4-(9-Isopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-43)

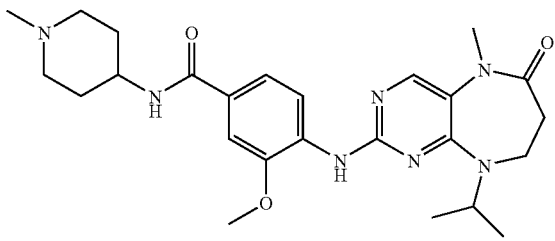

step a

A solution of 0.935 g (0.005 mole) of 3-isopropylamino-propanoic acid tert-butyl ester in 20 mL of water was added dropwise to a solution of 0.97 g (0.005 mole) of 2,4-dichloro-5-nitro-pyrimidine in 20 mL of ethyl ether. At 0 degrees, 1.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-80:20) gave 1.6 g of 3-[(2-chloro-5-nitro-pyrimidin-4-yl)-isopropyl-amino]-propanoic acid tert-butyl ester (IV-43).

step b

A mixture of 1.6 g (0.0045 mole) of 3-[(2-chloro-5-nitro-pyrimidin-4-yl)-isopropyl-amino]-propanoic acid tert-butyl ester (IV-43) in 50 mL of ethyl acetate and 0.5 g of 5% palladium on carbon catalyst was stirred under an atmosphere of hydrogen until hydrogen uptake was complete. The mixture was filtered through a pad of Celite, washing the filter pad with dichloromethane. Concentration of the filtrate under reduced pressure gave 1.4 g of 3-[(5-amino-2-chloro-pyrimidin-4-yl)-isopropyl-amino]-propanoic acid tert-butyl ester (V-43). This material was used directly in the next step without further purification.

step c

A mixture of 50 mL of ethanol, 1 mL of acetic acid and 1.4 g of the 3-[(5-amino-2-chloro-pyrimidin-4-yl)-isopropyl-amino]-propanoic acid tert-butyl ester (V-43), prepared in the previous step, was heated at reflux overnight, and then concentrated under reduced pressure. The residue was taken up in dichloromethane and washed successively with 10% sodium bicarbonate solution, water and then dried over anhydrous sodium sulfate. The mixture was filtered and then concentrated under reduced pressure. Trituration of the residue with ether, provided 0.85 g of 2-chloro-9-isopropyl-5,7,8,9-tetrahydro-pyrimido[4,5-b][1,4]diazepin-6-one (VI-43).

step d

To a mixture of 0.096 g (0.0004 mole) of 2-chloro-9-isopropyl-5,7,8,9-tetrahydro-pyrimido[4,5-b][1,4]diazepin-6-one (VI-43), 1 mL of N,N-dimethylacetamide and 0.037 mL (0.0006 mole) of iodomethane at 0 degrees was added 0.024 g (0.0006 mole) of 60% sodium hydride in oil. The mixture was stirred at ambient temperature for 1 hour, then 20 mL of water was added. The precipitate was collected by filtration to give 0.088 g of 2-chloro-9-isopropyl-5-methyl-5,7,8,9-tetrahydro-pyrimido[4,5-b][1,4]diazepin-6-one (VII-43) as an yellow solid.

step e

A mixture of 0.076 g (0.0003 mole) of 2-chloro-9-isopropyl-5-methyl-5,7,8,9-tetrahydro-pyrimido[4,5-b][1,4]diazepin-6-one (VII-43), 0.060 g (0.00036 mole) of 4-amino-3-methoxy-benzoic acid, 0.5 mL of ethanol, 2 mL of water, and 2 drops of hydrochloric acid was heated at 100 degrees overnight. Upon cooling, a precipitate formed which was collected by filtration to give 0.078 g of 4-(9-isopropyl-5-methyl-6-oxo-6,7,8,9-tetrahydro-5H-pyrimido[4,5-b][1,4]diazepin-2-ylamino)-3-methoxy-benzoic acid (I-43a) as an off-white solid.

step f

A mixture of 0.077 g (0.0002 mole) of 4-(9-isopropyl-5-methyl-6-oxo-6,7,8,9-tetrahydro-5H-pyrimido[4,5-b][1,4]diazepin-2-ylamino)-3-methoxy-benzoic acid (I-43a), 0.091 g (0.00024 mole) of 1-[bis(dimethylamino)methylene]-1H-1,2,3-triazolo[4,5-b]pyridinium-3-oxide hexafluorophosphate, 0.052 mL (0.0003 mole) of ethyldiisopropyl amine and 1.0 mL of dimethylformamide was stirred for 5 minutes and then 0.034 g (0.0003 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.064 g of 4-(9-isopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-43) as a white solid.

EXAMPLE 46

4-(9-Butyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-44)

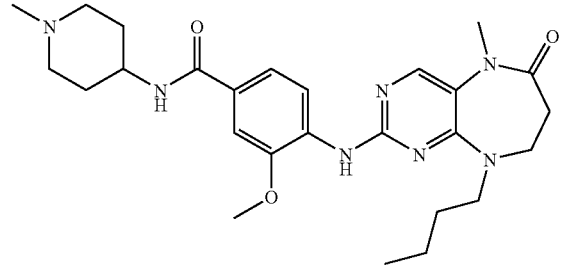

step a

A solution of 1.01 g (0.005 mole) of 3-butylamino-propanoic acid tert-butyl ester in 20 mL of water was added dropwise to a solution of 0.97 g (0.005 mole) of 2,4-dichloro-5-nitro-pyrimidine in 20 mL of ethyl ether. At 0 degrees, 1.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-90:10) gave 1.6 g of 3-[butyl-(2-chloro-5-nitro-pyrimidin-4-yl)-amino]-propionic acid tert-butyl ester (IV-44)

step b

A mixture of 1.6 g (0.0045 mole) of 3-[butyl-(2-chloro-5-nitro-pyrimidin-4-yl)-amino]-propionic acid tert-butyl ester (IV-44) in 50 mL of ethyl acetate and 0.5 g of 5% palladium on carbon catalyst was stirred under an atmosphere of hydrogen until hydrogen uptake was complete. The mixture was filtered through a pad of Celite, washing the filter pad with dichloromethane. Concentration of the filtrate under reduced pressure gave 1.3 g of 3-[(5-amino-2-chloro-pyrimidin-4-yl)-butyl-amino]-propanoic acid tert-butyl ester (V-44). This material was used directly in the next step without further purification.

step c

A mixture of 50 mL of ethanol, 1 mL of acetic acid and 1.3 g of the 3-[(5-amino-2-chloro-pyrimidin-4-yl)-butyl-amino]-propionic acid tert-butyl ester (V-44), prepared in the previous step, was heated at reflux overnight, and then concentrated under reduced pressure. The residue was taken up in dichloromethane and washed successively with 10% sodium bicarbonate solution, water and then dried over anhydrous sodium sulfate. The mixture was filtered and then concentrated under reduced pressure. Trituration of the residue with ether, provided 0.90 g of 9-butyl-2-chloro-5,7,8,9-tetrahydro-pyrimido[4,5-b][1,4]diazepin-6-one (VI-44).

step d

To a mixture of 0.102 g (0.0004 mole) of 9-butyl-2-chloro-5,7,8,9-tetrahydro-pyrimido[4,5-b][1,4]diazepin-6-one (VI-44), 1 mL of N,N-dimethylacetamide and 0.037 mL (0.0006 mole) of iodomethane at 0 degrees was added 0.024 g (0.0006 mole) of 60% sodium hydride in oil. The mixture was stirred at ambient temperature for 1 hour, then 20 mL of water was added. The precipitate was collected by filtration to give 0.094 g of 9-butyl-2-chloro-5-methyl-5,7,8,9-tetrahydro-pyrimido[4,5-b][1,4]diazepin-6-one (VII-44) as an yellow solid.

step e

A mixture of 0.08 g (0.0003 mole) of 9-butyl-2-chloro-5-methyl-5,7,8,9-tetrahydro-pyrimido[4,5-b][1,4]diazepin-6-one (VII-44), 0.060 g (0.00036 mole) of 4-amino-3-methoxy-benzoic acid, 0.5 mL of ethanol, 2 mL of water, and 2 drops of hydrochloric acid was heated at 100 degrees overnight. Upon cooling, a precipitate formed which was collected by filtration to give 0.084 g of 4-(9-butyl-5-methyl-6-oxo-6,7,8,9-tetrahydro-5H-pyrimido[4,5-b][1,4]diazepin-2-ylamino)-3-methoxy-benzoic acid (I-44a) as an off-white solid.

Step f

A mixture of 0.08 g (0.0002 mole) of 4-(9-butyl-5-methyl-6-oxo-6,7,8,9-tetrahydro-5H-pyrimido[4,5-b][1,4]diazepin-2-ylamino)-3-methoxy-benzoic acid (I-44a), 0.091 g (0.00024 mole) of 1-[bis(dimethylamino)methylene]-1H-1,2,3-triazolo[4,5-b]pyridinium-3-oxide hexafluorophosphate, 0.052 mL (0.0003 mole) of ethyldiisopropyl amine and 1.0 mL of dimethylformamide was stirred for 5 minutes and then 0.034 g (0.0003 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.064 g of 4-(9-butyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-44) as a white solid.

EXAMPLE 47

(rac)-4-[5,7-Dimethyl-6-oxo-9-(tetrahydro-pyran-4-yl)-6,7,8,9-tetrahydro-5H-pyrimido[4,5-b][1,4]diazepin-2-ylamino]-3-methoxy-N-(1-methyl-piperidin-4-yl)-benzamide (I-45)

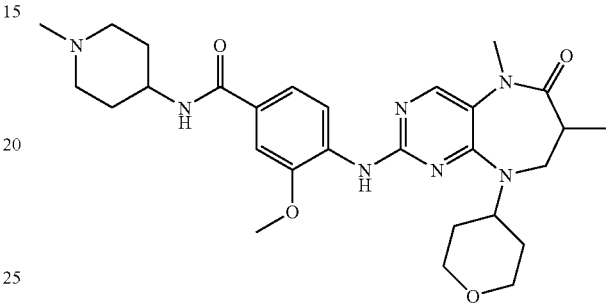

Step a

To a mixture of 2.05 g (0.0095 mole) of (rac)-2-methyl-3-(tetrahydro-pyran-4-ylamino)-propanoic acid ethyl ester, 1.85 g (0.0095 mole) of 2,4-dichloro-5-nitro-pyrimidine 50 mL of ethyl acetate and 25 mL of water was added 2.85 g (0.0286 mole) of potassium bicarbonate. The mixture was stirred for 3 hours and then diluted with 50 mL of ethyl acetate and 50 mL of water. The layers were separated, and the aqueous layer extracted with 100 mL of ethyl acetate. The organic layers were washed with 100 mL of brine, combined, dried over anhydrous magnesium sulfate, filtered and concentrated under reduced pressure. The residue was purified by silica gel chromatography, eluting with hexanes-ethyl acetate (75:25) to give 3.48 g of (rac)-3-[(2-chloro-5-nitro-pyrimidin-4-yl)-(tetrahydro-pyran-4-yl)-amino]-2-methyl-propanoic acid ethyl ester (IV-45) as pale yellow oil.

Step b

To a solution of 3.55 g of (rac)-3-[(2-chloro-5-nitro-pyrimidin-4-yl)-(tetrahydro-pyran-4-yl)-amino]-2-methyl-propanoic acid ethyl ester (IV-45) in 40 mL of acetic acid was added 3.5 g (0.0627 g-atom) of iron powder. The mixture was heated at 80 degrees for 3 hours, and then filtered through Celite while still hot. The filter cake was washed with 100 mL of ethyl acetate and the filtrate was washed successively with 100 mL of water, 100 mL of 7.4 M ammonium 100 mL of water and 100 mL of brine. The aqueous layers were back extracted with 100 mL of ethyl acetate. The ethyl acetate layers were combined, dried over anhydrous magnesium sulfate, filtered and concentrated under reduced pressure. The residue was purified by silica gel chromatography, eluting with dichloromethane-ethyl acetate (40:60-0:100), followed by recrystallization from dichloromethane—hexanes to give 1.63 g of (rac)-2-chloro-7-methyl-9-(tetrahydro-pyran-4-yl)-5,7,8,9-tetrahydro-pyrimido[4,5-b][1,4]diazepin-6-one (VI-45) as white crystalline solid.

Step c

To a cooled mixture of 1.57 g (0.00529 mole) of (rac)-2-chloro-7-methyl-9-(tetrahydro-pyran-4-yl)-5,7,8,9-tetrahydro-pyrimido[4,5-b][1,4]diazepin-6-one (VI-45), 0.49 mL (0.00794 mole) of iodomethane and 15 mL of N,N-dimethylformamide at 0 degrees was added 0.32 g (0.00794 mole) of 60% oil dispersion of sodium hydride. The mixture was stirred at 0 degrees for 2 hours and then partitioned between ethyl acetate and water. The aqueous phase was extracted with ethyl acetate. The combined organic phases were washed successively with water and brine, dried over anhydrous magnesium sulfate and concentrated under reduced pressure. The residue was purified by silica gel chromatography, eluting with hexanes-ethyl acetate (100:0-60:40) to give 1.64 g of (rac)-2-chloro-5,7-dimethyl-9-(tetrahydro-pyran-4-yl)-5,7,8,9-tetrahydro-pyrimido[4,5-b][1,4]diazepin-6-one (VII-45) as white powder. HRMS (ES+) m/z Calcd for C14H19ClN4O2+H [(M+H)$^+$]: 311.1270. Found: 311.1269.

Step d

A solution of 0.050 g (0.00016 mole) of (rac)-2-chloro-5,7-dimethyl-9-(tetrahydropyran-4-yl)-5,7,8,9-tetrahydro-pyrimido[4,5-b][1,4]diazepin-6-one (VII-45), 0.042 g (0.00016 mole) of 4-amino-3-methoxy-N-(1-methyl-piperidin-4-yl)-benzamide, 0.047 g (0.00024 mole) of p-toluenesulfonic acid monohydrate and 4.0 mL of 2-propanol was heated at 180 degrees for 2 hours in a microwave reactor. The reaction mixture was concentrated and the residue diluted with dichloromethane, washed twice with saturated sodium bicarbonate solution. The aqueous phase was extracted with dichloromethane, and the combined organic phases were washed with brine, dried over anhydrous magnesium sulfate and concentrated under reduced pressure. The residue was purified by silica gel chromatography eluting with dichloromethane-methanol (100:0-75:25) to give 0.0483 g of (rac)-4-(5,7-dimethyl-6-oxo-9-(tetrahydro-pyran-4-yl)-6,7,8,9-tetrahydro-5H-pyrimido[4,5-b][1,4]diazepin-2-ylamino)-3-methoxy-N-(1-methyl-piperidin-4-yl)-benzamide (I-45) as a white powder. HRMS (ES+) m/z Calcd for C28H39N7O4+H [(M+H)$^+$]: 538.3137. Found: 538.3136.

EXAMPLE 48

(rac)-4-(9-Cyclopropyl-5,7,8-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-46)

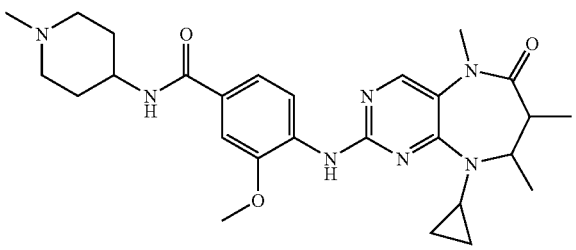

Step a

A solution of 0.93 g (0.005 mole) of (rac)-3-cyclopropylamino-2-methyl-butanoic acid ethyl ester in 20 mL of water was added dropwise to a solution of 0.97 g (0.005 mole) of 2,4-dichloro-5-nitro-pyrimidine in 20 mL of ethyl ether. At 0 degrees, 1.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-80:20) gave 1.4 g of (rac)-3-[(2-chloro-5-nitro-pyrimidin-4-yl)-cyclopropyl-amino]-2-methyl-butanoic acid ethyl ester (IV-46).

Step b

A mixture of 1.02 g (0.003 mole) of (rac)-3-[(2-chloro-5-nitro-pyrimidin-4-yl)-cyclopropyl-amino]-2-methyl-butanoic acid ethyl ester (IV-46) in 30 mL of ethyl acetate and 0.5 g of 5% palladium on carbon catalyst was stirred under an atmosphere of hydrogen until hydrogen uptake was complete. The mixture was filtered through a pad of Celite, washing the filter pad with dichloromethane. Concentration of the filtrate under reduced pressure gave 0.68 g of (rac)-3-[(5-amino-2-chloro-pyrimidin-4-yl)-cyclopropyl-amino]-2-methyl-butanoic acid ethyl ester (V-46). This material was used directly in the next step without further purification.

Step c

A mixture of 50 mL of ethanol, 1 mL of acetic acid and 0.616 g of the (rac)-3-[(5-amino-2-chloro-pyrimidin-4-yl)-cyclopropyl-amino]-2-methyl-butyric acid ethyl ester (V-46), prepared in the previous step, was heated at reflux overnight, and then concentrated under reduced pressure. The residue was taken up in dichloromethane and washed successively with 10% sodium bicarbonate solution, water and then dried over anhydrous sodium sulfate. The mixture was filtered and then concentrated under reduced pressure. Trituration of the residue with ether, provided 0.468 g of (rac)-2-chloro-9-cyclopropyl-7,8-dimethyl-5,7,8,9-tetrahydro-pyrimido[4,5-b][1,4]diazepin-6-one (VI-46).

Step d

To a mixture of 0.266 g (0.001 mole) of (rac)-2-chloro-9-cyclopropyl-7,8-dimethyl-5,7,8,9-tetrahydro-pyrimido[4,5-b][1,4]diazepin-6-one (VI-46) and 0.093 mL (0.0015 mole) of iodomethane at 0 degrees was added 0.06 g (0.0015 mole) of 60% sodium hydride in oil. The mixture was stirred at ambient temperature for 1 hour, then 20 mL of water was added. The precipitate was collected by filtration to give 0.25 g of (rac)-2-chloro-9-cyclopropyl-5,7,8-trimethyl-5,7,8,9-tetrahydro-pyrimido[4,5-b][1,4]diazepin-6-one (VII-46) as an yellow solid.

Step e

A mixture of 0.14 g (0.0005 mole) of (rac)-2-chloro-9-cyclopropyl-5,7,8-trimethyl-5,7,8,9-tetrahydro-pyrimido[4,5-b][1,4]diazepin-6-one (VII-46), 0.10 g (0.0006 mole) of 4-amino-3-methoxy-benzoic acid, 0.5 mL of ethanol, 2 mL of water, and 2 drops of hydrochloric acid was heated at 100 degrees overnight. Upon cooling, a precipitate formed which was collected by filtration to give 0.145 g of (rac)-4-(9-cyclopropyl-5,7,8-trimethyl-6-oxo-6,7,8,9-tetrahydro-5H-pyrimido[4,5-b][1,4]diazepin-2-ylamino)-3-methoxy-benzoic acid (I-46a) as an off-white solid.

Step f

A mixture of 0.082 g (0.0002 mole) of (rac)-4-(9-cyclopropyl-5,7,8-trimethyl-6-oxo-6,7,8,9-tetrahydro-5H-pyrimido[4,5-b][1,4]diazepin-2-ylamino)-3-methoxy-benzoic acid (I-46a), 0.091 g (0.00024 mole) of 1-[bis(dimethylamino)methylene]-1H-1,2,3-triazolo[4,5-b]pyridinium-3-oxide hexafluorophosphate, 0.052 mL (0.0003 mole) of ethyldiisopropyl amine and 1.0 mL of dimethylformamide was stirred for 5 minutes and then 0.034 g (0.0003 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.075 g of (rac)-4-(9-cyclopropyl-5,7,8-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-46) as a white solid.

EXAMPLE 49

(rac)-N-[5-(9-Cyclopentyl-5,7-dimethyl-6-oxo-6,7,8,9-tetrahydro-5H-pyrimido[4,5-b][1,4]diazepin-2-ylamino)-2-hydroxy-phenyl]-nicotinamide (I-47)

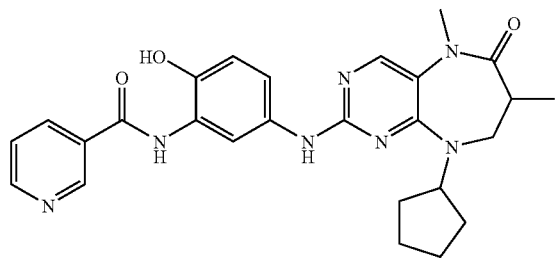

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 50

(rac)-N-[5-(9-Cyclopentyl-5,7-dimethyl-6-oxo-6,7,8,9-tetrahydro-5H-pyrimido[4,5-b][1,4]diazepin-2-ylamino)-2-hydroxy-phenyl]-isonicotinamide (I-48)

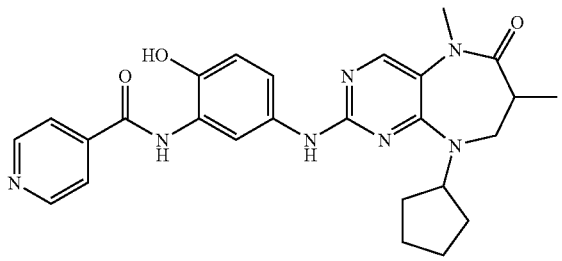

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 51

(rac)-4-[9-Cyclopentyl-7-(2-hydroxy-ethyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide (I-49)

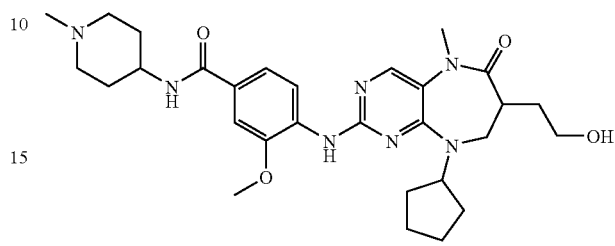

Step a

To a solution of 1.67 g (0.009 mole) of 3-cyclopentylaminomethyl-dihydro-furan-2-one in 25 mL of ethyl ether was added 15 mL of ice-water followed by 1.68 g (0.0087 mole) of 2,4-dichloro-5-nitro-pyrimidine. A solution of 1.36 g (0.014 mole) of potassium bicarbonate in 5 mL of water was added over 20 minutes. The mixture was stirred overnight at ambient temperature. The mixture was concentrated under reduced pressure to remove the ethyl ether and the mixture then filtered, washing with water and then water-acetonitrile. The solid was purified by recrystallization from hexanes-ethyl acetate (1:1) to give 2.2 g of (rac)-3-{[(2-chloro-5-nitro-pyrimidin-4-yl)-cyclopentyl-amino]-methyl}-dihydro-furan-2-one (IV-49).

Step b

A suspension of 0.536 g (0.00157 mole) of (rac)-3-{[(2-chloro-5-nitro-pyrimidin-4-yl)-cyclopentyl-amino]-methyl}-dihydro-furan-2-one (IV-49) in 5 mL of ethyl acetate was added over 1 hour to a mixture of 1.05 g (0.0046 mole) stannous chloride dihydrate, 5 mL ethyl acetate and 0.5 mL of hydrochloric acid at ambient temperature. The mixture was stirred additional 3 hours and then made basic (pH=14) by the addition of 15% sodium hydroxide at 0-5 degrees. The mixture was concentrated under reduced pressure to remove the ethyl, acetate and the residue filtered through a pad of Celite. The solid was then extracted twice with 40 mL of dichloromethane and then 60 mL of ethyl acetate-acetonitrile (3:1). The combined organic extracts were concentrated under reduced pressure to give 0.14 g of (rac)-2-chloro-9-cyclopentyl-7-(2-hydroxy-ethyl)-5,7,8,9-tetrahydro-pyrimido[4,5b][1,4]diazepin-6-one (VI-49).

Step c

A mixture of 0.14 g (0.00045 mole) (rac)-2-chloro-9-cyclopentyl-7-(2-hydroxy-ethyl)-5,7,8,9-tetrahydro-pyrimido[4,5b][1,4]diazepin-6-one (VI-49), 0.294 (0.0009 mole) of cesium carbonate, 0.1 mL (0.0016 mole) of iodomethane and 2 mL of dimethylformamide was stirred for 3 hours at ambient temperature. The mixture was concentrated under reduced pressure. The residue was stirred with 3 mL of water for 15 minutes. The solid, (rac)-2-chloro-9-cyclopentyl-7-(2-hydroxy-ethyl)-5-methyl-5,7,8,9-tetrahydro-pyrimido[4,5-b][1,4]diazepin-6-one (VII-49) was then collected by filtration.

Step d

The solid, (rac)-2-chloro-9-cyclopentyl-7-(2-hydroxy-ethyl)-5-methyl-5,7,8,9-tetrahydro-pyrimido[4,5-b][1,4]diazepin-6-one (VII-49) obtained in the previous step was suspended in 0.7 mL of 1M hydrochloric acid, 0.5 mL of dimethylsulfoxide and 0.5 mL of methanol with 0.098 g (0.00058 mole) of 4-amino-3-methoxybenzoic acid, and heated in a sealed vial at 100 degrees for 2 hours. The mixture concentrated under reduced pressure and the residue dissolved in 3 mL of 15% sodium hydroxide solution and then acidified to pH<1 with 6M hydrochloric acid. A solid formed which was collected by filtration, washing with water, to give 0.047 g (0.0001 mole) of (rac)-4-[9-cyclopentyl-7-(2-hydroxy-ethyl)-5-methyl-6-oxo-6,7,8,9-tetrahydro-5H-pyrimido[4,5-b][1,4]diazepin-2-ylamino]-3-methoxy-benzoic acid (I-49a).

Step e

A mixture of 0.047 g (0.0001 mole) of (rac)-4-[9-cyclopentyl-7-(2-hydroxy-ethyl)-5-methyl-6-oxo-6,7,8,9-tetrahydro-5H-pyrimido[4,5-b][1,4]diazepin-2-ylamino]-3-methoxy-benzoic acid (I-49a), 0.043 g (0.00011 mole) of 1-[bis(dimethylamino)methylene]-1H-1,2,3-triazolo[4,5-b]pyridinium-3-oxide hexafluorophosphate, 0.027 g (0.000023 mole) of 4-amino-1-methylpiperidine, 0.05 mL of triethylamine and 2 mL of dichloromethane was stirred at room temperature for 1.5 hours and then concentrated under reduced pressure. The residue purified by C18 reverse phase silica gel chromatography, eluting with an acetonitrile-water gradient (10:90-100:0) to give 0.0182 g of (rac)-4-[9-cyclopentyl-7-(2-hydroxy-ethyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide (I-49)

EXAMPLE 52

4-(9-Cyclopentyl-5,7,7-trimethyl-6-oxo-6,7,8,9-tetrahydro-5H-pyrimido[4,5-b][1,4]diazepin-2-ylamino)-N-(1-methyl-piperidin-4-yl)-benzamide (I-50)

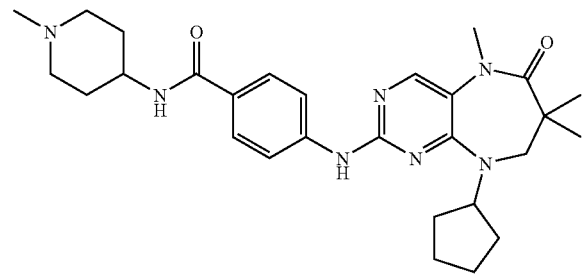

Step a

A mixture of 0.0406 g (0.00013 mole) of 2-chloro-9-cyclopentyl-5,7,7-trimethyl-5,7,8,9-tetrahydro-pyrimido[4,5-b][1,4]diazepin-6-one (VII-38), 0.0191 g (0.000138 mole) of 4-aminobenzoic acid, 0.7 mL of ethanol, 2.8 mL of water and 3 drops of hydrochloric acid was heated at reflux for 17 hours. The mixture was cooled and the white precipitate which formed was collected by filtration to give 0.0315 g of 4-(9-cyclopentyl-5,7,7-trimethyl-6-oxo-6,7,8,9-tetrahydro-5H-pyrimido[4,5-b][1,4]diazepin-2-ylamino)-benzoic acid (I-50a) as a white solid.

Step b

To a suspension of 0.0293 g (0.000072 mole) of 4-(9-cyclopentyl-5,7,7-trimethyl-6-oxo-6,7,8,9-tetrahydro-5H-pyrimido[4,5-b][1,4]diazepin-2-ylamino)-benzoic acid (I-50a) in 3 mL of dimethylformamide was added 0.0156 g (0.00012 mole) of 1-hydroxybenzotriazole, 0.043 g (0.00011 mole) of 1-[bis(dimethylamino)methylene]-1H-benzotriazolium 3-oxide hexafluorophosphate and 0.08 mL (0.0005 mole) of ethyldiisopropylamine. The mixture was stirred for 15 minutes and then 0.0129 g (0.00011 mole) of 4-amino-1-methylpiperidine was added. The mixture was stirred for an additional 2.5 hours and then concentrated under reduced pressure. The residue was dissolved in ethyl acetate and washed successively with 1 M sodium hydroxide, brine, dried over anhydrous sodium sulfate, filtered and concentrated under reduced pressure. The residue was purified by silica gel chromatography, eluting with dichloromethane-methanol (98:2-85:15) to give 0.0181 g of 4-(9-cyclopentyl-5,7,7-trimethyl-6-oxo-6,7,8,9-tetrahydro-5H-pyrimido[4,5-b][1,4]diazepin-2-ylamino)-N-(1-methyl-piperidin-4-yl)-benzamide (I-50).

EXAMPLE 53

(rac)-4-(5,7-Dimethyl-6-oxo-9-phenyl-6,7,8,9-tetrahydro-5H-pyrimido[4,5-b][1,4]diazepin-2-ylamino)-3-methoxy-N-(1-methyl-piperidin-4-yl)-benzamide (I-51)

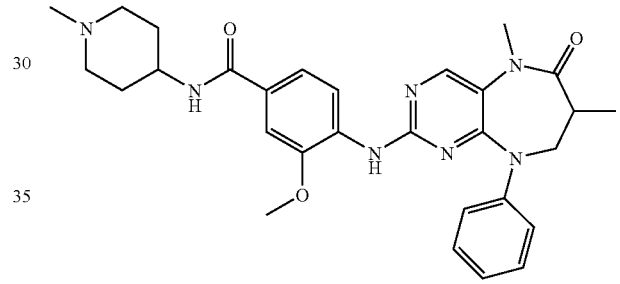

Step a

To a mixture of 1.70 g (0.0082 mole) of (rac)-2-methyl-3-phenylamino-propanoic acid ethyl ester, 1.7 g (0.0088 mole) of 2,4-dichloro-5-nitro-pyrimidine and 60 mL of ethyl acetate, was added 4.24 mL (0.0246 mole) of N,N-diisopropylethylamine. The mixture was stirred at room temperature for 2 hours, and then washed with successively with water and brine, dried over anhydrous magnesium sulfate and concentrated under reduced pressure. The residue was purified by silica gel chromatography eluting with hexanes-ethyl acetate (80:20) to give 2.99 g of (rac)-3-[(2-chloro-5-nitro-pyrimidin-4-yl)-phenyl-amino]-2-methyl-propanoic acid ethyl ester (IV-51) as yellow oil.

Step b

A solution of 1.44 g (0.00395 mole) of (rac)-3-[(2-chloro-5-nitro-pyrimidin-4-yl)-phenyl-amino]-2-methyl-propanoic acid ethyl ester (IV-51), 0.35 g of 10% palladium on carbon and 30 mL of ethyl acetate was stirred under an atmosphere of hydrogen for 1 day. The mixture was filtered, and then concentrated under reduced pressure. The residue was dissolved in 10 mL of a 20:80 mixture acetic acid—ethyl acetate and heated to reflux for 18 hours. The mixture was then cooled, concentrated under reduced pressure. The residue was diluted with dichloromethane and washed twice with saturated sodium bicarbonate and then brine, dried over anhydrous magnesium sulfate and concentrated under reduced pressure.

The residue was washed with hot ethyl acetate and dried to give 0.043 g of (rac)-2-chloro-7-methyl-9-phenyl-5,7,8,9-tetrahydro-pyrimido[4,5-b][1,4]diazepin-6-one (VI-51) as white powder.

Step c

To an ice cooled mixture of 0.46 g (0.0016 mole) of (rac)-2-chloro-7-methyl-9-phenyl-5,7,8,9-tetrahydro-pyrimido[4,5-b][1,4]diazepin-6-one (VI-51), 0.15 mL (0.00239 mole) of iodomethane and 10 mL of dimethylformamide was added 0.10 g (0.00239 mole) of a 60% oil dispersion of sodium hydride. The mixture was stirred at 0 degrees for 2 hours, and then partitioned between ethyl acetate and water. The aqueous phase was extracted with ethyl acetate. The combined organic phases were washed successively with water and brine, dried over anhydrous magnesium sulfate, filtered and concentrated under reduced pressure. The residue was purified by silica gel chromatography eluting with hexanes-ethyl acetate (100:0-60:40) to give 0.30 g of (rac)-2-chloro-5,7-dimethyl-9-phenyl-5,7,8,9-tetrahydro-pyrimido[4,5-b][1,4]diazepin-6-one (VII-51) as white powder. HRMS (ES+) m/z Calcd for C15H15CLN4O+H [(M+H)+]: 303.1007. Found: 303.1006.

Step d

A solution of 0.050 g (0.000165 mole) of (rac)-2-chloro-5,7-dimethyl-9-phenyl-5,7,8,9-tetrahydro-pyrimido[4,5-b][1,4]diazepin-6-one (VII-51), 0.043 g (0.000165 mole) of 4-amino-3-methoxy-N-(1-methyl-piperidin-4-yl)-benzamide, 0.049 (0.00025 mole) of p-toluenesulfonic acid monohydrate and 4.0 mL of 2-propanol (4.0 mL) was heated at 180 degrees for 2 hours in a microwave reactor. The cooled reaction mixture was concentrated under reduced pressure. The residue was diluted with dichloromethane and washed twice with saturated sodium bicarbonate solution. The aqueous phase was extracted with dichloromethane. The combined organic phases were washed with brine, dried over anhydrous magnesium sulfate and concentrated under reduced pressure. The residue was purified by silica gel chromatography, eluting with dichloromethane-methanol (100:0-75:25), to give 0.0526 g of (rac)-4-(5,7-dimethyl-6-oxo-9-phenyl-6,7,8,9-tetrahydro-5H-pyrimido[4,5-b][1,4]diazepin-2-ylamino)-3-methoxy-N-(1-methyl-piperidin-4-yl)-benzamide (I-51) as white powder. HRMS (ES+) m/z Calcd for C29H35N7O3+H [(M+H)+]: 530.2874. Found: 530.2870.

EXAMPLE 54

(rac)-4-(9-Cyclobutyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-52)

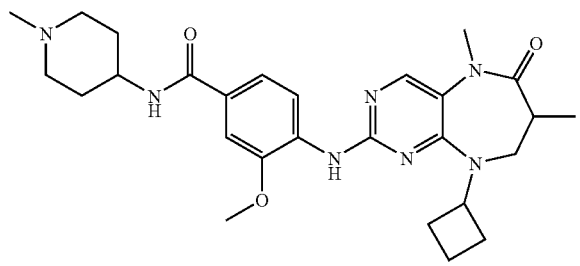

Step a

To a mixture of 1.71 g (0.010 mole) of (rac)-3-cyclobutylamino-2-methyl-propanoic acid methyl ester, 1.94 g (0.010 mole) of 2,4-dichloro-5-nitro-pyrimidine, 50 mL of ethyl acetate and 25 mL of water was added 3.0 g (0.030 mole) of potassium bicarbonate. The mixture was stirred for 3 hours then diluted with 50 mL of ethyl acetate and 50 mL of water. The aqueous layer was extracted with 100 mL of ethyl acetate. The organic layers were washed with 100 mL of brine, combined, dried over anhydrous magnesium sulfate, filtered and concentrated under reduced pressure. The residue was purified by silica gel chromatography, eluting with dichloromethane-ethyl acetate (100:0-97:3) to give 2.54 g of (rac)-3-[(2-chloro-5-nitro-pyrimidin-4-yl)-cyclobutyl-amino]-2-methyl-propanoic acid methyl ester (IV-52) as a pale yellow oil.

Step b

To a solution of 2.54 g (0.0077 mole) of (rac)-3-[(2-chloro-5-nitro-pyrimidin-4-yl)-cyclobutyl-amino]-2-methyl-propanoic acid methyl ester (IV-52) and 40 mL of acetic acid was added 2.5 g (0.0448 g-atom) of iron powder. The mixture was heated at 80 degrees for 3 hours, then filtered through Celite while still hot. The filter cake was washed with 100 mL of ethyl acetate. The filtrate was washed successively with 100 mL of water, 100 mL of 7.4 M ammonium hydroxide, 100 mL of water and 100 mL of brine. The aqueous layers were back extracted with 100 mL of ethyl acetate. The ethyl acetate layers were combined, dried over anhydrous magnesium sulfate, filtered and concentrated under reduced pressure. The residue was recrystallized from dichloromethane—hexanes to give 1.07 g of (rac)-2-chloro-9-cyclobutyl-7-methyl-5,7,8,9-tetrahydro-pyrimido[4,5-b][1,4]diazepin-6-one (VI-52) as white crystalline solid.

Step c

To a mixture of 0.94 g (0.00352 mole) of (rac)-2-chloro-9-cyclobutyl-7-methyl-5,7,8,9-tetrahydro-pyrimido[4,5-b][1,4]diazepin-6-one (VI-52), 0.33 mL (0.00529 mole) of iodomethane and 15 mL of N,N-dimethylformamide at 0 degrees, was added 0.21 g (0.00529 mole) of 60% oil dispersion of sodium hydride. The mixture was stirred at 0 degrees for 2 hours and then partitioned between ethyl acetate and water. The aqueous phase was extracted with ethyl acetate. The combined organic phases were washed successively with water and brine, dried over anhydrous magnesium sulfate, filtered and concentrated under reduced pressure. The residue was purified by silica gel chromatography eluting with hexanes-ethyl acetate (100:0-60:40) to give 0.88 g of (rac)-2-chloro-9-cyclobutyl-5,7-dimethyl-5,7,8,9-tetrahydro-pyrimido[4,5-b][1,4]diazepin-6-one (VII-52) as white powder. HRMS (ES+) m/z Calcd for C13H17CLN4O2+H [(M+H)+]: 281.1164. Found: 281.1163.

Step d

A solution of 0.050 g (0.00018 mole) of (rac)-2-chloro-9-cyclobutyl-5,7-dimethyl-5,7,8,9-tetrahydro-pyrimido[4,5-b][1,4]diazepin-6-one (VII-52), 0.047 g (0.00018 mole) of 4-amino-3-methoxy-N-(1-methyl-piperidin-4-yl)-benzamide, 0.053 g (0.00028 mole) of p-toluenesulfonic acid monohydrate and 4.0 mL of 2-propanol was heated at 180 degrees for 2 hours in a microwave reactor. The reaction mixture was concentrated and the residue diluted with dichloromethane and washed twice with saturated sodium bicarbonate solution. The aqueous phase was extracted with dichloromethane. The combined organic phases were washed with brine, dried over anhydrous magnesium sulfate, filtered and concentrated under reduced pressure. The residue was purified by silica gel chromatography eluting with dichloromethane-methanol (100:0-75:25 n) to give 0.0535 g of (rac)-4-(9-cyclobutyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-52) as white powder. HRMS (ES+) m/z Calcd for C27H37N7O3+H [(M+H)+]: 508.3031. Found: 508.3031.

EXAMPLE 55

4-[(9-Cyclopentyl-6,7,8,9-tetrahydro-5-methyl-6-oxospiro[5H-pyrimido[4,5-b][1,4]diazepine-7,1'-cyclopropan]-2-yl)amino]-3-methoxybenzoic acid (I-53)

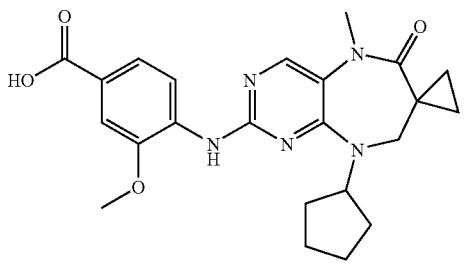

Step a

To a solution of 4.88 g (0.0247 mole) of 1-cyclopentylaminomethyl-cyclopropanecarboxylic acid methyl ester and 4.48 g (0.0231 mole) of 2,4-dichloro-5-nitro-pyrimidine in 100 mL of ether was added 50 mL of water and 4.62 g (0.0462 mole) of potassium bicarbonate. The mixture was stirred at ambient temperature for 5 hours. The resulting two-layer mixture was separated and the aqueous layer was extracted with ether. The combined ether extracts were washed successively with aqueous sodium carbonate and brine, dried over anhydrous sodium sulfate and concentrated under reduced pressure to give 7.80 g of 1-{[(2-chloro-5-nitro-pyrimidin-4-yl)-cyclopentyl-amino]-methyl}-cyclopropanecarboxylic acid methyl ester (IV-53) as a yellow solid.

Step b

A mixture of 2.20 g (0.00679 mole) of 1-{[(2-chloro-5-nitro-pyrimidin-4-yl)-cyclopentyl-amino]-methyl}-cyclopropanecarboxylic acid methyl ester (IV-53), 0.75 g of 5% palladium on carbon catalyst, and 80 mL of ethyl acetate was stirred under an atmosphere of hydrogen until the reaction was complete. The resulting mixture was filtered through Celite and the combined filtrate was concentrated under reduced pressure to give 1.94 g of 1-{[(5-amino-2-chloro-pyrimidin-4-yl)-cyclopentyl-amino]-methyl}-cyclopropanecarboxylic acid methyl ester (V-53) as an off-white solid.

Step c

A mixture of 0.2224 g (0.00068 mole) of 1-{[(5-amino-2-chloro-pyrimidin-4-yl)-cyclopentyl-amino]-methyl}-cyclopropanecarboxylic acid methyl ester (V-53), 12 mL of ethanol and 0.3 mL of acetic acid was heated at reflux for 18 hours, and then concentrated under reduced pressure. The residue was dissolved in 100 mL of ethyl acetate and washed successively twice with 15 mL of aqueous sodium bicarbonate, twice with 15 mL of brine, dried over anhydrous sodium sulfate, filtered and concentrated under reduced pressure to give 0.195 g of 2-chloro-9-cyclopentyl-8,9-dihydro-spiro[5H-pyrimido[4,5-b][1,4]diazepine-7,1'-cyclopropan]-6(7H)-one (VI-53), as a light yellow solid.

Step d

To a solution of 1.00 g (0.0034 mole) of 2-chloro-9-cyclopentyl-8,9-dihydro-spiro[5H-pyrimido[4,5-b][1,4]diazepine-7,1'-cyclopropan]-6(7H)-one (VI-53) in 40 mL of dimethylformamide was added 1.47 g (0.0104 mole) of iodomethane and 1.68 g (0.00575 mole) of cesium carbonate. The mixture was stirred at ambient temperature overnight and then concentrated under reduced pressure. The residue was dissolved in ethyl acetate, washed with brine, dried over anhydrous sodium sulfate, filtered and concentrated under reduced pressure to give 0.957 g of 2-chloro-9-cyclopentyl-8,9-dihydro-5-methylspiro[5H-pyrimido[4,5-b][1,4]diazepine-7,1'-cyclopropan]-6(7H)-one (VII-53) as a white solid.

Step e

A mixture of 0.406 g (0.00133 mole) of 2-chloro-9-cyclopentyl-8,9-dihydro-5-methylspiro[5H-pyrimido[4,5-b][1,4]diazepine-7,1'-cyclopropan]-6(7H)-one (VII-53), 0.237 g (0.00142 mole) of 4-amino-3-methoxylbenzoic acid, 7 mL of ethanol, 28 mL of water and 1.2 mL of hydrochloric acid was heated at reflux for 17 hours. The mixture was cooled, and the precipitate which formed was collected by filtration to give 0.250 g of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methoxybenzoic acid (I-53) as a white solid.

EXAMPLE 56

4-[(9-Cyclopentyl-6,7,8,9-tetrahydro-5-methyl-6-oxospiro[5H-pyrimido[4,5-b][1,4]diazepine-7,1'-cyclopropan]-2-yl)amino]-3-methoxy-N-(1-methyl-4-piperidinyl)benzamide (I-54)

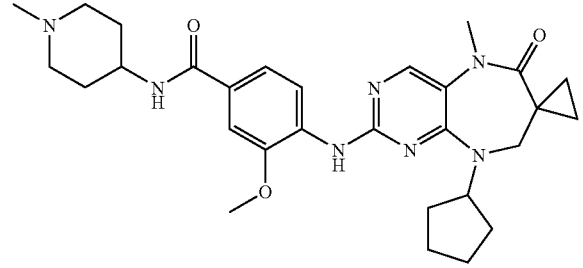

To a suspension of 0.2463 g (0.000563 mole) of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methoxybenzoic acid (I-53) in 15 mL of dimethylformamide was added 0.1222 g (0.00091 mole) of 1-hydroxybenzotriazole, 0.3307 g (0.00087 mole) of 1-[bis(dimethylamino)methylene]-1H-benzotriazolium 3-oxide hexafluorophosphate and 0.59 mL (0.00339 mole) of ethyldiisopropylamine. The mixture was stirred for 20 minutes and then 0.0980 g (0.00086 mole) of 4-amino-1-methylpiperidine was added. The mixture was stirred for an additional 2.5 hours and then concentrated under reduced pressure. The residue was dissolved in ethyl acetate and washed successively with 1 M sodium hydroxide, brine, dried over anhydrous sodium sulfate, filtered and concentrated under reduced pressure. The residue was purified by silica gel chromatography, eluting with dichloromethane-methanol (98:2-80:20)

to give 0.166 g of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methoxy-N-(1-methyl-4-piperidinyl)benzamide (I-54).

EXAMPLE 57

(rac)-4-(9-Cyclopentylmethyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-55)

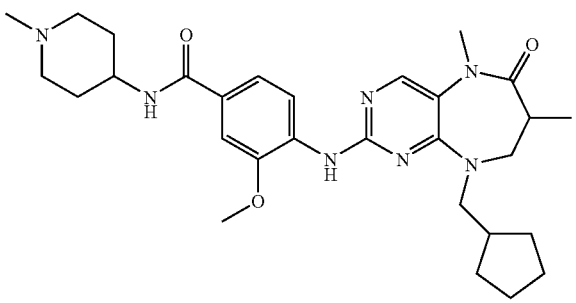

Step a

To a mixture of 2.55 g (0.012 mole) of (rac)-3-(cyclopentyl-methyl-amino)-2-methyl-propanoic acid ethyl ester, 2.32 g (0.012 mole) of 2,4-dichloro-5-nitro-pyrimidine, 75 mL of ethyl acetate and 50 mL of water was added 3.6 g (0.036 mole) of potassium bicarbonate. The mixture was stirred for 3 hours, then diluted with 50 mL of ethyl acetate and 50 mL of water. The aqueous layer was extracted with 100 mL of ethyl acetate. The organic layers were washed with 100 mL of brine, combined, dried over anhydrous magnesium sulfate, filtered and concentrated under reduced pressure. The residue was purified by silica gel chromatography, eluting with dichloromethane-ethyl acetate (100:0-97:3) to give 2.92 g of (rac)-3-[(2-chloro-5-nitro-pyrimidin-4-yl)-cyclopentylm-ethyl-amino]-2-methyl-propanoic acid ethyl ester (IV-55) as pale yellow oil.

Step b

To a solution of 2.18 g (0.0059 mole) of (rac)-3-[(2-chloro-5-nitro-pyrimidin-4-yl)-cyclopentylmethyl-amino]-2-methyl-propanoic acid ethyl ester in 40 mL of acetic acid was added 2.0 g (0.0358 g-atom) of iron powder. The mixture was heated at 80 degrees for 2.5 hours, and then filtered through Celite while still hot. The filter cake was washed with 100 mL of ethyl acetate. The filtrate was washed successively with 100 mL of water, 100 mL of 7.4 M ammonium hydroxide, 100 mL of water and 100 mL of brine. The aqueous layers were back extracted with 100 mL of ethyl acetate. The ethyl acetate layers were combined, dried, dried over anhydrous magnesium sulfate, filtered and concentrated under reduced pressure. The residue was recrystallized from dichloromethane—hexanes to give 1.16 g of (rac)-2-chloro-9-cyclopentylmethyl-7-methyl-6-methylene-6,7,8,9-tetrahydro-5H-pyrimido[4,5-b][1,4]diazepine (VI-55) as light brown crystalline solid.

Step c

To a mixture of 1.10 g (0.00373 mole) of (rac)-2-chloro-9-cyclopentylmethyl-7-methyl-5,7,8,9-tetrahydro-pyrimido [4,5-b][1,4]diazepin-6-one (VI-55), 0.35 mL (0.0056 mole) of iodomethane and 15 mL of N,N-dimethyl-formamide at 0 degrees, was added 0.22 g (0.0056 mole) of 60% oil dispersion of sodium hydride. The mixture was stirred at 0 degrees for 2 hours, then partitioned between ethyl acetate and water. The aqueous phase was extracted with ethyl acetate. The combined organic phases were washed with water and brine, dried over anhydrous magnesium sulfate and concentrated under reduced pressure. The residue was purified by silica gel chromatography eluting with hexanes-ethyl acetate (100:0-60:60) to give 1.10 g of (rac)-2-chloro-9-cyclopentylmethyl-5,7-dimethyl-5,7,8,9-tetrahydro-pyrimido[4,5-b][1,4]diazepin-6-one (VII-55) as white powder. HRMS (ES+) m/z Calcd for C15H21ClN4O+H [(M+H)+]: 309.1477. Found: 309.1476.

Step d

A solution of 0.050 g (0.00016 mole) of (rac)-2-chloro-9-cyclopentylmethyl-5,7-dimethyl-5,7,8,9-tetrahydro-pyrimido[4,5-b][1,4]diazepin-6-one (VII-55), 0.050 g (0.00016 mole) of 4-amino-3-methoxy-N-(1-methyl-piperidin-4-yl)-benzamide, 0.047 g (0.00016 mole) of p-toluenesulfonic acid monohydrate and 4.0 mL of 2-propanol was heated at 180 degrees for 2 hours in a microwave reactor. The reaction mixture was concentrated under reduced pressure. The residue was diluted with dichloromethane and washed twice with saturated sodium bicarbonate solution. The aqueous phases were extracted with dichloromethane. The combined organic phases were washed with brine, dried over anhydrous magnesium sulfate, filtered and concentrated under reduced pressure. The residue was purified by silica gel chromatography eluting with dichloromethane-methanol (100:0-75:25) to give 0.048 g of (rac)-4-(9-cyclopentylmethyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-55) as white powder. HRMS (ES+) m/z Calcd for C29H41N7O3+H [(M+H)+]: 536.3344. Found: 536.3344.

EXAMPLE 58

4-(9-Cyclopentyl-5,7,7-trimethyl-6-oxo-6,7,8,9-tetrahydro-5H-pyrimido[4,5-b][1,4]diazepin-2-ylamino)-3-methyl-N-(1-methyl-piperidin-4-yl)-benzamide (I-56)

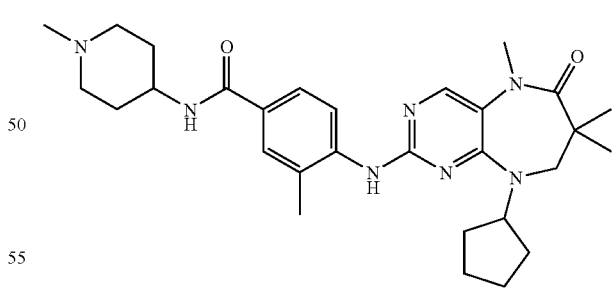

Step a

A mixture of 0.0398 g (0.00013 mole) of 2-chloro-9-cyclopentyl-5,7,7-trimethyl-5,7,8,9-tetrahydro-pyrimido[4,5-b][1,4]diazepin-6-one (VII-38), 0.022 g (0.000143 mole) of 4-amino-3-methylbenzoic acid, 0.7 mL of ethanol, 2.8 mL of water and 3 drops of hydrochloric acid was heated at reflux for 17 hours. The mixture was cooled, and the white precipitate that formed was collected by filtration to give 0.0229 g of 4-(9-cyclopentyl-5,7,7-trimethyl-6-oxo-6,7,8,9-tetrahydro- 5H-pyrimido[4,5-b][1,4]diazepin-2-ylamino)-3-methyl-benzoic acid (I-56a) as a white solid.

Step b

To a suspension of 0.0226 g (0.00005 mole) of 4-(9-cyclopentyl-5,7,7-trimethyl-6-oxo-6,7,8,9-tetrahydro-5H-pyrimido[4,5-b][1,4]diazepin-2-ylamino)-3-methyl-benzoic acid (I-56a) in 3 mL of dimethylformamide was added 0.0121 g (0.00009 mole) of 1-hydroxybenzotriazole, 0.0312 g (0.00008 mole) of 1-[bis(dimethylamino)methylene]-1H-benzotriazolium 3-oxide hexafluorophosphate and 0.06 mL (0.00035 mole) of ethyldiisopropylamine. The mixture was stirred for 15 minutes and then 0.0091 g (0.00008 mole) of 4-amino-1-methylpiperidine was added. The mixture was stirred for an additional 2.5 hours and then concentrated under reduced pressure. The residue was dissolved in ethyl acetate and washed successively with 1 M sodium hydroxide, brine, dried over anhydrous sodium sulfate, filtered and concentrated under reduced pressure. The residue was purified by silica gel chromatography, eluting with dichloromethane-methanol 98:2-85:15) to give 0.0140 g of 4-(9-Cyclopentyl-5,7,7-trimethyl-6-oxo-6,7,8,9-tetrahydro-5H-pyrimido[4,5-b][1,4]diazepin-2-ylamino)-3-methyl-N-(1-methyl-piperidin-4-yl)-benzamide (I-56).

EXAMPLE 59

(rac)-3-Methoxy-4-[5-methyl-9-(2-methyl-cyclopentyl)-6-oxo-6,7,8,9-tetrahydro-5H-pyrimido[4,5-b][1,4]diazepin-2-ylamino]-N-(1-methyl-piperidin-4-yl)-benzamide (I-57)

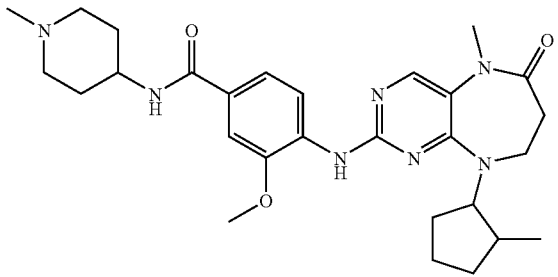

Step a

A solution of 2.2 g (0.011 mole) of (rac)-3-(2-methyl-cyclopentylamino)-propanoic acid ethyl ester in 30 mL of water was added dropwise to a solution of 1.94 g (0.01 mole) of 2,4-dichloro-5-nitro-pyrimidine in 30 mL of ethyl ether. At 0 degrees, 2.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-92:8) gave 3.3 g of (rac)-3-[(2-chloro-5-nitro-pyrimidin-4-yl)-(2-methyl-cyclopentyl)-amino]-propanoic acid ethyl ester (IV-57).

Step b

A mixture of 3.3 g (0.0093 mole) of (rac)-3-[(2-chloro-5-nitro-pyrimidin-4-yl)-(2-methyl-cyclopentyl)-amino]-propanoic acid ethyl ester (IV-57) in 30 mL of ethyl acetate and 0.5 g of 5% palladium on carbon catalyst was stirred under an atmosphere of hydrogen until hydrogen uptake was complete. The mixture was filtered through a pad of Celite, washing the filter pad with dichloromethane. Concentration of the filtrate under reduced pressure gave 2.5 g of (rac)-3-[(5-amino-2-chloro-pyrimidin-4-yl)-(2-methyl-cyclopentyl)-amino]-propanoic acid ethyl ester (V-57). This material was used directly in the next step without further purification.

Step c

A mixture of 50 mL of ethanol, 1 mL of acetic acid and 2.5 g of the (rac)-3-[(5-amino-2-chloro-pyrimidin-4-yl)-(2-methyl-cyclopentyl)-amino]-propanoic acid ethyl ester (V-57) prepared in the previous step was heated at reflux overnight, and then concentrated under reduced pressure. The residue was taken up in dichloromethane and washed successively with 10% sodium bicarbonate solution, and then water and dried over anhydrous sodium sulfate. The mixture was filtered and then concentrated under reduced pressure. Trituration of the residue with ether, provided 1.6 g of (rac)-2-chloro-9-(2-methyl-cyclopentyl)-5,7,8,9-tetrahydro-pyrimido[4,5-b][1,4]diazepin-6-one (VI-57).

Step d

To a mixture of 0.14 g (0.0005 mole) of (rac)-2-chloro-9-(2-methyl-cyclopentyl)-5,7,8,9-tetrahydro-pyrimido[4,5-b][1,4]diazepin-6-one (VI-57), 0.047 mL (0.00075 mole) of iodomethane and 1 mL of N,N-dimethylacetamide at 0 degrees, was added 0.03 g (0.00075 mole) of 60% sodium hydride in oil. The mixture was stirred at ambient temperature for 1 hour, then 20 mL of water was added. The precipitate was collected by filtration to give 0.130 g of (rac)-2-chloro-5-methyl-9-(2-methyl-cyclopentyl)-5,7,8,9-tetrahydro-pyrimido[4,5-b][1,4]diazepin-6-one (VII-57) as a yellow solid.

Step e

A mixture of 0.09 g (0.0003 mole) of (rac)-2-chloro-5-methyl-9-(2-methyl-cyclopentyl)-5,7,8,9-tetrahydro-pyrimido[4,5-b][1,4]diazepin-6-one (VII-57), 0.06 g (0.00036 mole) of 4-amino-3-methoxy-benzoic acid, 0.5 mL of ethanol, 2 mL of water, and 2 drops of hydrochloric acid was heated at 100 degrees overnight. Upon cooling, a precipitate formed which was collected by filtration to give 0.087 g of (rac)-3-methoxy-4-[5-methyl-9-(2-methyl-cyclopentyl)-6-oxo-6,7,8,9-tetrahydro-5H-pyrimido[4,5-b][1,4]diazepin-2-ylamino]-benzoic acid (I-57a) as an off-white solid.

Step f

A mixture of 0.043 g (0.0001 mole) of (rac)-3-methoxy-4-[5-methyl-9-(2-methyl-cyclopentyl)-6-oxo-6,7,8,9-tetrahydro-5H-pyrimido[4,5-b][1,4]diazepin-2-ylamino]-benzoic acid (I-57a), 0.042 g (0.00011 mole) of 1-[bis(dimethylamino)methylene]-1H-1,2,3-triazolo[4,5-b]pyridinium-3-oxide hexafluorophosphate, 0.044 mL (0.00025 mole) of ethyldiisopropyl amine and 1.0 mL of dimethylformamide was stirred for 5 minutes and then 0.017 g (0.00015 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.048 g of (rac)-3-methoxy-4-[5-methyl-9-(2-methyl-cyclopentyl)-6-oxo-6,7,8,9-tetrahydro-5H-pyrimido[4,5-b]

[1,4]diazepin-2-ylamino]-N-(1-methyl-piperidin-4-yl)-benzamide (I-57) as a white solid.

EXAMPLE 60

(rac)-3-Methoxy-4-[5-methyl-9-(3-methyl-cyclopentyl)-6-oxo-6,7,8,9-tetrahydro-5H-pyrimido[4,5-b][1,4]diazepin-2-ylamino]-N-(1-methyl-piperidin-4-yl)-benzamide (I-58)

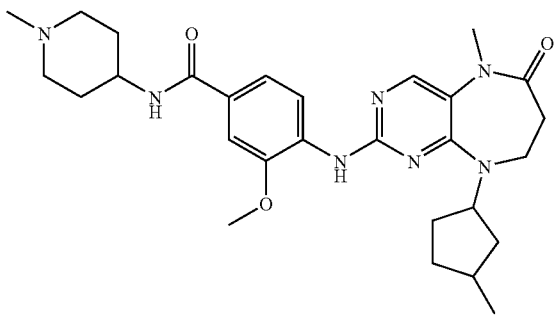

Step a

A solution of 2.2 g (0.011 mole) of (rac)-3-(3-methyl-cyclopentylamino)-propanoic acid ethyl ester in 30 mL of water was added dropwise to a solution of 1.94 g (0.01 mole) of 2,4-dichloro-5-nitro-pyrimidine in 30 mL of ethyl ether. At 0 degrees, 2.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-92:8) gave 3.3 g of (rac)-3-[(2-chloro-5-nitro-pyrimidin-4-yl)-(3-methyl-cyclopentyl)-amino]-propanoic acid ethyl ester (IV-58)

Step b

A mixture of 3.3 g (0.0093 mole) of (rac)-3-[(2-chloro-5-nitro-pyrimidin-4-yl)-(3-methyl-cyclopentyl)-amino]-propanoic acid ethyl ester (IV-58) in 30 mL of ethyl acetate and 0.5 g of 5% palladium on carbon catalyst was stirred under an atmosphere of hydrogen until hydrogen uptake was complete. The mixture was filtered through a pad of Celite, washing the filter pad with dichloromethane. Concentration of the filtrate under reduced pressure gave 2.6 g of (rac)-3-[(5-amino-2-chloro-pyrimidin-4-yl)-(3-methyl-cyclopentyl)-amino]-propanoic acid ethyl ester (V-58). This material was used directly in the next step without further purification.

Step c

A mixture of 50 mL of ethanol, 1 mL of acetic acid and 2.6 g of the (rac)-3-[(5-amino-2-chloro-pyrimidin-4-yl)-(3-methyl-cyclopentyl)-amino]-propanoic acid ethyl ester (V-58) prepared in the previous step was heated at reflux overnight, and then concentrated under reduced pressure. The residue was taken up in dichloromethane and washed successively with 10% sodium bicarbonate solution, and then water and dried over anhydrous sodium sulfate. The mixture was filtered and then concentrated under reduced pressure to the crude product. Trituration of the residue with ether, provided 1.8 g of (rac)-2-chloro-9-(3-methyl-cyclopentyl)-5,7,8,9-tetrahydro-pyrimido[4,5-b][1,4]diazepin-6-one (VI-58).

Step d

To a mixture of 0.14 g (0.0005 mole) of (rac)-2-chloro-9-(3-methyl-cyclopentyl)-5,7,8,9-tetrahydro-pyrimido[4,5-b][1,4]diazepin-6-one (VI-58), 0.047 mL (0.00075 mole) of iodomethane and 1 mL of N,N-dimethylacetamide at 0 degrees, was added 0.03 g (0.00075 mole) of 60% sodium hydride in oil. The mixture was stirred at ambient temperature for 1 hour, then 20 mL of water was added. The precipitate was collected by filtration to give 0.132 g of (rac)-2-chloro-5-methyl-9-(3-methyl-cyclopentyl)-5,7,8,9-tetrahydro-pyrimido[4,5-b][1,4]diazepin-6-one (VII-58) as a yellow solid.

Step e

A mixture of 0.09 g (0.0003 mole) of (rac)-2-chloro-5-methyl-9-(3-methyl-cyclopentyl)-5,7,8,9-tetrahydro-pyrimido[4,5-b][1,4]diazepin-6-one (VII-58), 0.06 g (0.00036 mole) of 4-amino-3-methoxy-benzoic acid, 0.5 mL of ethanol, 2 mL of water, and 2 drops of hydrochloric acid was heated at 100 degrees overnight. Upon cooling, a precipitate formed which was collected by filtration to give 0.095 g of (rac)-3-methoxy-4-[5-methyl-9-(3-methyl-cyclopentyl)-6-oxo-6,7,8,9-tetrahydro-5H-pyrimido[4,5-b][1,4]diazepin-2-ylamino]-benzoic acid (I-58a) as an off-white solid.

Step f

A mixture of 0.043 g (0.0001 mole) of (rac)-3-methoxy-4-[5-methyl-9-(3-methyl-cyclopentyl)-6-oxo-6,7,8,9-tetrahydro-5H-pyrimido[4,5-b][1,4]diazepin-2-ylamino]-benzoic acid (I-58a), 0.042 g (0.00011 mole) of 1-[bis(dimethylamino)methylene]-1H-1,2,3-triazolo[4,5-b]pyridinium-3-oxide hexafluorophosphate, 0.044 mL (0.00025 mole) of ethyldiisopropyl amine and 1.0 mL of dimethylformamide was stirred for 5 minutes and then 0.017 g (0.00015 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.049 g of (rac)-3-methoxy-4-[5-methyl-9-(3-methyl-cyclopentyl)-6-oxo-6,7,8,9-tetrahydro-5H-pyrimido[4,5-b][1,4]diazepin-2-ylamino]-N-(1-methyl-piperidin-4-yl)-benzamide (I-58) as a white solid.

EXAMPLE 61

(rac)-4-[9-(2,2-Dimethyl-cyclopentyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide (I-59)

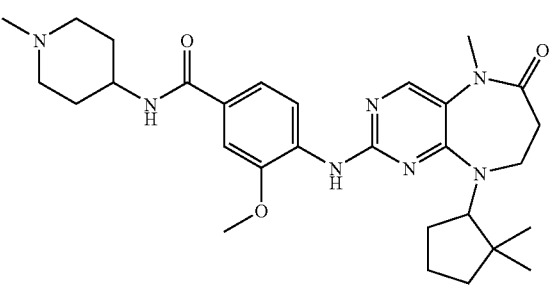

Step a

A solution of 2.2 g (0.011 mole) of (rac)-3-(2,2-dimethyl-cyclopentylamino)-propanoic acid ethyl ester in 30 mL of water was added dropwise to a solution of 1.94 g (0.01 mole) of 2,4-dichloro-5-nitro-pyrimidine in 30 mL of ethyl ether. At 0 degrees, 2.0 g (0.010 mole) of potassium bicarbonate was added. The mixture was stirred at ambient temperature for 3 hours. The layers were then separated, and the aqueous layer extracted twice with 30 mL of ether. The combined organic layers were dried over anhydrous magnesium sulfate, filtered and concentrated under reduced pressure. Purification by silica gel chromatography, eluting with hexanes-ethyl acetate (100:0-92:8) gave 3.3 g of (rac)-3-[(2-chloro-5-nitro-pyrimidin-4-yl)-(2,2-dimethyl-cyclopentyl)-amino]-propanoic acid ethyl ester (IV-59).

Step b

A mixture of 3.3 g (0.0093 mole) of (rac)-3-[(2-chloro-5-nitro-pyrimidin-4-yl)-(2,2-dimethyl-cyclopentyl)-amino]-propionic acid ethyl ester (IV-59) in 30 mL of ethyl acetate and 0.5 g of 5% palladium on carbon catalyst was stirred under an atmosphere of hydrogen until hydrogen uptake was complete. The mixture was filtered through a pad of Celite, washing the filter pad with dichloromethane. Concentration under reduced pressure gave 2.5 g of (rac)-3-[(5-amino-2-chloro-pyrimidin-4-yl)-(2,2-dimethyl-cyclopentyl)-amino]-propanoic acid ethyl ester (V-59). This material was used directly in the next step without further purification.

Step c

A mixture of 50 mL of ethanol, 1 mL of acetic acid and 2.5 g of the (rac)-3-[(5-amino-2-chloro-pyrimidin-4-yl)-(2,2-dimethyl-cyclopentyl)-amino]-propanoic acid ethyl ester (V-59) prepared in the previous step was heated at reflux overnight, and then concentrated under reduced pressure. The residue was taken up in dichloromethane and washed successively with 10% sodium bicarbonate solution, and then water and dried over anhydrous sodium sulfate. The mixture was filtered and then concentrated under reduced pressure. Trituration of the residue with ether, provided 1.6 g of (rac)-2-chloro-9-(2,2-dimethyl-cyclopentyl)-5,7,8,9-tetrahydro-pyrimido[4,5-b][1,4]diazepin-6-one (VI-59).

Step d

To a mixture of 0.14 g (0.0005 mole) of (rac)-2-chloro-9-(2,2-dimethyl-cyclopentyl)-5,7,8,9-tetrahydro-pyrimido[4,5-b][1,4]diazepin-6-one (VI-59), 0.047 mL (0.00075 mole) of iodomethane and 1 mL of N,N-dimethylacetamide at 0 degrees, was added 0.03 g (0.00075 mole) of 60% sodium hydride in oil. The mixture was stirred at ambient temperature for 1 hour, then 20 mL of water was added. The precipitate was collected by filtration to give 0.130 g of (rac)-2-chloro-5-methyl-9-(2,2-dimethyl-cyclopentyl)-5,7,8,9-tetrahydro-pyrimido[4,5-b][1,4]diazepin-6-one (VII-59) as a yellow solid.

Step e

A mixture of 0.09 g (0.0003 mole) of (rac)-2-chloro-5-methyl-9-(2,2-dimethyl-cyclopentyl)-5,7,8,9-tetrahydro-pyrimido[4,5-b][1,4]diazepin-6-one (VII-59), 0.06 g (0.00036 mole) of 4-amino-3-methoxy-benzoic acid, 0.5 mL of ethanol, 2 mL of water, and 2 drops of hydrochloric acid was heated at 100 degrees overnight. Upon cooling, a precipitate formed which was collected by filtration to give 0.087 g of (rac)-3-methoxy-4-[5-methyl-9-(2,2-dimethyl-cyclopentyl)-6-oxo-6,7,8,9-tetrahydro-5H-pyrimido[4,5-b][1,4]diazepin-2-ylamino]-benzoic acid (I-59a) as an off-white solid.

Step f

A mixture of 0.043 g (0.0001 mole) of (rac)-3-methoxy-4-[5-methyl-9-(2,2-dimethyl-cyclopentyl)-6-oxo-6,7,8,9-tetrahydro-5H-pyrimido[4,5-b][1,4]diazepin-2-ylamino]-benzoic acid (I-59a), 0.042 g (0.00011 mole) of 1-[bis(dimethylamino)methylene]-1H-1,2,3-triazolo[4,5-b]pyridinium-3-oxide hexafluorophosphate, 0.044 mL (0.00025 mole) of ethyldiisopropyl amine and 1.0 mL of dimethylformamide was stirred for 5 minutes and then 0.017 g (0.00015 mole) of 4-amino-1-methyl-piperidine was added. The mixture was stirred for 3 hours, then diluted with 10 mL of water plus 2 mL of saturated sodium bicarbonate and then extracted 3 times with 10 mL of ethyl acetate. The combined extracts were washed with brine, dried over anhydrous magnesium sulfate, filtered and concentrated under reduced pressure. The residue was purified by C18 reverse phase silica gel chromatography, eluting with an acetonitrile-water gradient (20:80-100:0) to give 0.048 g of (rac)-3-methoxy-4-[5-methyl-9-(2,2-dimethyl-cyclopentyl)-6-oxo-6,7,8,9-tetrahydro-5H-pyrimido[4,5-b][1,4]diazepin-2-ylamino]-N-(1-methyl-piperidin-4-yl)-benzamide (I-59) as a white solid.

EXAMPLE 62

4-[(9-Cyclopentyl-6,7,8,9-tetrahydro-5-methyl-6-oxospiro[5H-pyrimido[4,5-b][1,4]diazepine-7,1'-cyclopropan]-2-yl)amino]-3-methylbenzoic acid (I-60)

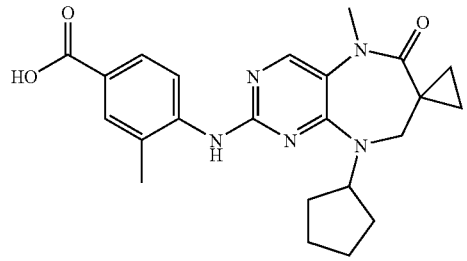

A mixture of 0.0515 g (0.000168 mole) of 2-chloro-9-cyclopentyl-8,9-dihydro-5-methylspiro[5H-pyrimido[4,5-b][1,4]diazepine-7,1'-cyclopropan]-6(7H)-one (VII-53), 0.0283 g (0.000183 mole) of 4-amino-3-methylbenzoic acid, 1 mL of ethanol, 4 mL of water and 4 drops of hydrochloric acid was heated at reflux for 17 hours. The mixture was cooled, and the precipitate which formed was collected by filtration to give 0.029 g of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methylbenzoic acid (I-60) as a white solid.

EXAMPLE 63

4-[(9-Cyclopentyl-6,7,8,9-tetrahydro-5-methyl-6-oxospiro[5H-pyrimido[4,5-b][1,4]diazepine-7,1'-cyclopropan]-2-yl)amino]-3-methyl-N-(1-methyl-4-piperidinyl)benzamide (I-61)

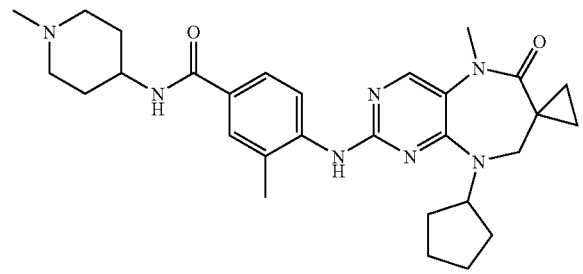

To a suspension of 0.0262 g (0.000062 mole) of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methylbenzoic acid (I-60) in 3 mL of dimethylformamide was added 0.0144 g (0.000107 mole) of 1-hydroxybenzotriazole, 0.0365 g (0.000096 mole) of 1-[bis(dimethylamino)methylene]-1H-benzotriazolium 3-oxide hexafluorophosphate and 0.07 mL (0.000402 mole) of ethyldiisopropylamine. The mixture was stirred for 20 minutes and then 0.012 g (0.0001 mole) of 4-amino-1-methylpiperidine was added. The mixture was stirred for an additional 2.5 hours and then concentrated under reduced pressure. The residue was dissolved in ethyl acetate and washed successively with 1 M sodium hydroxide, brine, dried over anhydrous sodium sulfate, filtered and concentrated under reduced pressure. The residue was purified by silica gel chromatography, eluting with dichloromethane-methanol (98:2-80:20) to give 0.021 g of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methyl-N-(1-methyl-4-piperidinyl)benzamide (I-61)

EXAMPLE 64

4-[(9-Cyclopentyl-6,7,8,9-tetrahydro-5-methyl-6-oxospiro[5H-pyrimido[4,5-b][1,4]diazepine-7,1'-cyclopropan]-2-yl)amino]-N-(1-methyl-4-piperidinyl)benzamide (I-62)

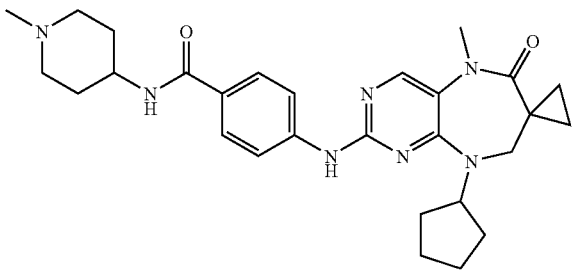

Step a

A mixture of 0.0449 g (0.000146 mole) of 2-chloro-9-cyclopentyl-8,9-dihydro-5-methylspiro[5H-pyrimido[4,5-b][1,4]diazepine-7,1'-cyclopropan]-6(7H)-one (VII-53), 0.0222 g (0.00016 mole) of 4-amino-benzoic acid, 0.8 mL of ethanol, 3.2 mL of water and 3 drops of hydrochloric acid was heated at reflux for 17 hours. The mixture was cooled, and the precipitate which formed was collected by filtration to give 0.029 g of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-benzoic acid (I-62a) as a white solid.

Step b

To a suspension of 0.0275 g (0.0000675 mole) of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-benzoic acid (I-62a) in 3 mL of dimethylformamide was added 0.0157 g (0.000116 mole) of 1-hydroxybenzotriazole, 0.0396 g (0.000104 mole) of 1-[bis(dimethylamino)methylene]-1H-benzotriazolium 3-oxide hexafluorophosphate and 0.07 mL (0.000402 mole) of ethyldiisopropylamine. The mixture was stirred for 20 minutes and then 0.0125 g (0.00011 mole) of 4-amino-1-methylpiperidine was added. The mixture was stirred for an additional 2.5 hours and then concentrated under reduced pressure. The residue was dissolved in ethyl acetate and washed successively with 1 M sodium hydroxide, brine, dried over anhydrous sodium sulfate, filtered and concentrated under reduced pressure. The residue was purified by silica gel chromatography, eluting with dichloromethane-methanol (98:2-80:20) to give 0.026 g of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-N-(1-methyl-4-piperidinyl)benzamide (I-62).

EXAMPLE 65

4-[(9-Cyclopentyl-6,7,8,9-tetrahydro-5-methyl-6-oxospiro[5H-pyrimido[4,5-b][1,4]diazepine-7,1'-cyclopropan]-2-yl)amino]-N-(tetrahydropyran-4-yl)benzamide (I-63)

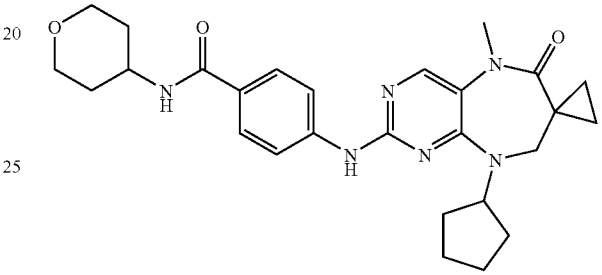

To a suspension of 0.0189 g (0.0000464 mole) of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-benzoic acid (I-62a) in 3 mL of dimethylformamide was added 0.011 g (0.000082 mole) of 1-hydroxybenzotriazole, 0.0275 g (0.000073 mole) of 1-[bis(dimethylamino)methylene]-1H-benzotriazolium 3-oxide hexafluorophosphate and 0.07 mL (0.000402 mole) of ethyldiisopropylamine. The mixture was stirred for 20 minutes and then 0.0125 g (0.00011 mole) of 4-amino-1-methylpiperidine was added. The mixture was stirred for an additional 2.5 hours and then concentrated under reduced pressure. The residue was dissolved in ethyl acetate and washed successively with 1 M sodium hydroxide, brine, dried over anhydrous sodium sulfate, filtered and concentrated under reduced pressure. The residue was purified by silica gel chromatography, eluting with dichloromethane-methanol (98:2-80:20) to give 0.0191 g of 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-N-(tetrahydropyran-4-yl)benzamide (I-63)

EXAMPLE 66

4-(9-Cyclopentyl-5,7,7-trimethyl-6-oxo-6,7,8,9-tetrahydro-5H-pyrimido[4,5-b][1,4]diazepin-2-ylamino)-N-(1-methyl-piperidin-4-yl)-benzenesulfonamide (I-64)

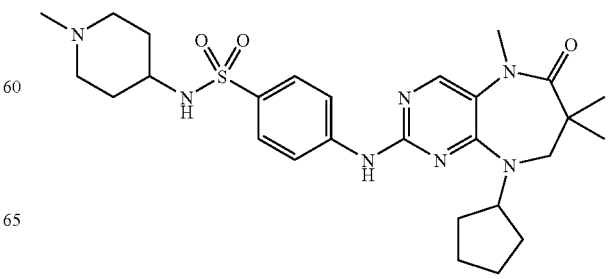

Step a

To a solution of 0.570 g (0.00477 mole) of 4-amino-1-methylpiperidine, 1.5 mL of ethyldiisopropylamine and 20 mL of dichloromethane at 0 degrees, was added 1.000 g (0.00451 mole) of 4-nitrobenzenesulfonyl chloride. The mixture was stirred for 1 hour and then diluted with 100 mL of ethyl acetate and washed successively twice with 20 mL of saturated sodium bicarbonate solution, twice with 20 mL of brine, dried over anhydrous sodium sulfate, filtered and concentrated under reduced pressure to give 1.23 g of N-(1-methyl-piperidin-4-yl)-4-nitro-benzenesulfonamide as a yellow solid. The material was used without further purification.

Step b

A mixture of 1.22 g of N-(1-methyl-piperidin-4-yl)-4-nitro-benzenesulfonamide, 0.614 g of 10% palladium on carbon catalyst and 140 mL of tetrahydrofuran was shaken under a 40 psi atmosphere of hydrogen on a Paar hydrogenator for 18 hrs. The resulting mixture was filtered through Celite, washing the filter pad with ethyl acetate. The combined filtrate was concentrated under reduced pressure to give 1.00 g of N-(1-methyl-piperidin-4-yl)-4-nitro-benzenesulfonamide as a white solid.

Step c

A mixture of 0.0203 g (0.000066 mole) of 2-chloro-9-cyclopentyl-5,7,7-trimethyl-5,7,8,9-tetrahydro-pyrimido[4,5-b][1,4]diazepin-6-one (VII-38), 0.0207 g (0.000077 mole) of N-(1-methyl-piperidin-4-yl)-4-nitro-benzenesulfonamide, 0.6 mL of ethanol, 2.4 mL of water and 2 drops of hydrochloric acid was heated at reflux for 17 hrs. The mixture was taken up in 50 mL of ethyl acetate and washed successively twice with 7 mL of 1M sodium hydroxide, twice with 7 mL of water and 7 mL of brine. The organic layer was concentrated under reduced pressure and the residue purified by silica gel chromatography, elution with dichloromethane-methanol 95:5-80:20) gave 0.0151 g of 4-(9-cyclopentyl-5,7,7-trimethyl-6-oxo-6,7,8,9-tetrahydro-5H-pyrimido[4,5-b][1,4]diazepin-2-ylamino)-N-(1-methyl-piperidin-4-yl)-benzenesulfonamide (I-64) as an off-white solid.

EXAMPLE 67

(rac)-4-(9-Allyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-65)

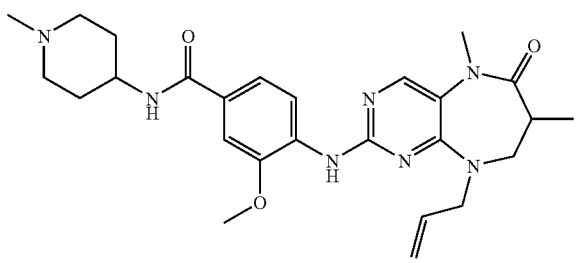

Step a

To a mixture of 1.71 g (0.010 mole) of (rac)-2-methyl-3-(2-propenylamino)-propanoic acid methyl ester, 1.94 g (0.010 mole) of 2,4-dichloro-5-nitro-pyrimidine, 50 mL of ethyl acetate and 25 mL of water was added 3.0 g (0.030 mole) of potassium bicarbonate. The mixture was stirred for 3 hours, and then diluted with 50 mL of ethyl acetate and 50 mL of water. The aqueous layer was extracted with 100 mL of ethyl acetate. The organic layers were washed with 100 mL of brine, combined, dried over anhydrous magnesium sulfate, filtered and concentrated under reduced pressure. The residue was purified by silica gel chromatography, eluting with dichloromethane-ethyl acetate (100:0-97.5:2.5) to give 2.55 g of (rac)-3-[allyl-(2-chloro-5-nitro-pyrimidin-4-yl)-amino]-2-methyl-propanoic acid methyl ester (IV-65) as a pale yellow oil.

Step b

Iron Powder (2.55 g, 45.7 mmol) (MCB) was Added

To a solution of 2.55 g (0.002 mole) of (rac)-3-[allyl-(2-chloro-5-nitro-pyrimidin-4-yl)-amino]-2-methyl-propanoic acid methyl ester (IV-65) and 20 mL of acetic acid, was added 2.55 g (0.0457 g-atom) of iron powder. The mixture was heated at 80 degrees for 2 hours and then filtered through Celite while still hot. The filter cake was washed with 100 mL of ethyl acetate. The filtrate was washed successively with 100 mL of water, 100 mL of 7.4 M ammonium hydroxide, 100 mL of water and 100 mL of brine. The aqueous layers were back extracted with 100 mL of ethyl acetate. The ethyl acetate layers were combined, dried over anhydrous magnesium sulfate, filtered and concentrated under reduced pressure. The residue was recrystallized from dichloromethane—hexanes to give 1.40 g of (rac)-9-allyl-2-chloro-7-methyl-5,7,8,9-tetrahydro-pyrimido[4,5-b][1,4]diazepin-6-one (VI-65) as off-white crystalline solid.

Step c

To a mixture of 1.37 g (0.00542 mole) of (rac)-9-allyl-2-chloro-7-methyl-5,7,8,9-tetrahydro-pyrimido[4,5-b][1,4]diazepin-6-one (VI-65), 0.51 mL (0.00813 mole) of iodomethane and 15 mL of N,N-dimethyl-formamide at 0 degrees, was added 0.33 g (0.00813 mole) of 60% oil dispersion of sodium hydride. The mixture was stirred at 0 degrees for 2 hours and then partitioned between ethyl acetate and water. The aqueous phase was extracted with ethyl acetate. The combined organic phases were washed successively with water and brine, dried over anhydrous magnesium sulfate, filtered and concentrated under reduced pressure. The residue was purified by silica gel chromatography, eluting with hexanes-ethyl acetate (100:0-60:40) to give 1.45 g of (rac)-9-allyl-2-chloro-5,7-dimethyl-5,7,8,9-tetrahydro-pyrimido[4,5-b][1,4]diazepin-6-one (VII-65). HRMS (ES+) m/z Calcd for C12H15ClN4O+H [(M+H)$^+$]: 267.1007. Found: 267.1007.

Step d

A solution of 0.050 g (0.00019 mole) of (rac)-9-allyl-2-chloro-5,7-dimethyl-5,7,8,9-tetrahydro-pyrimido[4,5-b][1,4]diazepin-6-one (VII-65), 0.049 g (0.00019 mole) of 4-amino-3-methoxy-N-(1-methyl-piperidin-4-yl)-benzamide, 0.047 g (0.00025 mole) of p-toluene-sulfonic acid monohydrate and 4.0 mL of 2-propanol was heated at 180 degrees for 2 hours in a microwave reactor. The reaction mixture was concentrated under reduced pressure. The residue was diluted with dichloromethane and washed twice with saturated sodium bicarbonate solution. The aqueous phases were extracted with dichloromethane. The combined organic phases were washed with brine, dried over anhydrous magnesium sulfate and concentrated under reduced pressure. The residue was purified by silica gel chromatography, eluting with dichloromethane-methanol (100:0-75:25) to give 0.047 g of (rac)-4-(9-allyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-65) as white

EXAMPLE 68

(rac)-4-[(9-Cyclohexyl-5,7-dimethyl-6-oxo-6,7,8,9-tetrahydro-5H-pyrimido[4,5-b][1,4]diazepin-2-yl)-methyl-amino]-3-methoxy-N-(1-methyl-piperidin-4-yl)-benzamide (I-66)

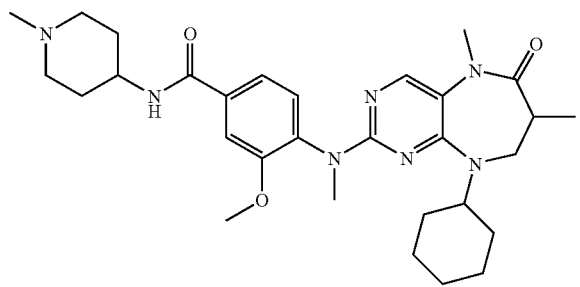

A solution of 0.10 g (0.00032 mole) of (rac)-2-chloro-9-cyclohexyl-5,7-dimethyl-5,7,8,9-tetrahydro-pyrimido[4,5-b][1,4]diazepin-6-one (VII-19), 0.060 g (0.00032 mole) of 4-amino-3-methoxy-benzoic acid methyl ester, 0.10 g (0.00049 mole) of p-toluene-sulfonic acid monohydrate and 4 mL of 2-propanol at 150 degrees for 1 hour in a microwave reactor. The reaction mixture was concentrated under reduced pressure. The residue was diluted with dichloromethane and washed twice with saturated sodium bicarbonate solution. The aqueous phase was extracted with dichloromethane and the combined organic phases were washed with brine, dried over anhydrous magnesium sulfate, filtered and concentrated under reduced pressure. The residue was purified by silica gel chromatography, eluting with dichloromethane-methanol (100:0-85:15%), to give 0.14 g of (rac)-4-(9-cyclohexyl-5,7-dimethyl-6-oxo-6,7,8,9-tetrahydro-5H-pyrimido[4,5-b][1,4]diazepin-2-ylamino)-3-methoxy-benzoic acid methyl ester as white powder.

To a mixture of 0.170 g (0.00037 mole) of (rac)-4-(9-cyclohexyl-5,7-dimethyl-6-oxo-6,7,8,9-tetrahydro-5H-pyrimido[4,5-b][1,4]diazepin-2-yl amino)-3-methoxy-benzoic acid methyl ester, 0.35 mL (0.00056 mole) of iodomethane and 10 mL of N,N-dimethylformamide at 0 degrees, was added 0.024 g of sodium hydride (60% dispersion in mineral oil). The mixture was stirred at 0 degrees for 2 hours and then partitioned between ethyl acetate and water. The aqueous phase was extracted with ethyl acetate, and the combined organic phases were washed successively with water and brine, dried over anhydrous magnesium sulfate, filtered and concentrated under reduced pressure. The residue was purified by silica chromatography, eluting with hexanes-ethyl acetate (30:70) to give 0.170 g of (rac)-4-[(9-cyclohexyl-5,7-dimethyl-6-oxo-6,7,8,9-tetrahydro-5H-pyrimido[4,5-b][1,4]diazepin-2-yl)-methyl-amino]-3-methoxy-benzoic acid methyl ester as white powder.

An aqueous solution of sodium hydroxide (2N, 1.0 mL, 2 mmol) was added A mixture of 0.170 g (0.00036 mole) of (rac)-4-[(9-cyclohexyl-5,7-dimethyl-6-oxo-6,7,8,9-tetrahydro-5H-pyrimido[4,5-b][1,4]diazepin-2-yl)-methyl-amino]-3-methoxy-benzoic acid methyl ester, 6 mL of tetrahydrofuran, 2 mL of methanol and 1 mL of 2M sodium hydroxide was heated at 75 degrees for 4 hours. The mixture was concentrated under reduced pressure and then azeotroped with toluene and concentrated under reduced pressure, The solid residue was triturated with ethyl acetate. The solid was then suspended in water and treated with 1M hydrochloric acid to pH=4. After stirring 30 minutes, the solid was collected, washed with water and dried to give 0.080 g of (rac)-4-[(9-cyclohexyl-5,7-dimethyl-6-oxo-6,7,8,9-tetrahydro-5H-pyrimido[4,5-b][1,4]diazepin-2-yl)-methyl-amino]-3-methoxy-benzoic acid as white powder.

To a mixture of 0.058 g (0.00013 mole) of (rac)-4-[(9-cyclohexyl-5,7-dimethyl-6-oxo-6,7,8,9-tetrahydro-5H-pyrimido[4,5-b][1,4]diazepin-2-yl)-methyl-amino]-3-methoxy-benzoic acid, 0.054 g (0.00014 mole) of 1-[bis(dimethylamino)-methylene]-1H-1,2,3-triazolo[4,5-b]pyridinium-3-oxide hexafluorophosphate and 3 mL of N,N-dimethylformamide was added 0.030 mL (0.00019 mole) of ethyldiisopropylamine. The mixture was stirred at room temperature for 30 minutes and then 0.022 g (0.00019 mole) of 4-amino-1-methyl-piperidine was then added. The mixture was stirred at room temperature for 3 hours and was then partitioned between ethyl acetate and water. The aqueous phase was extracted twice with ethyl acetate. The combined organic phases were washed successively with water and brine, dried anhydrous magnesium sulfate, filtered and concentrated under reduced pressure. The residue was purified by silica gel chromatography, eluting with dichloromethane-methanol (100:0-75-25) to give 0.070 g of (rac)-4-[(9-cyclohexyl-5,7-dimethyl-6-oxo-6,7,8,9-tetrahydro-5H-pyrimido [4,5-b][1,4]diazepin-2-yl)-methyl-amino]-3-methoxy-N-(1-methyl-piperidin-4-yl)-benzamide (I-66) as white powder. HRMS (ES+) m/z Calcd for C30H43N7O3+H [(M+H)$^+$]: 550.3500. Found: 550.3504.

EXAMPLE 69

(rac)-3-Methoxy-4-(8-methyl-9-oxo-1,3,5,8-tetraaza-tricyclo[8.3.1.0*2,7*]tetradeca-2,4,6-trien-4-ylamino)-N-(1-methyl-piperidin-4-yl)-benzamide (I-67)

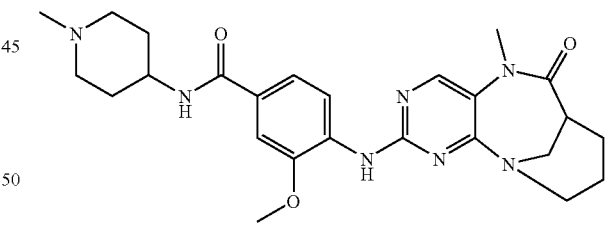

Step a

To a solution of 3.16 g (0.02 mole) of piperidine-3-carboxylic acid ethyl ester, 3.71 g (0.019 mole) of 2,4-dichloro-5-nitro-pyrimidine and 60 mL of ether at 5 degrees, was added a solution of 4 g (0.04 mole) of potassium bicarbonate in 40 mL of water was added over 25 minutes. The mixture was stirred for an additional 1 hour, then extracted with ethyl acetate, dried over anhydrous magnesium sulfate, filtered and concentrated under reduced pressure. The residue was purified by silica gel chromatography, eluting with hexanes-ethyl acetate (100:0-88:12) to give 3.99 g of (rac)-1-(2-chloro-5-nitro-pyrimidin-4-yl)-piperidine-3-carboxylic acid ethyl ester (IV-67).

87

Step b

To an ice cooled mixture of 1 g (0.0032 mole) of (rac)-1-(2-chloro-5-nitro-pyrimidin-4-yl)-piperidine-3-carboxylic acid ethyl ester (IV-67), 1.96 mL of trifluoracetic acid and 15 mL of ethyl acetate, was added 2.76 g (0.02 mole) of stannous chloride dihydrate. The mixture was stirred overnight at ambient temperature. The mixture was made basic (pH 14) by the addition of 15% sodium hydroxide solution. The mixture was extracted with ethyl acetate, dried over anhydrous magnesium sulfate, filtered and concentrated under reduced pressure to give 0.086 g of (rac)-1-(5-amino-2-chloro-pyrimidin-4-yl)-piperidine-3-carboxylic acid ethyl ester (V-67).

Step c

A solution of 0.114 g (0.0004 mole) of (rac)-1-(5-amino-2-chloro-pyrimidin-4-yl)-piperidine-3-carboxylic acid ethyl ester (V-67), 1 mL of tetrahydrofuran and 1 mL of 1M sodium hydroxide was stirred at ambient temperature for 3 hours. The mixture was acidified to pH=3 by the addition of 1M hydrochloric acid. The mixture was extracted with ethyl acetate, dried over anhydrous magnesium sulfate, filtered and concentrated under reduced pressure to give 0.0812 g of (rac)-1-(5-amino-2-chloro-pyrimidin-4-yl)-piperidine-3-carboxylic acid. This intermediate was stirred with 0.13 g (0.00034 mole) of 1-[bis(dimethylamino)methylene]-1H-1,2,3-triazolo[4,5-b]pyridinium-3-oxide hexafluorophosphate, 0.058 g (0.00057 mol) of triethylamine and 2 mL of dichloromethane overnight at ambient temperature. The mixture was diluted with dichloromethane, washed with water, dried over anhydrous magnesium sulfate, filtered and concentrated under reduced pressure to give 0.075 g of (rac)-4-chloro-1,3,5,8-tetraaza-tricyclo[8.3.1.0*2,7*]tetradeca-2,4,6-trien-9-one (VI-67).

Step d

A mixture of 0.075 g (0.00032 mole) of (rac)-4-chloro-1,3,5,8-tetraaza-tricyclo[8.3.1.0*2,7*]tetradeca-2,4,6-trien-9-one (VI-67), 0.8 mL of dimethylformamide, 0.17 g (0.0005 mole) of cesium carbonate and 0.055 g (0.0004 mole) of iodomethane was stirred at ambient temperature for 2 hours and then concentrated under reduced pressure. The residue was diluted with ethyl acetate, washed with water, dried over anhydrous magnesium sulfate, filtered and concentrated under reduced pressure to give (rac)-4-chloro-8-methyl-1,3,5,8-tetraaza-tricyclo[8.3.1.0*2,7*]tetradeca-2,4,6-trien-9-one (VII-67), which was used directly in the next step.

Step e

A mixture of the (rac)-4-chloro-8-methyl-1,3,5,8-tetraaza-tricyclo[8.3.1.0*2,7*]tetradeca-2,4,6-trien-9-one (VII-67), obtained in the previous step, 1 mL of isopropanol, 0.06 g of p-toluenesulfonic acid monohydrate and 0.050 g (0.00019 mole) of 4-amino-3-methoxy-N-(1-methyl-piperidin-4-yl)-benzamide at 200 degrees for 33 minutes in a microwave reactor. The residue was purified by C18 reverse phase silica gel chromatography, eluting with an acetonitrile-water gradient (10:90-100:0) to give 0.023 g of (rac)-3-methoxy-4-(8-methyl-9-oxo-1,3,5,8-tetraaza-tricyclo[8.3.1.0*2,7*]tetradeca-2,4,6-trien-4-ylamino)-N-(1-methyl-piperidin-4-yl)-benzamide (I-67).

88

EXAMPLE 70

(rac)-4-(4-Cyclopentyl-9-methyl-10-oxo-1,2,3,3a,4,9,10,10a-octahydro-4,5,7,9-tetraaza-benzo[f]azulen-6-ylamino)-3-methoxy-N-(1-methyl-piperidin-4-yl)-benzamide (I-68)

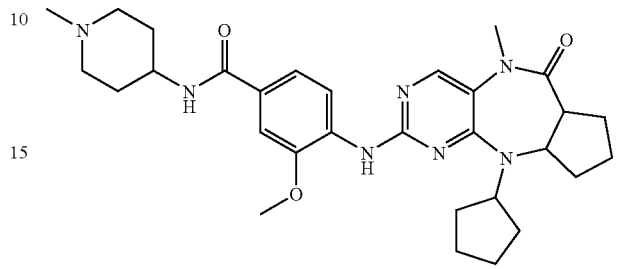

Step a

To an ice cooled solution of 9.56 g (0.045 mole) of (rac)-2-cyclopentylamino-cyclopentanecarboxylic acid, methyl ester and 200 mL of ethyl acetate was added 9.5 g (0.0475 mole) of 2,4-dichloro-5-nitro-pyrimidine and 9.6 g (0.113 mole) of sodium bicarbonate. The mixture was heated overnight at 65 degrees, then cooled and washed with water, extracting the aqueous layer twice with ethyl acetate. The combined ethyl acetate layers were washed successively with water, then brine, dried over anhydrous magnesium sulfate, filtered and concentrated under reduced pressure. The residue was purified by silica gel chromography, eluting with hexanes-ethyl acetate (100:0-80:20), to give 11.4 g of (rac)-2-[(2-chloro-5-nitro-pyrimidin-4-yl)-cyclopentyl-amino]-cyclopentanecarboxylic acid methyl ester (IV-68).

Step b

A mixture of 5.7 g (0.015 mole) of (rac)-2-[(2-chloro-5-nitro-pyrimidin-4-yl)-cyclopentyl-amino]-cyclopentanecarboxylic acid methyl ester (IV-68), ca. 0.18 g of 10% palladium on carbon catalyst and 150 mL of ethyl acetate was stirred under an atmosphere of hydrogen until hydrogen uptake stopped. The mixture was then filtered through a pad of Celite, and concentrated under reduced pressure, to give a mixture of (rac)-2-[(5-amino-2-chloro-pyrimidin-4-yl)-cyclopentyl-amino]-cyclopentanecarboxylic acid methyl ester (V-68) and (rac)-6-chloro-4-cyclopentyl-2,3,3a,4,9,10a-hexahydro-1H-4,5,7,9-tetraaza-benzo[f]azulen-10-one (VI-68). The residue was slurried in dichloromethane and the solid (0.68 g, VI-68) was collected by suction filtration. The filtrate was concentrated under reduced pressure and purified by silica gel chromatography, eluting with hexanes-ethyl acetate (100:0-60:40) to give 1.33 g of (rac)-2-[(5-amino-2-chloro-pyrimidin-4-yl)-cyclopentyl-amino]-cyclopentanecarboxylic acid methyl ester (V-68) and 2.16 g of (rac)-6-chloro-4-cyclopentyl-2,3,3a,4,9,10a-hexahydro-1H-4,5,7,9-tetraaza-benzo[f]azulen-10-one (VI-68).

Step c

A mixture of 150 mL of ethanol, 3.0 mL of acetic acid and 2.85 g (0.0084 mole) of (rac)-2-[(5-amino-2-chloro-pyrimidin-4-yl)-cyclopentyl-amino]-cyclopentanecarboxylic acid methyl ester (V-68) from the previous step, combined with material from a separate experiment was heated at reflux overnight and then concentrated under reduced pressure to give 2.49 g of (rac)-6-chloro-4-cyclopentyl-2,3,3a,4,9,10a- hexahydro-1H-4,5,7,9-tetraaza-benzo[f]azulen-10-one (VI-68), which was used without further purification.

Step d

To a mixture of 0.68 g (0.0022 mole) of (rac)-6-chloro-4-cyclopentyl-2,3,3a,4,9,10a-hexahydro-1H-4,5,7,9-tetraaza-benzo[f]azulen-10-one (VI-68), 20 mL of dimethylformamide and 1.83 g (0.0056 mole) of cesium carbonate was added 1.254 g (0.0088 mole) of iodomethane. The mixture was stirred for 20 minutes, then diluted with ethyl acetate and water. The water layer was extracted twice with ethyl acetate and the combined ethyl acetate layers washed successively with water, then brine, dried over anhydrous magnesium sulfate, filtered and concentrated under reduced pressure to give 0.580 g of (rac)-6-chloro-4-cyclopentyl-9-methyl-2,3,3a,4,9,10a-hexahydro-1H-4,5,7,9-tetraazabenzo[f]azulen-10-one (VII-68), which was used in the next step without further purification.

Step e

A mixture of 0.580 g (0.0018 mole) of (rac)-6-chloro-4-cyclopentyl-9-methyl-2,3,3a,4,9,10a-hexahydro-1H-4,5,7,9-tetraazabenzo[f]azulen-10-one (VII-68), 0.372 g (0.0022 mole) of 4-amino-3-methoxybenzoic acid, 36.97 mL of ethanol and 0.468 mL of hydrochloric acid was heated at reflux overnight. Additional ethanol and hydrochloric acid were added and the mixture heated at reflux overnight. The mixture was then cooled, made basic to dissolve solids by the addition of sodium hydroxide solution, transferred to a separatory funnel with ethyl acetate. The aqueous layer was washed twice with ethyl acetate, and then acidified by the addition of 1 M hydrochloric acid. The acidified aqueous layer was extracted twice with ethyl acetate and these extracts were combined, washed successively with water and then brine, dried over anhydrous magnesium sulfate, filtered and concentrated under reduced pressure to give 0.277 g of (rac)-4-(4-cyclopentyl-9-methyl-10-oxo-1,2,3,3a,4,9,10,10a-octahydro-4,5,7,9-tetraaza-benzo[f]azulen-6-ylamino)-3-methoxybenzoic acid, which was used in the next step without further purification.

Step f

To a mixture of 0.277 g (0.00061 mole) of (rac)-4-(4-cyclopentyl-9-methyl-10-oxo-1,2,3,3a,4,9,10,10a-octahydro-4,5,7,9-tetraaza-benzo[f]azulen-6-ylamino)-3-methoxybenzoic acid, 0.129 g (0.00092 mole) of 1-hydroxy-1H-benzotriazole, 0.505 g (0.00092 mole) of benzotriazol-1-yloxytris(dimethylamino)phosphonium hexafluorophosphate, 0.404 g (0.00306 mole) of ethyldiisopropylamine and 40 mL of dimethylformamide was added 0.150 g (0.00092 mole) of 4-amino-1-methyl piperidine. The mixture was stirred overnight at room temperature, then diluted with water and extracted twice with ethyl acetate. The combined ethyl acetate extracts were washed successively with water and then brine, dried over anhydrous magnesium sulfate, filtered and concentrated under reduced pressure. The residue was purified by silica gel chromatography (Waters X-terra column), eluting with a gradient of acetonitrile −0.004 M aqueous ammonium acetate to give 0.070 g of (rac)-4-(4-cyclopentyl-9-methyl-10-oxo-1,2,3,3a,4,9,10,10a-octahydro-4,5,7,9-tetraaza-benzo[f]azulen-6-ylamino)-3-methoxy-N-(1-methyl-piperidin-4-yl)-benzamide (I-68) as a white solid.

EXAMPLE 71

(rac)-3-(9-Cyclopentyl-5,7-dimethyl-6-oxo-6,7,8,9-tetrahydro-5H-pyrimido[4,5-b][1,4]diazepin-2-ylamino)-N-(1-methyl-piperidin-4-yl)-benzamide
(I-69)

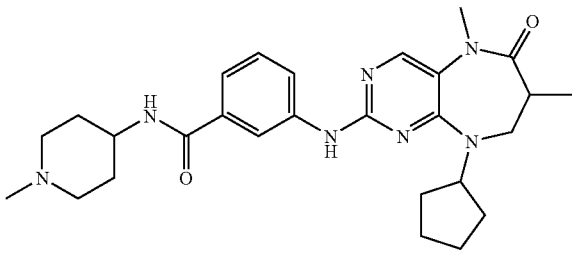

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 72

(rac)-3-(9-Cyclopentyl-5,7-dimethyl-6-oxo-6,7,8,9-tetrahydro-5H-pyrimido[4,5-b][1,4]diazepin-2-ylamino)-N-(3-dimethylamino-propyl)-benzamide
(I-70)

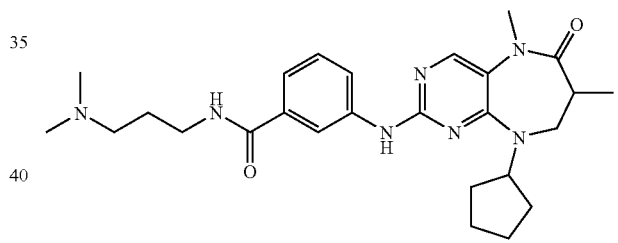

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 73

(rac)-3-(9-Cyclopentyl-5,7-dimethyl-6-oxo-6,7,8,9-tetrahydro-5H-pyrimido[4,5-b][1,4]diazepin-2-ylamino)-N-(tetrahydro-pyran-4-yl)-benzamide
(I-71)

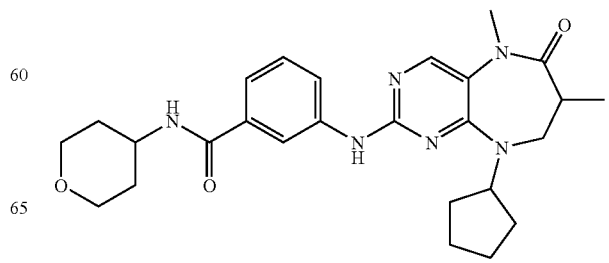

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 74

(rac)-3-(9-Cyclopentyl-5,7-dimethyl-6-oxo-6,7,8,9-tetrahydro-5H-pyrimido[4,5-b][1,4]diazepin-2-ylamino)-N-pyridin-3-yl-benzamide (I-72)

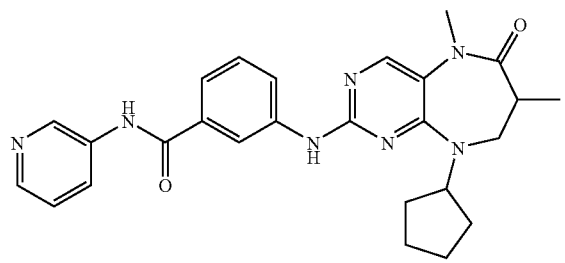

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 75

(rac)-3-(9-Cyclopentyl-5,7-dimethyl-6-oxo-6,7,8,9-tetrahydro-5H-pyrimido[4,5-b][1,4]diazepin-2-ylamino)-N-(3-dimethylamino-propyl)-4-methoxy-benzamide (I-73)

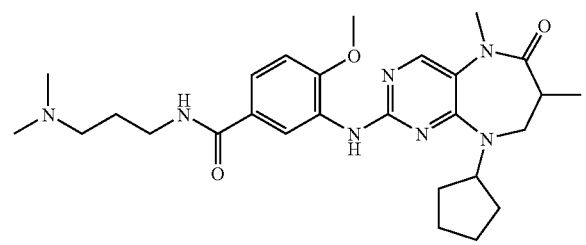

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 76

(rac)-3-(9-Cyclopentyl-5,7-dimethyl-6-oxo-6,7,8,9-tetrahydro-5H-pyrimido[4,5-b][1,4]diazepin-2-ylamino)-4-methoxy-N-(tetrahydro-pyran-4-yl)-benzamide (I-74)

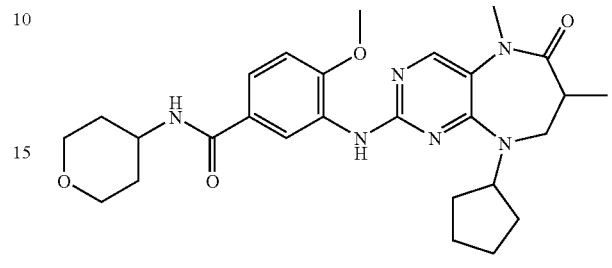

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 77

(rac)-2-(4-Benzyloxy-phenylamino)-9-cyclopentyl-5,7-dimethyl-5,7,8,9-tetrahydro-pyrimido[4,5-b][1,4]diazepin-6-one (I-75)

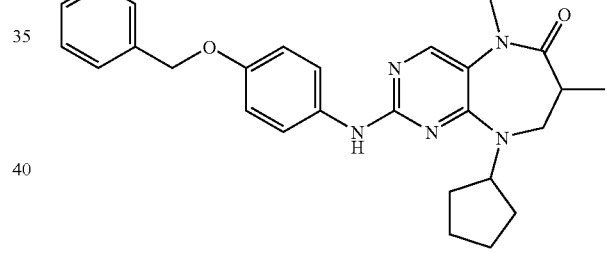

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 78

(rac)-9-Cyclopentyl-5,7-dimethyl-2-(2-pyridin-4-yl-benzooxazol-5-ylamino)-5,7,8,9-tetrahydro-pyrimido[4,5-b][1,4]diazepin-6-one (I-76)

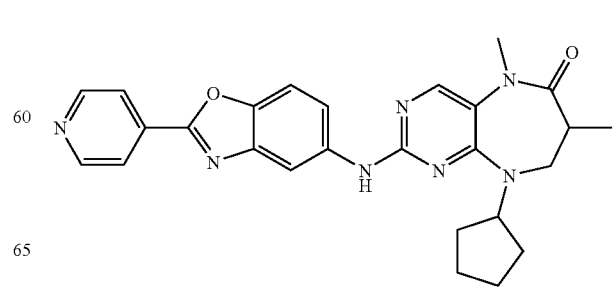

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 79

(rac)-9-Cyclopentyl-5,7-dimethyl-2-(2-pyridin-3-yl-benzooxazol-5-ylamino)-5,7,8,9-tetrahydro-pyrimido[4,5-b][1,4]diazepin-6-one (I-77)

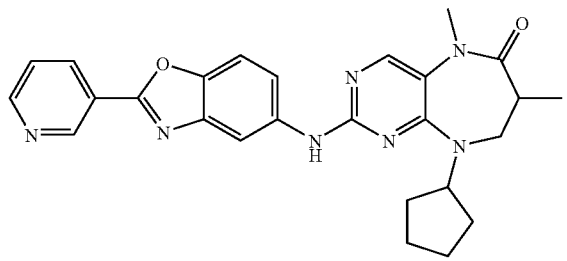

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 80

(rac)-N-[3-(9-Cyclopentyl-5,7-dimethyl-6-oxo-6,7,8,9-tetrahydro-5H-pyrimido[4,5-b][1,4]diazepin-2-ylamino)-4-methoxy-phenyl]-benzamide (I-78)

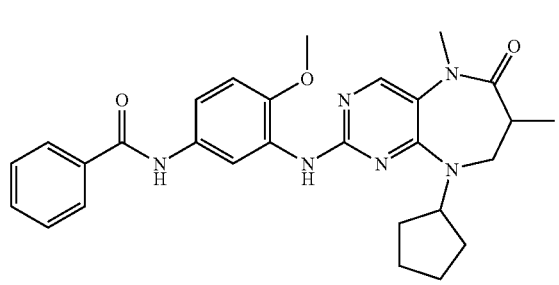

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 81

(rac)-4-(9-Cyclopentyl-5,7-dimethyl-6-oxo-6,7,8,9-tetrahydro-5H-pyrimido[4,5-b][1,4]diazepin-2-ylamino)-3-methoxy-benzoic acid hydrazide (I-79)

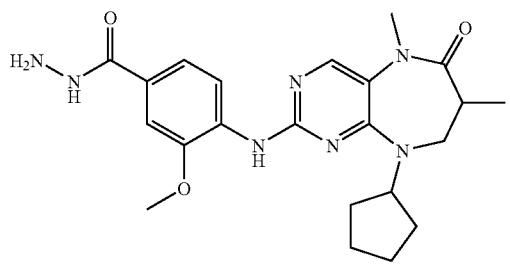

To a mixture of 0.45 g (0.00106 mole) of (rac)-4-(9-cyclopentyl-5,7-dimethyl-5,7,8,9-tetrahydro-pyrimido[4,5-b][1,4]diazepin-2-yl amino-3-methoxy-benzoic acid (I-1), 0.47 g (0.00124 mole) of 1-[bis(dimethylamino)methylene]-1H-1,2,3-triazolo[4,5-b]pyridinium 3-oxide hexafluorophosphate and 8 mL of N,N-dimethylformamide was added 0.29 mL (0.00166 mole) of ethyldiisopropylamine. The mixture was stirred at room temperature for 30 minutes, then 0.10 mL (0.0032 mole) of anhydrous hydrazine was added. The mixture was stirred at room temperature for 3 hours and then partitioned between ethyl acetate and water. The aqueous phase was extracted twice with ethyl acetate. The combined organic phase were washed successively with water and brine, dried over anhydrous magnesium sulfate, filtered and concentrated under reduced pressure. The residue was purified by silica gel chromatography, eluting with dichloromethane-methanol (95:5) to give 0.50 g of (rac)-4-(9-cyclopentyl-5,7-dimethyl-6-oxo-6,7,8,9-tetrahydro-5H-pyrimido[4,5-b][1,4]diazepin-2-ylamino)-3-methoxy-benzoic acid hydrazide (I-79) as white solid. HRMS (ES+) m/z Calcd for C22H29N7O3+H [(M+H)+]: 440.2405. Found: 440.2405.

EXAMPLE 82

(rac)-1-Acetyl-piperidine-4-carboxylic acid [3-(9-cyclopentyl-5,7-dimethyl-6-oxo-6,7,8,9-tetrahydro-5H-pyrimido[4,5-b][1,4]diazepin-2-ylamino)-4-methoxy-phenyl]-amide (I-80)

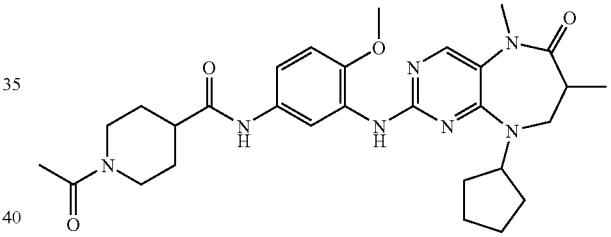

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 83

(rac)-2-Chloro-4-(9-cyclopentyl-5,7-dimethyl-6-oxo-6,7,8,9-tetrahydro-5H-pyrimido[4,5-b][1,4]diazepin-2-ylamino)-N-(1-ethyl-piperidin-4-yl)-benzamide (I-81)

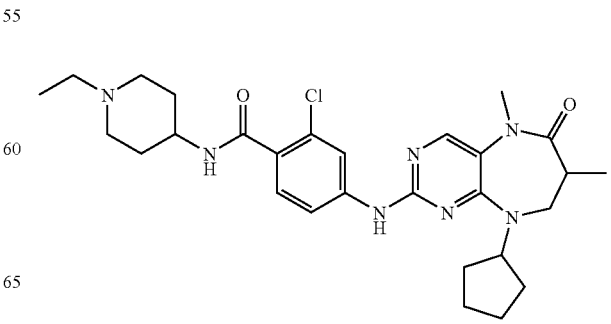

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 84

(rac)-2-Chloro-4-(9-cyclopentyl-5,7-dimethyl-6-oxo-6,7,8,9-tetrahydro-5H-pyrimido[4,5-b][1,4]diazepin-2-ylamino)-N-pyridin-3-yl-benzamide (I-82)

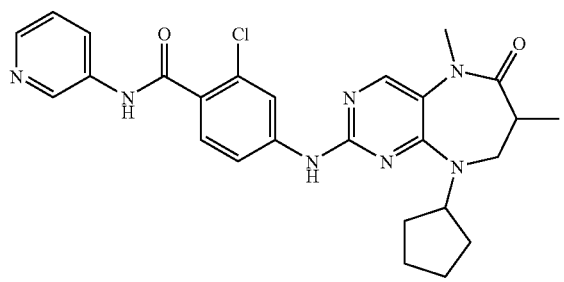

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 85

(rac)-2-Chloro-4-(9-cyclopentyl-5,7-dimethyl-6-oxo-6,7,8,9-tetrahydro-5H-pyrimido[4,5-b][1,4]diazepin-2-ylamino)-N-(3-dimethylamino-propyl)-benzamide (I-83)

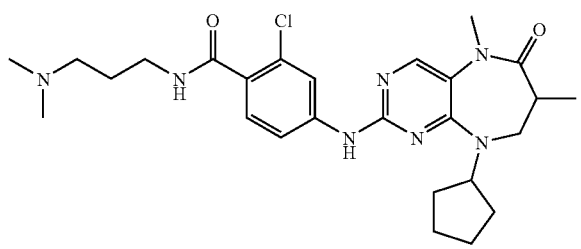

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 86

(rac)-2-Chloro-4-(9-cyclopentyl-5,7-dimethyl-6-oxo-6,7,8,9-tetrahydro-5H-pyrimido[4,5-b][1,4]diazepin-2-ylamino)-N-(1-methyl-piperidin-4-yl)-benzamide (I-84)

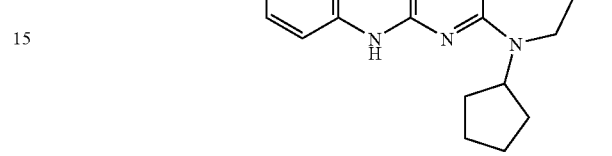

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 87

(rac)-2-Chloro-N-cyclohexyl-4-(9-cyclopentyl-5,7-dimethyl-6-oxo-6,7,8,9-tetrahydro-5H-pyrimido[4,5-b][1,4]diazepin-2-ylamino)-benzamide (I-85)

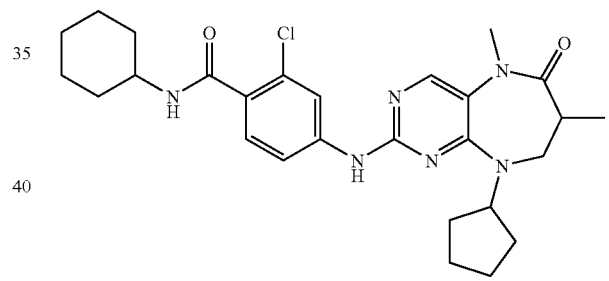

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 88

(rac)-2-Chloro-4-(9-cyclopentyl-5,7-dimethyl-6-oxo-6,7,8,9-tetrahydro-5H-pyrimido[4,5-b][1,4]diazepin-2-ylamino)-N-pyridin-4-yl-benzamide (I-86)

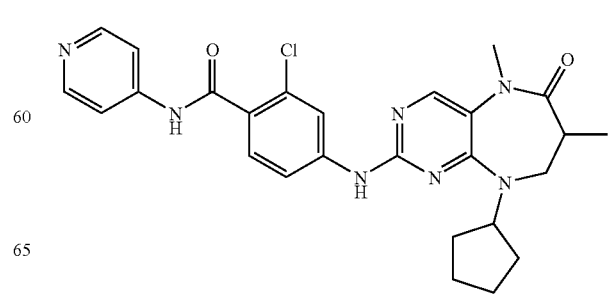

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 89

(rac)-2-Chloro-4-(9-cyclopentyl-5,7-dimethyl-6-oxo-6,7,8,9-tetrahydro-5H-pyrimido[4,5-b][1,4]diazepin-2-ylamino)-N-(2-dimethylamino-ethyl)-benzamide (I-87)

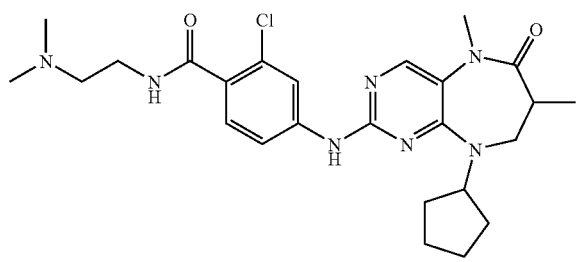

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 90

(rac)-2-Chloro-4-(9-cyclopentyl-5,7-dimethyl-6-oxo-6,7,8,9-tetrahydro-5H-pyrimido[4,5-b][1,4]diazepin-2-ylamino)-N-(tetrahydro-pyran-4-yl)-benzamide (I-88)

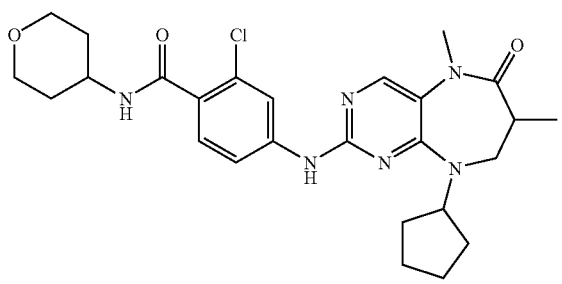

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 91

(rac)-3-(9-Cyclopentyl-5,7-dimethyl-6-oxo-6,7,8,9-tetrahydro-5H-pyrimido[4,5-b][1,4]diazepin-2-ylamino)-N-(1-ethyl-piperidin-4-yl)-benzamide (I-89)

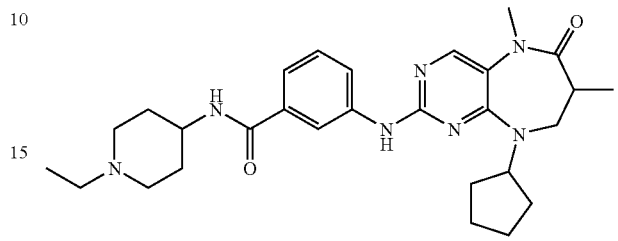

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 92

(rac)-3-(9-Cyclopentyl-5,7-dimethyl-6-oxo-6,7,8,9-tetrahydro-5H-pyrimido[4,5-b][1,4]diazepin-2-ylamino)-N-(3-methoxy-propyl)-benzamide (I-90)

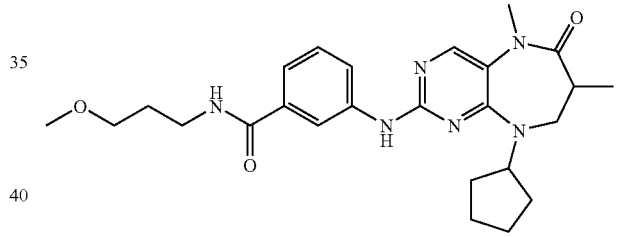

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 93

(rac)-N-Cyclohexyl-3-(9-cyclopentyl-5,7-dimethyl-6-oxo-6,7,8,9-tetrahydro-5H-pyrimido[4,5-b][1,4]diazepin-2-ylamino)-benzamide (I-91)

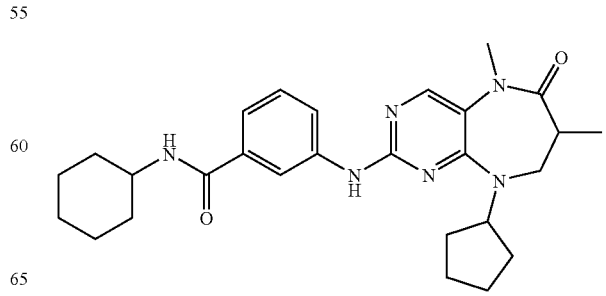

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 94

(rac)-3-(9-Cyclopentyl-5,7-dimethyl-6-oxo-6,7,8,9-tetrahydro-5H-pyrimido[4,5-b][1,4]diazepin-2-ylamino)-N-pyridin-4-yl-benzamide (I-92)

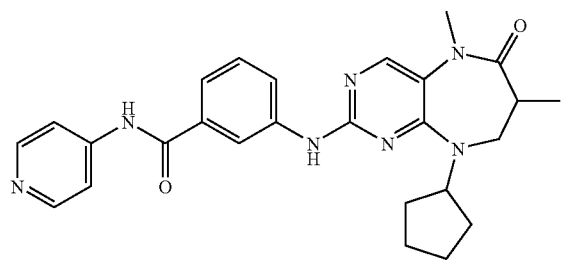

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 95

(rac)-3-(9-Cyclopentyl-5,7-dimethyl-6-oxo-6,7,8,9-tetrahydro-5H-pyrimido[4,5-b][1,4]diazepin-2-ylamino)-N-(2-dimethylamino-ethyl)-benzamide (I-93)

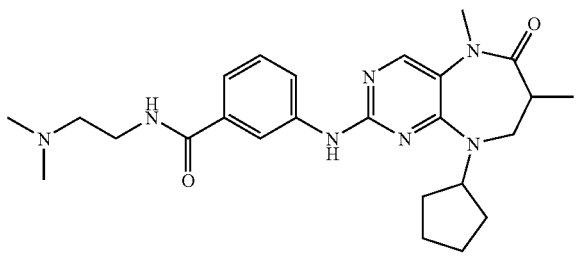

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 96

(rac)-4-(9-Cyclopentyl-5,7-dimethyl-6-oxo-6,7,8,9-tetrahydro-5H-pyrimido[4,5-b][1,4]diazepin-2-ylamino)-N-(1-ethyl-piperidin-4-yl)-benzamide (I-94)

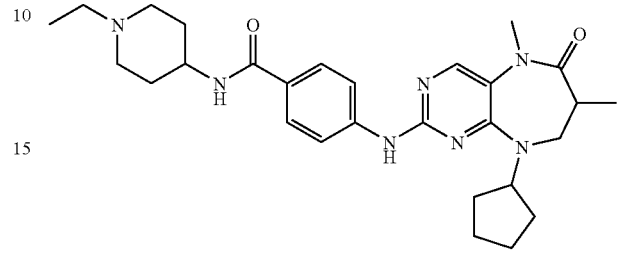

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 97

(rac)-4-(9-Cyclopentyl-5,7-dimethyl-6-oxo-6,7,8,9-tetrahydro-5H-pyrimido[4,5-b][1,4]diazepin-2-ylamino)-N-(3-dimethylamino-propyl)-benzamide (I-95)

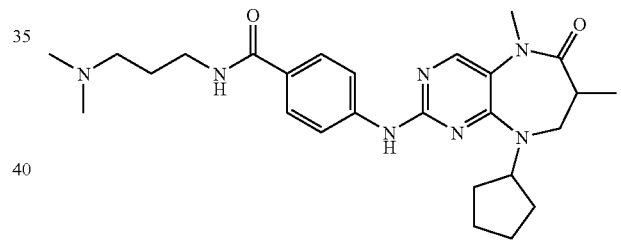

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 98

(rac)-4-(9-Cyclopentyl-5,7-dimethyl-6-oxo-6,7,8,9-tetrahydro-5H-pyrimido[4,5-b][1,4]diazepin-2-ylamino)-N-(3-methoxy-propyl)-benzamide (I-96)

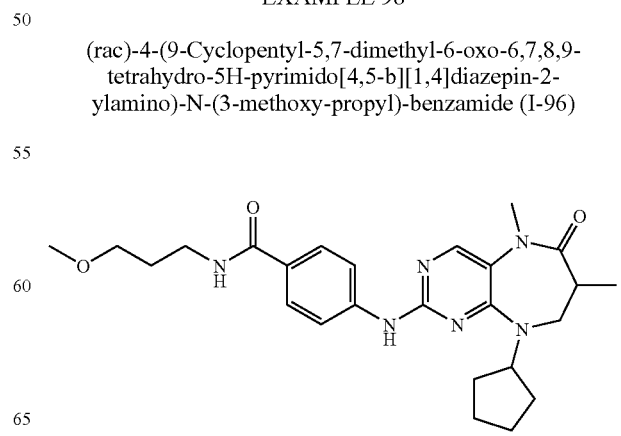

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 99

(rac)-4-(9-Cyclopentyl-5,7-dimethyl-6-oxo-6,7,8,9-tetrahydro-5H-pyrimido[4,5-b][1,4]diazepin-2-ylamino)-N-(1-ethyl-piperidin-4-yl)-3-methyl-benzamide (I-97)

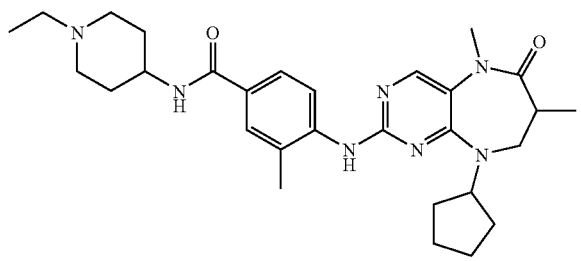

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 100

(rac)-4-(9-Cyclopentyl-5,7-dimethyl-6-oxo-6,7,8,9-tetrahydro-5H-pyrimido[4,5-b][1,4]diazepin-2-ylamino)-N-(3-dimethylamino-propyl)-3-methyl-benzamide (I-98)

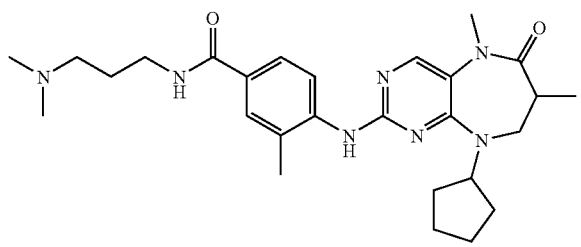

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 101

(rac)-4-(9-Cyclopentyl-5,7-dimethyl-6-oxo-6,7,8,9-tetrahydro-5H-pyrimido[4,5-b][1,4]diazepin-2-ylamino)-N-(3-methoxy-propyl)-3-methyl-benzamide (I-99)

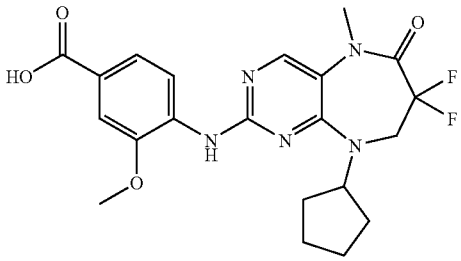

Prepared from (rac)-2-chloro-9-cyclopentyl-5,7-dimethyl-5,7,8,9-tetrahydro-pyrimido[4,5-b][1,4]diazepin-6-one (VII-1) in a manner similar to the method described in example 3.

EXAMPLE 102

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-100)

Step a

A solution of 3.6 g (0.016 mole) of 3-cyclopentylamino-2,2-difluoro-propanoic acid ethyl ester in 3 mL of ethyl acetate was added over 5 minutes to a cooled (0 degrees) mixture of 3.2 g (0.016 mole) of 2,4-dichloro-5-nitro-pyrimidine, 5.47 g (0.064 mole) of sodium bicarbonate and 36 mL of ethyl acetate. The cooling bath was removed and the mixture stirred for 17 hours at room temperature. Activated charcoal was added and after stirring briefly, the mixture was filtered through a pad of Celite, washing the filter pad with ethyl acetate. The filtrate was concentrated under reduced pressure to give 6.29 g of 3-[(2-chloro-5-nitro-pyrimidin-4-yl)-cyclopentyl-amino]-2,2-difluoro-propanoic acid ethyl ester (IV-100) as a yellow thick oil, which contained a small portion of a regioisomer. This material was used directly in the next step without further purification.

Step b

To a solution of 6.16 g (0.016 mole) of 3-[(2-chloro-5-nitro-pyrimidin-4-yl)-cyclopentyl-amino]-2,2-difluoro-propanoic acid methyl ester (IV-100) in 120 mL of acetic acid was added 6.0 g (0.11 g-atom) of iron powder. The mixture was heated to 80 degrees for 2 hours and then filtered while hot. Water and ethyl acetate were added to the filtrate and the mixture was stirred for 10 minutes and then filtered. The layers were separated. The organic layer was washed successively with ammonium hydroxide and water, dried over anhydrous magnesium sulfate, filtered and concentrated under reduced pressure. Recrystallization of the residue with ethyl acetate and hexane gave 2.94 g of 2-chloro-9-cyclopentyl-7,7-difluoro-5,7,8,9-tetrahydro-pyrimido[4,5-b][1,4]diazepin-6-one (VI-100).

Step c

To a solution of 1.4 g (0.0046 mole) of 2-chloro-9-cyclopentyl-7,7-difluoro-5,7,8,9-tetrahydro-pyrimido[4,5-b][1,4]diazepin-6-one (VI-100) in 30 mL of dimethylformamide was added 2.27 g (0.0069 mole) of cesium carbonate, followed by 0.87 mL (0.014 mole) of iodomethane. After stirring four hours, the mixture filtered and then concentrated under reduced pressure. Ice water was added to the residue to give a precipitate. The solid was collected by filtration, washed with water and dried under vacuum to give 1.37 g of 2-chloro-9-cyclopentyl-7,7-difluoro-5-methyl-5,7,8,9-tetrahydro-pyrimido[4,5-b][1,4]diazepin-6-one (VII-100) as a white solid.

Step d

A mixture of 1.0 g (0.0032 mole) of 2-chloro-9-cyclopentyl-7,7-difluoro-5-methyl-5,7,8,9-tetrahydro-pyrimido[4,5-b][1,4]diazepin-6-one (VII-100) and 0.63 g (0.0038 mole) of 4-amino-3-methoxy-benzoic acid in 76 mL of ethanol-water-hydrochloric acid (20:80:1) was heated at reflux for 18 hours, then cooled and partially concentrated under reduced pressure. The resulting solid was collected by filtration, washed with water and dried to give 0.92 g of crude 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-100) which was used without further purification in subsequent steps.

EXAMPLE 103

4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-101)

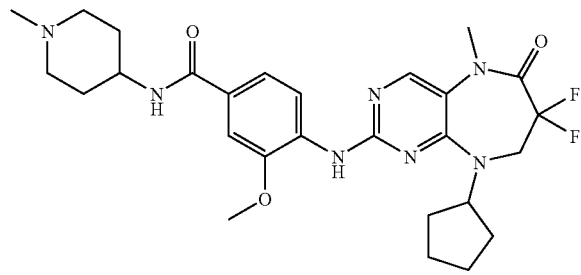

To a mixture of 0.10 g (0.00022 mole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-100), 0.16 mL (0.00090 mole) of ethyldiisopropyl amine and 0.028 g (0.00025 mole) of 4-amino-1-methylpiperidine in 3.0 mL of dimethylformamide was added 0.11 g (0.00025 mole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (100:0-90:10) gave 0.057 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide as a white solid (I-101).

EXAMPLE 104

(3R)-3-methoxy-4-(6-methyl-5-oxo-2,3,3a,4,5,6-hexahydro-1H-6,8,10,10b-tetraaza-benzo[e]azulen-9-ylamino)-N-(1-methyl-piperidin-4-yl)-benzamide (I-102)

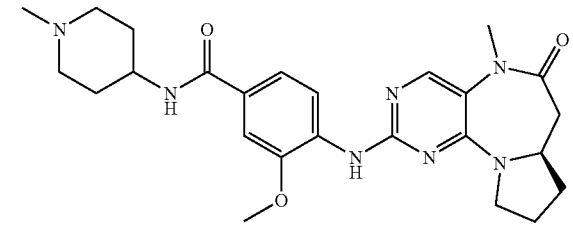

Step a

To a solution of 2.0 g (0.012 mole) of D-beta-homoproline hydrochloride in 20 mL of methanol was added slowly 1.8 mL (0.024 mole) of thionyl chloride at 0 degrees. The mixture was stirred overnight, then concentrated under reduced pressure. The solid was slurried in ether, and collected by filtration to give 2.2 g of (2R)-pyrrolidin-2-yl-acetic acid methyl ester hydrochloride as a white solid. A solution of 2.2 g (0.012 mole) of (2R)-pyrrolidin-2-yl-acetic acid methyl ester hydrochloride in 3 mL of chloroform was added over 5 minutes to a cooled (0 degrees) mixture of 2.34 g (0.012 mole) of 2,4-dichloro-5-nitro-pyrimidine, 5.1 g (0.060 mole) of sodium bicarbonate and 25 mL of ethyl acetate. The cooling bath was removed and the mixture stirred for 17 hours at room temperature. Activated charcoal was added and after stirring briefly, the mixture was filtered through a pad of Celite, washing the filter pad with ethyl acetate. The filtrate was concentrated under reduced pressure. Purification of the residue by silica gel chromatography, eluting with hexanes-ethyl acetate (100:0-70:30) gave 3.3 g of [(R)-1-(2-chloro-5-nitro-pyrimidin-4-yl)-pyrrolidin-2-yl]-acetic acid methyl ester (IV-102) as a yellow thick oil.

Step b

A mixture of 3.3 g (0.011 mole) of [(R)-1-(2-chloro-5-nitro-pyrimidin-4-yl)-pyrrolidin-2-yl]-acetic acid methyl ester (IV-102) in 150 mL of ethyl acetate and 0.8 g of 10% palladium on carbon catalyst was stirred under an atmosphere of hydrogen until hydrogen uptake was complete. The mixture was filtered through a pad of Celite, washing the filter pad with dichloromethane. The filtrate was concentrated under reduced pressure to give [(R)-1-(5-amino-2-chloro-pyrimidin-4-yl)-pyrrolidin-2-yl]-acetic acid methyl ester (V-102), which also contained a small amount of (R)-9-chloro-2,3,3a,4-tetrahydro-1H,6H-6,8,10,10b-tetraaza-benzo[e]azulen-5-one. This material was used directly in the next step without further purification.

Step c

A mixture of 150 mL of ethanol, 2.5 mL of acetic acid and (R)-9-chloro-2,3,3a,4-tetrahydro-1H,6H-6,8,10,10b-tetraaza-benzo[e]azulen-5-one (V-102) prepared in the previous step was heated at reflux overnight, and then concentrated under reduced pressure. The residue was taken up in dichloromethane and washed successively with 10% sodium bicarbonate solution, and then water and dried over anhydrous sodium sulfate. The mixture was filtered and then concentrated under reduced pressure. Purification of the residue by silica gel chromatography, eluting with hexanes-ethyl acetate (40:60-0:100) gave 0.45 g of (R)-9-chloro-2,3,3a,4-tetrahydro-1H,6H-6,8,10,10b-tetraaza-benzo[e]azulen-5-one (VI-102) as a solid.

Step d

To a solution of 0.4 g (0.0017 mole) of (R)-9-chloro-2,3,3a,4-tetrahydro-1H,6H-6,8,10,10b-tetraaza-benzo[e]azulen-5-one (VI-102) in 10 mL of dimethylformamide was added 1.1 g (0.0034 mole) of cesium carbonate, followed by 0.32 mL (0.0051 mole) of iodomethane. After stirring overnight, the mixture was filtered and the filtrate concentrated under reduced pressure. Purification of the residue by silica gel chromatography, eluting with hexanes-ethyl acetate (40:60-0:100) gave 0.35 g of (R)-9-chloro-6-methyl-2,3,3a,4-tetrahydro-1H,6H-6,8,10,10b-tetraaza-benzo[e]azulen-5-one (VII-102) as a light yellow solid.

Step e

A mixture of 0.15 g (0.0006 mole) of (R)-9-chloro-6-methyl-2,3,3a,4-tetrahydro-1H,6H-6,8,10,10b-tetraaza-benzo[e]azulen-5-one (VII-102) and 0.11 g (0.00066 mole) of 4-amino-3-methoxy-benzoic acid (Aldrich) in 15 mL of ethanol-water-hydrochloric acid (20:80:1) was heated by microwave at 160 degrees for 40 minutes, and then concentrated under reduced pressure. The residue was lyophilized to give crude 3-methoxy-4-((R)-6-methyl-5-oxo-2,3,3a,4,5,6-hexahydro-1H-6,8,10,10b-tetraaza-benzo[e]azulen-9-ylamino)-benzoic acid (I-102a) as a light yellow solid which was used without further purification in subsequent steps.

Step f

To a mixture of 3-methoxy-4-((R)-6-methyl-5-oxo-2,3,3a,4,5,6-hexahydro-1H-6,8,10,10b-tetraaza-benzo[e]azulen-9-ylamino)-benzoic acid (I-102a), 0.32 mL (0.0018 mole) of ethyldiisopropylamine and 0.082 g (0.00072 mole) of 4-amino-1-methyl-piperidine in 3.0 mL of dimethylformamide was added 0.31 g (0.00072 mole) of 1-(di-1-pyrrolidinylmethylene)-1H-benzotriazolium 3-oxide hexafluorophosphate. The mixture was stirred at room temperature for 3 hours, then diluted with saturated sodium carbonate. The mixture was extracted with ethyl acetate three times. The combined organic layers were dried over anhydrous sodium sulfate, filtered and concentrated under reduced pressure. Purification of the residue by silica gel chromatography, eluting with dichloromethane-methanol (100:0-60:40) gave 0.060 g of 3-methoxy-4-((R)-6-methyl-5-oxo-2,3,3a,4,5,6-hexahydro-1H-6,8,10,10b-tetraaza-benzo[e]azulen-9-ylamino)-N-(1-methyl-piperidin-4-yl)-benzamide (I-102).

EXAMPLE 105

(3S)-3-Methoxy-4-(6-methyl-5-oxo-2,3,3a,4,5,6-hexahydro-1H-6,8,10,10b-tetraaza-benzo[e]azulen-9-ylamino)-N-(1-methyl-piperidin-4-yl)-benzamide (I-103)

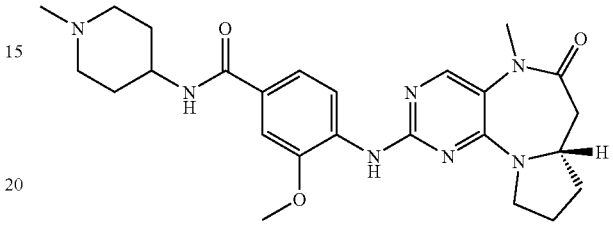

Prepared from L-beta-homoproline, according to the method described in example 104.

Biochemical Characterization Assay

Full-length, active GST-PLK1 is purified from Sf9 insect cells, and full-length GST-p53 is purified from *E. coli*. Anti-phospho p53 antibody is from Cell Signaling Technology. Europium-conjugated anti-rabbit antibody is from PerkinElmer Life and Analytical Sciences. APC-conjugated anti-GST antibody is from Prozyme.

To assay compounds of the invention, two microliters of test compound (0.6 nM-4 mM) in DMSO or plain DMSO for control wells, 38 microliters of 20 mM HEPES pH 7, 50 mM NaCl, 10 mM $MgCl_2$, 0.5 mM TCEP, 0.1 mM sodium orthovanadate, 0.1 mg/mL BSA, and 0.05% Triton X-100 (Kinase Assay Buffer) are added. Eight microliters of the compound solution are added to a 384-well black microtiter plate, followed by six microliters of GST-p53 (17 ug/mL) and ATP (333 uM) in Kinase Assay Buffer. Six microliters of GST-PLK1 (3 ug/mL) in Kinase Assay Buffer are then added and the solution incubated at 37° C. for 35 minutes. Six microliters of solution containing 43 mM EDTA to stop the reaction and a 1:600 dilution of anti-phospho-p53 antibody in 20 mM HEPES pH 7, 50 mM NaCl, and 0.5 mg/mL BSA (Antibody Binding Buffer) are added and the solution incubated at 37° C. for 30 minutes. Six microliters of solution containing 9 nM europium-conjugated anti-rabbit antibody and 120 nM APC-conjugated anti-GST antibody in Antibody Binding Buffer are then added and the mixture incubated at room temperature for 1.5 hours. The HTRF signal is read on an Envision reader from PerkinElmer Life and Analytical Sciences. The key for the IC50 ranges is: A<500 nM; B 500-5000 nM; C>5000 nM; N.D. not determined)

TABLE 1

| Ex | cpd | MW | MH+/z | $IC_{50}$ nM | Name |
|---|---|---|---|---|---|
| 1 | I-1 | 425.49 | 426 | N.D. | (rac)-4-(9-cyclopentyl-5,7-dimethyl-6-oxo-6,7,8,9-tetrahydro-5H-pyrimido[4,5-b][1,4]diazepin-2-ylamino)-3-methoxy-benzoic acid |
| 2 | I-2 | 521.67 | 522 | A | (rac)-4-(9-cyclopentyl-5,7-dimethyl-6-oxo-6,7,8,9-tetrahydro-5H-pyrimido[4,5- |

TABLE 1-continued

| Ex | cpd | MW | MH+/z | IC$_{50}$ nM | Name |
|---|---|---|---|---|---|
| | | | | | b][1,4]diazepin-2-ylamino)-3-methoxy-N-(1-methyl-piperidin-4-yl)-benzamide |
| 4 | I-2a | 521.67 | 522 | A | 7R-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 4 | I-2b | 521.67 | 522 | A | 7S-4-(9-cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 5 | I-3 | 425.49 | 426 | B | (rac)-4-(9-cyclopentyl-5,8-dimethyl-6-oxo-6,7,8,9-tetrahydro-5H-pyrimido[4,5-b][1,4]diazepin-2-ylamino)-3-methoxy-benzoic acid |
| 6 | I-4 | 521.67 | 522 | A | (rac)-4-(9-cyclopentyl-5,8-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 7 | I-5 | 395.47 | 396 | N.D. | (rac)-4-(9-cyclopentyl-5,7-dimethyl-6-oxo-6,7,8,9-tetrahydro-5H-pyrimido[4,5-b][1,4]diazepin-2-ylamino)-benzoic acid |
| 8 | I-6 | 491.64 | 492 | A | (rac)-4-(9-cyclopentyl-5,7-dimethyl-6-oxo-6,7,8,9-tetrahydro-5H-pyrimido[4,5-b][1,4]diazepin-2-ylamino)-N-(1-methyl-piperidin-4-yl)-benzamide |
| 9 | I-7 | 409.49 | 410 | N.D. | (rac)-4-(9-cyclopentyl-5,7-dimethyl-6-oxo-6,7,8,9-tetrahydro-5H-pyrimido[4,5-b][1,4]diazepin-2-ylamino)-3-methyl-benzoic acid |
| 10 | I-8 | 505.67 | 506 | A | (rac)-4-(9-cyclopentyl-5,7-dimethyl-6-oxo-6,7,8,9-tetrahydro-5H-pyrimido[4,5-b][1,4]diazepin-2-ylamino)-3-methyl-N-(1-methyl-piperidin-4-yl)-benzamide |
| 11 | I-9 | 597.77 | 598 | A | (rac)-N-(1-benzyl-piperidin-4-yl)-4-(9-cyclopentyl-5,7-dimethyl-6-oxo-6,7,8,9-tetrahydro-5H-pyrimido[4,5-b][1,4]diazepin-2-ylamino)-3-methoxy-benzamide |
| 12 | I-10 | 411.46 | 412 | N.D. | 4-(9-cyclopentyl-5-methyl-6-oxo-6,7,8,9-tetrahydro-5H-pyrimido[4,5-b][1,4]diazepin-2-ylamino)-3-methoxy-benzoic acid |
| 13 | I-11 | 507.64 | 508 | A | 4-(9-cyclopentyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 14 | I-12 | 439.52 | 440 | N.D. | (rac)-4-(9-cyclopentyl-7-ethyl-5-methyl-6-oxo-6,7,8,9-tetrahydro-5H-pyrimido[4,5-b][1,4]diazepin-2-ylamino)-3-methoxy-benzoic acid |
| 15 | I-13 | 535.70 | 536 | A | (rac)-4-(9-cyclopentyl-7-ethyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 16 | I-14 | 453.55 | 454 | N.D. | (rac)-4-(9-cyclopentyl-5,7-diethyl-6-oxo-6,7,8,9-tetrahydro-5H-pyrimido[4,5-b][1,4]diazepin-2-ylamino)-3-methoxy-benzoic acid |
| 17 | I-15 | 549.72 | 550 | B | (rac)-4-(9-cyclopentyl-5,7-diethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 18 | I-16 | 453.55 | 454 | N.D. | (rac)-4-(9-cyclopentyl-5-methyl-6-oxo-7-propyl-6,7,8,9-tetrahydro-5H-pyrimido[4,5-b][1,4]diazepin-2-ylamino)-3-methoxy-benzoic acid |
| 19 | I-17 | 549.72 | 550 | B | (rac)-4-(9-cyclopentyl-5-methyl-6-oxo-7-propyl-6,7,8,9-tetrahydro-5H-pyrimido[4,5-b][1,4]diazepin-2-ylamino)-3-methoxy-N-(1-methyl-piperidin-4-yl)-benzamide |
| 20 | I-18 | 521.67 | 522 | B | (rac)-4-(9-cyclohexyl-7-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |

TABLE 1-continued

| Ex | cpd | MW | MH+/z | IC$_{50}$ nM | Name |
|---|---|---|---|---|---|
| 21 | I-19 | 535.70 | 536 | A | (rac)-4-(9-cyclohexyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 22 | I-20 | 521.67 | 522 | A | 4-(9-cyclohexyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 23 | I-21 | 493.61 | 494 | B | 4-(9-cyclopentyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 24 | I-22 | 529.65 | 530 | B | 4-(9-benzyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 25 | I-23 | 397.44 | 398 | N.D. | 4-(9-cyclobutyl-5-methyl-6-oxo-6,7,8,9-tetrahydro-5H-pyrimido[4,5-b][1,4]diazepin-2-ylamino)-3-methoxy-benzoic acid |
| 26 | I-24 | 493.61 | 494 | A | 4-(9-cyclobutyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 27 | I-25 | 353.43 | 354 | C | 9-cyclobutyl-2-(2-methoxy-phenylamino)-5-methyl-5,7,8,9-tetrahydro-pyrimido[4,5-b][1,4]diazepin-6-one |
| 28 | I-26 | 483.58 | 484 | C | (rac)-9-cyclohexyl-5,7-dimethyl-2-(2-pyridin-4-yl-benzooxazol-5-ylamino)-5,7,8,9-tetrahydro-pyrimido[4,5-b][1,4]diazepin-6-one |
| 29 | I-27 | 523.68 | 524 | B | (rac)-4-[5,7-dimethyl-9-(3-methyl-butyl)-6-oxo-6,7,8,9-tetrahydro-5H-pyrimido[4,5-b][1,4]diazepin-2-ylamino]-3-methoxy-N-(1-methyl-piperidin-4-yl)-benzamide |
| 30 | I-28 | 486.58 | 487 | C | 4-(9-cyclohexyl-6-oxo-6,7,8,9-tetrahydro-5H-pyrimido[4,5-b][1,4]diazepin-2-ylamino)-3-methoxy-N-phenyl-benzamide |
| 31 | I-29 | 507.64 | 508 | B | 4-(9-cyclohexyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 32 | I-30 | 452.56 | 453 | C | 4-(9-cyclohexyl-6-oxo-6,7,8,9-tetrahydro-5H-pyrimido[4,5-b][1,4]diazepin-2-ylamino)-3-methoxy-N-propyl-benzamide |
| 33 | I-31 | 480.57 | 481 | C | 9-cyclohexyl-2-[2-methoxy-4-(morpholine-4-carbonyl)-phenylamino]-5,7,8,9-tetrahydro-pyrimido[4,5-b][1,4]diazepin-6-one |
| 34 | I-32 | 478.60 | 479 | C | 9-cyclohexyl-2-[2-methoxy-4-(piperidine-1-carbonyl)-phenylamino]-5,7,8,9-tetrahydro-pyrimido[4,5-b][1,4]diazepin-6-one |
| 35 | I-33 | 494.60 | 495 | C | 4-(9-cyclohexyl-6-oxo-6,7,8,9-tetrahydro-5H-pyrimido[4,5-b][1,4]diazepin-2-ylamino)-3-methoxy-N-(tetrahydro-pyran-4-yl)-benzamide |
| 36 | I-34 | 396.45 | 397 | B | 4-(9-cyclobutyl-5-methyl-6-oxo-6,7,8,9-tetrahydro-5H-pyrimido[4,5-b][1,4]diazepin-2-ylamino)-3-methoxy-benzamide |
| 36 | I-35 | 424.51 | 425 | C | 4-(9-cyclobutyl-5-methyl-6-oxo-6,7,8,9-tetrahydro-5H-pyrimido[4,5-b][1,4]diazepin-2-ylamino)-3-methoxy-N,N-dimethyl-benzamide |
| 38 | I-36 | 504.60 | 505 | A | 4-(9-cyclobutyl-5-methyl-6-oxo-6,7,8,9-tetrahydro-5H-pyrimido[4,5-b][1,4]diazepin-2-ylamino)-N-(3-imidazol-1-yl-propyl)-3-methoxy-benzamide |
| 39 | I-37 | 473.54 | 474 | A | 4-(9-cyclobutyl-5-methyl-6-oxo-6,7,8,9-tetrahydro-5H-pyrimido[4,5-b][1,4]diazepin-2-ylamino)-3-methoxy-N-pyridin-4-yl-benzamide |
| 40 | I-38 | 439.52 | 440 | | 4-(9-cyclopentyl-5,7,7-trimethyl-6-oxo-6,7,8,9-tetrahydro-5H-pyrimido[4,5-b][1,4]diazepin-2-ylamino)-3-methoxy-benzoic acid |

TABLE 1-continued

| Ex | cpd | MW | MH+/z | IC$_{50}$ nM | Name |
|---|---|---|---|---|---|
| 41 | I-39 | 535.70 | 536 | A | 4-(9-cyclopentyl-5,7,7-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 42 | I-40 | 497.60 | 498 | B | 3-methoxy-4-[9-(2-methoxy-ethyl)-5-methyl-6-oxo-6,7,8,9-tetrahydro-5H-pyrimido[4,5-b][1,4]diazepin-2-ylamino]-N-(1-methyl-piperidin-4-yl)-benzamide |
| 43 | I-41 | 535.70 | 536 | A | (rac)-4-(9-cyclopentyl-5,7,8-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 44 | I-42 | 543.67 | 544 | B | (rac)-4-(9-benzyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 45 | I-43 | 481.60 | 482 | A | 4-(9-isopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 46 | I-44 | 495.63 | 496 | A | 4-(9-butyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 47 | I-45 | 537.67 | 538 | A | (rac)-4-[5,7-dimethyl-6-oxo-9-(tetrahydro-pyran-4-yl)-6,7,8,9-tetrahydro-5H-pyrimido[4,5-b][1,4]diazepin-2-ylamino]-3-methoxy-N-(1-methyl-piperidin-4-yl)-benzamide |
| 48 | I-46 | 507.64 | 508 | A | (rac)-4-(9-cyclopropyl-5,7,8-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 49 | I-47 | 487.57 | 488 | B | (rac)-N-[5-(9-cyclopentyl-5,7-dimethyl-6-oxo-6,7,8,9-tetrahydro-5H-pyrimido[4,5-b][1,4]diazepin-2-ylamino)-2-hydroxy-phenyl]-nicotinamide |
| 50 | I-48 | 487.57 | 488 | B | (rac)-N-[5-(9-cyclopentyl-5,7-dimethyl-6-oxo-6,7,8,9-tetrahydro-5H-pyrimido[4,5-b][1,4]diazepin-2-ylamino)-2-hydroxy-phenyl]-isonicotinamide |
| 51 | I-49 | 551.69 | 552 | B | (rac)-4-[9-cyclopentyl-7-(2-hydroxy-ethyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide |
| 52 | I-50 | 505.67 | 506 | A | 4-(9-cyclopentyl-5,7,7-trimethyl-6-oxo-6,7,8,9-tetrahydro-5H-pyrimido[4,5-b][1,4]diazepin-2-ylamino)-N-(1-methyl-piperidin-4-yl)-benzamide |
| 53 | I-51 | 529.65 | 530 | B | (rac)-4-(5,7-dimethyl-6-oxo-9-phenyl-6,7,8,9-tetrahydro-5H-pyrimido[4,5-b][1,4]diazepin-2-ylamino)-3-methoxy-N-(1-methyl-piperidin-4-yl)-benzamide |
| 54 | I-52 | 507.64 | 508 | A | (rac)-4-(9-cyclobutyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 55 | I-53 | 437.50 | 438 | N.D. | 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methoxybenzoic acid |
| 56 | I-54 | 533.68 | 534 | A | 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methoxy-N-(1-methyl-4-piperidinyl)benzamide |
| 57 | I-55 | 535.70 | 536 | A | (rac)-4-(9-cyclopentylmethyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 58 | I-56 | 519.70 | 520 | A | 4-(9-cyclopentyl-5,7,7-trimethyl-6-oxo-6,7,8,9-tetrahydro-5H-pyrimido[4,5-b][1,4]diazepin-2-ylamino)-3-methyl-N-(1-methyl-piperidin-4-yl)-benzamide |
| 59 | I-57 | 521.67 | 522 | A | (rac)-3-methoxy-4-[5-methyl-9-(2-methyl-cyclopentyl)-6-oxo-6,7,8,9-tetrahydro-5H- |

TABLE 1-continued

| Ex | cpd | MW | MH+/z | IC$_{50}$ nM | Name |
|---|---|---|---|---|---|
| 60 | I-58 | 521.67 | 522 | A | pyrimido[4,5-b][1,4]diazepin-2-ylamino]-N-(1-methyl-piperidin-4-yl)-benzamide (rac)-3-methoxy-4-[5-methyl-9-(3-methyl-cyclopentyl)-6-oxo-6,7,8,9-tetrahydro-5H-pyrimido[4,5-b][1,4]diazepin-2-ylamino]-N-(1-methyl-piperidin-4-yl)-benzamide |
| 61 | I-59 | 535.70 | 536 | A | 4-[9-(2,2-dimethyl-cyclopentyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide |
| 62 | I-60 | 421.50 | 422 | N.D. | 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methylbenzoic acid |
| 63 | I-61 | 517.68 | 518 | A | 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-3-methyl-N-(1-methyl-4-piperidinyl)benzamide |
| 64 | I-62 | 503.65 | 504 | A | 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-N-(1-methyl-4-piperidinyl)benzamide |
| 65 | I-63 | 490.61 | 491 | A | 4-[(9-cyclopentyl-6,7,8,9-tetrahydro-5-methyl-6-oxospiro[5H-pyrimido[4,5-b][1,4]diazepine-7,1'-cyclopropan]-2-yl)amino]-N-(tetrahydropyran-4-yl)benzamide |
| 66 | I-64 | 541.72 | 542 | B | 4-(9-cyclopentyl-5,7,7-trimethyl-6-oxo-6,7,8,9-tetrahydro-5H-pyrimido[4,5-b][1,4]diazepin-2-ylamino)-N-(1-methyl-piperidin-4-yl)-benzenesulfonamide |
| 67 | I-65 | 493.61 | 494 | A | (rac)-4-(9-allyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 68 | I-66 | 549.72 | 550 | C | (rac)-4-[(9-cyclohexyl-5,7-dimethyl-6-oxo-6,7,8,9-tetrahydro-5H-pyrimido[4,5-b][1,4]diazepin-2-yl)-methyl-amino]-3-methoxy-N-(1-methyl-piperidin-4-yl)-benzamide |
| 69 | I-67 | 479.59 | 480 | C | (rac)-3-methoxy-4-(8-methyl-9-oxo-1,3,5,8-tetraaza-tricyclo[8.3.1.0*2,7*]tetradeca-2,4,6-trien-4-ylamino)-N-(1-methyl-piperidin-4-yl)-benzamide |
| 70 | I-68 | 547.71 | 548 | A | (rac)-4-(4-cyclopentyl-9-methyl-10-oxo-1,2,3,3a,4,9,10,10a-octahydro-4,5,7,9-tetraaza-benzo[f]azulen-6-ylamino)-3-methoxy-N-(1-methyl-piperidin-4-yl)-benzamide |
| 71 | I-69 | 491.64 | 492 | B | (rac)-3-(9-cyclopentyl-5,7-dimethyl-6-oxo-6,7,8,9-tetrahydro-5H-pyrimido[4,5-b][1,4]diazepin-2-ylamino)-N-(1-methyl-piperidin-4-yl)-benzamide |
| 72 | I-70 | 479.63 | 480 | B | (rac)-3-(9-cyclopentyl-5,7-dimethyl-6-oxo-6,7,8,9-tetrahydro-5H-pyrimido[4,5-b][1,4]diazepin-2-ylamino)-N-(3-dimethylamino-propyl)-benzamide |
| 73 | I-71 | 478.60 | 479 | B | (rac)-3-(9-cyclopentyl-5,7-dimethyl-6-oxo-6,7,8,9-tetrahydro-5H-pyrimido[4,5-b][1,4]diazepin-2-ylamino)-N-(tetrahydro-pyran-4-yl)-benzamide |
| 74 | I-72 | 471.57 | 472 | A | (rac)-3-(9-cyclopentyl-5,7-dimethyl-6-oxo-6,7,8,9-tetrahydro-5H-pyrimido[4,5-b][1,4]diazepin-2-ylamino)-N-pyridin-3-yl-benzamide |
| 75 | I-73 | 509.67 | 510 | A | (rac)-3-(9-cyclopentyl-5,7-dimethyl-6-oxo-6,7,8,9-tetrahydro-5H-pyrimido[4,5-b][1,4]diazepin-2-ylamino)-N-(3-dimethylamino-propyl)-4-methoxy-benzamide |
| 76 | I-74 | 508.63 | 509 | A | (rac)-3-(9-cyclopentyl-5,7-dimethyl-6-oxo-6,7,8,9-tetrahydro-5H-pyrimido[4,5-b][1,4]diazepin-2-ylamino)-4-methoxy-N-(tetrahydro-pyran-4-yl)-benzamide |

TABLE 1-continued

| Ex | cpd | MW | MH+/z | IC$_{50}$ nM | Name |
|---|---|---|---|---|---|
| 77 | I-75 | 457.58 | 458 | C | (rac)-2-(4-benzyloxy-phenylamino)-9-cyclopentyl-5,7-dimethyl-5,7,8,9-tetrahydro-pyrimido[4,5-b][1,4]diazepin-6-one |
| 78 | I-76 | 469.55 | 470 | C | (rac)-9-cyclopentyl-5,7-dimethyl-2-(2-pyridin-4-yl-benzooxazol-5-ylamino)-5,7,8,9-tetrahydro-pyrimido[4,5-b][1,4]diazepin-6-one |
| 79 | I-77 | 469.55 | 470 | C | (rac)-9-cyclopentyl-5,7-dimethyl-2-(2-pyridin-3-yl-benzooxazol-5-ylamino)-5,7,8,9-tetrahydro-pyrimido[4,5-b][1,4]diazepin-6-one |
| 80 | I-78 | 500.61 | 501 | B | (rac)-N-[3-(9-cyclopentyl-5,7-dimethyl-6-oxo-6,7,8,9-tetrahydro-5H-pyrimido[4,5-b][1,4]diazepin-2-ylamino)-4-methoxy-phenyl]-benzamide |
| 81 | I-79 | 439.52 | 440 | A | (rac)-4-(9-cyclopentyl-5,7-dimethyl-6-oxo-6,7,8,9-tetrahydro-5H-pyrimido[4,5-b][1,4]diazepin-2-ylamino)-3-methoxy-benzoic acid hydrazide |
| 82 | I-80 | 549.68 | 550 | B | (rac)-1-acetyl-piperidine-4-carboxylic acid [3-(9-cyclopentyl-5,7-dimethyl-6-oxo-6,7,8,9-tetrahydro-5H-pyrimido[4,5-b][1,4]diazepin-2-ylamino)-4-methoxy-phenyl]-amide |
| 83 | I-81 | 540.11 | 540 | B | (rac)-2-chloro-4-(9-cyclopentyl-5,7-dimethyl-6-oxo-6,7,8,9-tetrahydro-5H-pyrimido[4,5-b][1,4]diazepin-2-ylamino)-N-(1-ethyl-piperidin-4-yl)-benzamide |
| 84 | I-82 | 506.01 | 506 | C | (rac)-2-chloro-4-(9-cyclopentyl-5,7-dimethyl-6-oxo-6,7,8,9-tetrahydro-5H-pyrimido[4,5-b][1,4]diazepin-2-ylamino)-N-pyridin-3-yl-benzamide |
| 85 | I-83 | 514.08 | 514 | B | (rac)-2-chloro-4-(9-cyclopentyl-5,7-dimethyl-6-oxo-6,7,8,9-tetrahydro-5H-pyrimido[4,5-b][1,4]diazepin-2-ylamino)-N-(3-dimethylamino-propyl)-benzamide |
| 86 | I-84 | 526.09 | 526 | A | (rac)-2-chloro-4-(9-cyclopentyl-5,7-dimethyl-6-oxo-6,7,8,9-tetrahydro-5H-pyrimido[4,5-b][1,4]diazepin-2-ylamino)-N-(1-methyl-piperidin-4-yl)-benzamide |
| 87 | I-85 | 511.07 | 511 | C | (rac)-2-chloro-N-cyclohexyl-4-(9-cyclopentyl-5,7-dimethyl-6-oxo-6,7,8,9-tetrahydro-5H-pyrimido[4,5-b][1,4]diazepin-2-ylamino)-benzamide |
| 88 | I-86 | 506.01 | 506 | C | (rac)-2-chloro-4-(9-cyclopentyl-5,7-dimethyl-6-oxo-6,7,8,9-tetrahydro-5H-pyrimido[4,5-b][1,4]diazepin-2-ylamino)-N-pyridin-4-yl-benzamide |
| 89 | I-87 | 500.05 | 500 | B | (rac)-2-chloro-4-(9-cyclopentyl-5,7-dimethyl-6-oxo-6,7,8,9-tetrahydro-5H-pyrimido[4,5-b][1,4]diazepin-2-ylamino)-N-(2-dimethylamino-ethyl)-benzamide |
| 90 | I-88 | 513.04 | 513 | B | (rac)-2-chloro-4-(9-cyclopentyl-5,7-dimethyl-6-oxo-6,7,8,9-tetrahydro-5H-pyrimido[4,5-b][1,4]diazepin-2-ylamino)-N-(tetrahydro-pyran-4-yl)-benzamide |
| 91 | I-89 | 505.67 | 506 | B | (rac)-3-(9-cyclopentyl-5,7-dimethyl-6-oxo-6,7,8,9-tetrahydro-5H-pyrimido[4,5-b][1,4]diazepin-2-ylamino)-N-(1-ethyl-piperidin-4-yl)-benzamide |
| 92 | I-90 | 466.59 | 467 | B | (rac)-3-(9-cyclopentyl-5,7-dimethyl-6-oxo-6,7,8,9-tetrahydro-5H-pyrimido[4,5-b][1,4]diazepin-2-ylamino)-N-(3-methoxy-propyl)-benzamide |
| 93 | I-91 | 476.63 | 477 | C | (rac)-N-cyclohexyl-3-(9-cyclopentyl-5,7-dimethyl-6-oxo-6,7,8,9-tetrahydro-5H-pyrimido[4,5-b][1,4]diazepin-2-ylamino)-benzamide |
| 94 | I-92 | 471.57 | 472 | C | (rac)-3-(9-cyclopentyl-5,7-dimethyl-6-oxo-6,7,8,9-tetrahydro-5H-pyrimido[4,5-b][1,4]diazepin-2-ylamino)-N-pyridin-4-yl-benzamide |
| 95 | I-93 | 465.60 | 466 | B | (rac)-3-(9-cyclopentyl-5,7-dimethyl-6-oxo-6,7,8,9-tetrahydro-5H-pyrimido[4,5-b][1,4]diazepin-2-ylamino)-N-(2-dimethylamino-ethyl)-benzamide |

TABLE 1-continued

| Ex | cpd | MW | MH+/z | IC$_{50}$ nM | Name |
|---|---|---|---|---|---|
| 96 | I-94 | 505.67 | 506 | N.D. | (rac)-4-(9-cyclopentyl-5,7-dimethyl-6-oxo-6,7,8,9-tetrahydro-5H-pyrimido[4,5-b][1,4]diazepin-2-ylamino)-N-(1-ethyl-piperidin-4-yl)-benzamide |
| 97 | I-95 | 479.63 | 480 | N.D. | (rac)-4-(9-cyclopentyl-5,7-dimethyl-6-oxo-6,7,8,9-tetrahydro-5H-pyrimido[4,5-b][1,4]diazepin-2-ylamino)-N-(3-dimethylamino-propyl)-benzamide |
| 98 | I-96 | 466.59 | 467 | N.D. | (rac)-4-(9-cyclopentyl-5,7-dimethyl-6-oxo-6,7,8,9-tetrahydro-5H-pyrimido[4,5-b][1,4]diazepin-2-ylamino)-N-(3-methoxy-propyl)-benzamide |
| 99 | I-97 | 519.70 | 520 | N.D. | (rac)-4-(9-cyclopentyl-5,7-dimethyl-6-oxo-6,7,8,9-tetrahydro-5H-pyrimido[4,5-b][1,4]diazepin-2-ylamino)-N-(1-ethyl-piperidin-4-yl)-3-methyl-benzamide |
| 100 | I-98 | 493.66 | 494 | N.D. | (rac)-4-(9-cyclopentyl-5,7-dimethyl-6-oxo-6,7,8,9-tetrahydro-5H-pyrimido[4,5-b][1,4]diazepin-2-ylamino)-N-(3-dimethylamino-propyl)-3-methyl-benzamide |
| 101 | I-99 | 480.62 | 481 | N.D. | (rac)-4-(9-cyclopentyl-5,7-dimethyl-6-oxo-6,7,8,9-tetrahydro-5H-pyrimido[4,5-b][1,4]diazepin-2-ylamino)-N-(3-methoxy-propyl)-3-methyl-benzamide |
| 102 | I-100 | 447.45 | 448 | N.D. | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid |
| 103 | I-101 | 543.62 | 544 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 104 | I-102 | 479.59 | 480 | A | (3R)-3-methoxy-4-(6-methyl-5-oxo-2,3,3a,4,5,6-hexahydro-1H-6,8,10,10b-tetraaza-benzo[e]azulen-9-ylamino)-N-(1-methyl-piperidin-4-yl)-benzamide |
| 105 | I-103 | 479.59 | 480 | N.D. | (3S)-3-methoxy-4-(6-methyl-5-oxo-2,3,3a,4,5,6-hexahydro-1H-6,8,10,10b-tetraaza-benzo[e]azulen-9-ylamino)-N-(1-methyl-piperidin-4-yl)-benzamide |

What is claimed is:

1. A compound of formula I:

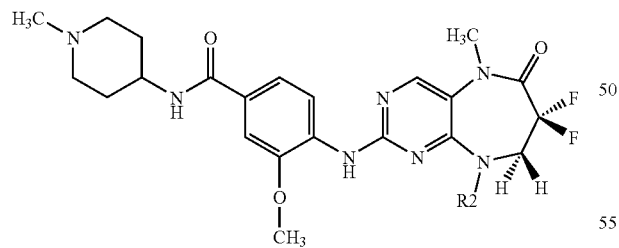
(I)

wherein
R2 is a member selected from the group consisting of cyclopentyl and cyclohexyl; and pharmaceutically acceptable salts thereof.

2. The compound of claim 1 wherein R2 is cyclopentyl.

3. The compound 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid and pharmaceutically acceptable salts thereof.

4. The compound with the formula

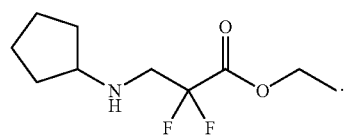

5. A pharmaceutical composition comprising a compound of claim 1 and a pharmaceutically acceptable excipient.

6. A pharmaceutical composition comprising a compound of claim 2 and a pharmaceutically acceptable excipient.

7. A pharmaceutical composition comprising a compound of claim 3 and a pharmaceutically acceptable excipient.

* * * * *

Disclaimer

7,517,873 B2 — Shaoqing Chen, Bridgewater, NJ (US). SUBSTITUTED PYRIMIDODIAZEPINES. Patent dated April 14, 2009. Disclaimer filed May 30, 2012, by the inventor.

Hereby disclaims complete claims 1-3 and 5-7 of said patent.

*(Official Gazette, July 24, 2012)*